US007919273B2

(12) United States Patent
Goldenberg et al.

(10) Patent No.: US 7,919,273 B2
(45) Date of Patent: Apr. 5, 2011

(54) STRUCTURAL VARIANTS OF ANTIBODIES FOR IMPROVED THERAPEUTIC CHARACTERISTICS

(75) Inventors: David M. Goldenberg, Mendham, NJ (US); Chien-Hsing Chang, Downingtown, PA (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 12/506,992

(22) Filed: Jul. 21, 2009

(65) Prior Publication Data

US 2010/0034738 A1 Feb. 11, 2010

Related U.S. Application Data

(60) Provisional application No. 61/082,399, filed on Jul. 21, 2008.

(51) Int. Cl.
*C12P 21/04* (2006.01)
*C12N 7/00* (2006.01)
*A61K 39/395* (2006.01)
*C12P 21/08* (2006.01)
*C07K 16/00* (2006.01)

(52) U.S. Cl. .................. 435/69.6; 424/133.1; 424/141.1; 424/143.1; 424/155.1; 435/70.21; 530/387.3; 530/388.1; 530/388.22; 530/388.8

(58) Field of Classification Search .................. None
See application file for complete search history.

(56) References Cited

U.S. PATENT DOCUMENTS

| | | |
|---|---|---|
| 4,036,945 A | 7/1977 | Haber |
| 4,046,722 A | 9/1977 | Rowland |
| 4,331,647 A | 5/1982 | Goldenberg |
| 4,699,784 A | 10/1987 | Shih |
| 4,704,692 A | 11/1987 | Ladner |
| 4,824,659 A | 4/1989 | Hawthorne |
| 4,946,778 A | 8/1990 | Ladner |
| 5,057,313 A | 10/1991 | Shih |
| 5,229,275 A | 7/1993 | Goroff |
| 5,443,953 A | 8/1995 | Hansen |
| 5,530,101 A | 6/1996 | Queen et al. |
| 5,567,610 A | 10/1996 | Borrebaeck |
| 5,633,425 A | 5/1997 | Lonberg |
| 5,734,033 A | 3/1998 | Reed |
| 5,736,137 A | 4/1998 | Anderson et al. |
| 5,776,456 A | 7/1998 | Anderson et al. |
| 5,798,554 A | 8/1998 | Grimaldi |
| 5,827,690 A | 10/1998 | Meade |
| 6,077,499 A | 6/2000 | Griffiths |
| 6,183,744 B1 | 2/2001 | Goldenberg |
| 6,187,287 B1 | 2/2001 | Leung |
| 6,254,868 B1 | 7/2001 | Leung |
| 6,331,175 B1 | 12/2001 | Goldenberg |
| 6,897,044 B1 | 5/2005 | Braslawsky et al. |
| 7,074,403 B1 | 7/2006 | Goldenberg et al. |
| 7,151,164 B2 | 12/2006 | Hansen |
| 7,321,026 B2 | 1/2008 | Leung |
| 7,338,659 B2 | 3/2008 | Leung |
| 7,435,803 B2 | 10/2008 | Hansen |
| 2002/0004587 A1 | 1/2002 | Miller et al. |
| 2002/0009427 A1 | 1/2002 | Wolin et al. |
| 2002/0009444 A1 | 1/2002 | Grillo |

FOREIGN PATENT DOCUMENTS

| | | |
|---|---|---|
| WO | 88/04936 A1 | 7/1988 |
| WO | 92/07466 A1 | 5/1992 |
| WO | 94/11026 A2 | 5/1994 |
| WO | 00/29584 A1 | 5/2000 |
| WO | 0044788 A | 8/2000 |
| WO | 00/63403 A2 | 10/2000 |
| WO | 02056910 A1 | 7/2002 |
| WO | 03002607 A1 | 1/2003 |

OTHER PUBLICATIONS

Goldenberg D. M. et al. Blood, 113(5):1062-1070, Jan. 29, 2009.*
"An Extended Primer Set for PCR Amplification of Murine Kappa Variable Regions," *BioTechniques*, Aug. 1993, vol. 15, No. 2.
Ansel, et al., Pharmaceutical Dosage Forms and Drug Delivery Systems, Fifth Edition, 1990.
Appelbaum, "Radiolabeled Monoclonal Antibodies in the Treatment of Non-Hodgkin's Lymphoma," *Hematology/Oncology Clinics of North America*, Oct. 1991, pp. 1013-1025, vol. 5, No. 5, W.B. Saunders Company, Harcourt Brace Jovanovich, Inc., Philadelphia London Toronto Montreal Sydney Tokyo.
Frederick M. Ausubel, et al. (Eds.), "Current Protocols in Molecular Biology," 1994, vol. 1, John Wiley & Sons, Inc. & Current Protocols, Published simultaneously in Canada.
Baines, et al., "Purification of Immunoglobulin G (IgG)," *Methods in Molecular Biology*, 1992, pp. 79-105, vol. 10, chapter 8, Immunochemical Protocols, The Humana Press, Inc., Totowa, New Jersey.
Barnes, et al., "Advances in animal cell recombinant protein production: GS-NSO expression system," *Cytotechnology*, 2000, 109-123, 32, 2000 Kluwer Academic Publishers, Netherlands.

(Continued)

*Primary Examiner* — David J. Blanchard
(74) *Attorney, Agent, or Firm* — Rossi, Kimms & McDowell LLP

(57) ABSTRACT

The present invention provides substituted humanized, chimeric or human anti-CD20 antibodies or antigen binding fragments thereof and bispecific antibodies or fusion proteins comprising the substituted antibodies or antigen binding fragments thereof. The antibodies, fusion proteins or fragments are useful for treatment of B-cell disorders, such as B-cell malignancies and autoimmune diseases, as well as GVHD, organ transplant rejection, and hemolytic anemia and cryoglobulinemia. Amino acid substitutions, particularly substitution of an aspartate residue at Kabat position 101 of CDR3 $V_H$ (CDRH3), result in improved therapeutic properties, such as decreased dissociation rates, improved CDC activity, improved apoptosis, improved B-cell depletion and improved therapeutic efficacy at very low dosages. Veltuzumab, a humanized anti-CD20 antibody that incorporates such sequence variations, exhibits improved therapeutic efficacy compared to similar antibodies of different CDRH3 sequence, allowing therapeutic effect at dosages as low as 200 mg or less, more preferably 100 mg or less, more preferably 80 mg or less, more preferably 50 mg or less, most preferably 30 mg or less of naked antibody when administered i.v. or s.c.

19 Claims, 17 Drawing Sheets

OTHER PUBLICATIONS

Bird, et al., "Single chain antibody variable regions," *Tibtech*, Apr. 1991, pp. 132-137, vol. 9, Elsevier Science Publishers Ltd., United Kingdom.

Caron, et al., "*Brief Definitive Report* Engineered Humanized Dimeric Forms of IgG Are More Effective Antibodies," *J. Exp. Med.*, Oct. 1992, pp. 1191-1195, vol. 176, The Rockefeller University Press.

Carter, et al., "Humanization of an anti-p185[HER2] antibody for human cancer therapy," *Proc. Natl. Acad. Sci. USA*, Immunology, May 1992, pp. 4285-4289, vol. 89.

Cochlovius, et al., "*Advances in Brief* Cure of Burkitt's Lymphoma in Severe Combined Immunodeficiency Mice by T Cells, Tetravalent CD3 ×CD19 Tandem Diabody, and CD28 Costimulation[1]," *Cancer Research*, Aug. 15, 2000, pp. 4336-4341, vol. 60, Germany.

Colman, "Production of therapeutic proteins in the milk of transgenic livestock," *Biochem. Soc. Symp.*, pp. 141-147, 63, Portland Press, United Kingdom, 1996.

Coloma, et al., "Design and production of novel tetravalent bispecific antibodies," *Nature Biotechnology*, Feb. 1997, pp. 159-163, vol. 15.

Courtenay-Luck, "Genetic manipulation of monoclonal antibodies" *Genetic manipulation of monoclonal antibodies*, 1995, pp. 166-179, First published University Press, Cambridge, United Kingdom, Press Syndicate of the University of Cambridge, New York.

Devesa, et al., "Cancer Incidence and Mortality Trends Among Whites in the United States, 1947-48," *JNCi*, Oct. 1987, pp. 701-770, vol. 79, No. 4, National Cancer Institute, U.S. Department of Health and Human Services, Public Health Service, National Institutes of Health.

Eary, et al., "Imaging and Treatment of B-Cell Lymphoma," *The Journal of Nuclear Medicine*, Aug. 1990, pp. 1257-1268, vol. 31, No. 8, The Official Publication of The Society of Nuclear Medicine, Inc.

Fitzgerald, et al., "Improved tumour targeting by disulphide stabilized diabodies expressed in *Pichia pastoris*," *Protein Engineering*, 1997, pp. 1221-1225, vol. 10, No. 10, Oxford University Press, United Kingdom.

Foon, et al., "Chronic Lymphocytic Leukemia: New Insights into Biology and Therapy," *Annals of Internal Medicine*, Oct. 1, 1990, pp. 525-539, vol. 113, No. 7, Published twice monthly by the American College of Physicians.

Freedman, "Immunobiology of Chronic Lymphocytic Leukemia," *Hematology/Oncology Clinics of North America*, Apr. 1990, vol. 4, No. 2, W.B. Saunders Company, Harcourt Brace Jovanovich, Inc., Philadelphia London Toronto Montreal Sydney Tokyo.

Freedman, et al., "XXXVI-10 Non-Hodgkin's Lymphomas," *CancerMedicine—Third Edition*, 1993, pp. 2028-2068, vol. 2, Lea & Febiger, Philadelphia, London.

Gennaro, "Remington: Practice of," 19th Edition, *The Science and Pharmacy*, 1995, Mack Publishing Company, United States.

Ghetie, et al., "Homodimerization of tumor-reactive monoclonal antibodies markedly increases their ability to induce growth arrest or apoptosis of tumor cells," Immunology, *Proc. Natl. Acad. Sci. USA*, Jul. 1997, pp. 7509-7514, vol. 94, The National Academy of Sciences, USA.

Ghetie, et al., "Homodimers but not monomers of Rituxan (chimeric anti-CD20) induce apoptosis in human B-lymphoma cells and synergize with a chemotherapeutic agent and an immunotoxin," *Blood*, Mar. 1, 2001, pp. 1392-1396, vol. 97, No. 5, The American Society of Hematology, USA.

Ghetie, et al., "Evaluation of Ricin a Chain-containing Immunotoxins Directed against CD19 and CD22 Antigens on Normal and Malignant Human B-Cells as Potential Reagents for in Vivo Therapy[1]," *Cancer Research*, 1988, pp. 2610-2617, vol. 48, No. 9.

Gillies, et al., "High-level expression of chimeric antibodies using adapted cDNA variable region cassettes," *Journal of Immunological Methods*, 1989, pp. 191-202, vol. 125, Elsevier Science Publishers B.V. (Biomedical Division), USA.

Goldenberg, "New Developments in Monoclonal Antibodies for Cancer Detection and Therapy," *CA-A Cancer Journal for Clinicians*, Jan./Feb. 1994, pp. 43-64, vol. 44, No. 1, Ortho Biotech, Inc., USA.

Goldenberg, et al., "Targeting, Dosimetry, and Radioimmunotherapy of B-Cell Lymphomas With Iodine-131-Labeled LL2 Monoclonal Antibody," *Journal of Clinical Oncology*, Apr. 1991, pp. 548-564, vol. 9, No. 4, W.B. Saunders Company, Harcourt Brace Jovanovich, Inc., Philadelphia London Toronto Montreal Sydney Tokyo.

Goodman, et al., "The Pharmacological Basis of Therapeutics," Fifth Edition, 1975, MacMillan Publishing Co., Inc. USA.

Goodman, et al., "New Perspectives on the Approach to Chronic Lymphocytic Leukemia," *Leukemia and Lymphoma*, 1996, pp. 1-40, vol. 22, Nos. 1 / 2, Harwood Acedemic Publishers, The Netherlands.

Green, et al., "Antigen-specific human monoclonal antibodies from mice engineered with human Ig heavy and light chain YACs," *Nature Genetics*, May 1994, pp. 13-21, vol. 7, No. 1, USA.

Hasan, et al., "Laser-Induced Selective Cytotoxicity Using Monoclonal Antibody-Chromophore Conjugates," *Immunity to Cancer*, 1989, pp. 471-477, vol. II, Alan R. Liss, Inc., USA.

Hekman, et al., "Initial experience with treatment of human B cell lymphoma with anti-CD19 monoclonal antibody," *Cancer Immunology Immunotherapy*, 1991, pp. 364-372, vol. 32, No. 6, Springer-Verlag, The Netherlands.

Hugues, et al., Conjugation of methotrexate to poly(L-lysine) increases drug transport and overcomes drug resistance in cultured cells, *Proc. Natl. Acad. Sci. USA*, Aug. 1978, pp. 3867-3870, vol. 75.

Huse, et al., "Generation of a Large Combinatorial Library of the Immunoglobulin Repertoire in Phage Lambda," *Research Article*, Dec. 8, 1989, pp. 1275-1281, vol. 246.

Johnson, et al., "Human antibody engineering," *Current Opinion in Structural Biology*, 1993, pp. 564-571, vol. 3, Cambridge Antibody Technology Ltd., United Kingdom.

Jones, et al., "Replacing the complementarity-determining regions in a human antibody with those from a mouse," *Nature*, May 29, 1986, pp. 522-525, vol. 321, No. 6069, Laboratory of Molecular Biology, Medical Research Council, United Kingdom.

Giulio Jori, et al., (Eds.), "Photodynamic Therapy of Tumors and Other Diseases," *Lectures/paper given at the meeting hold at Alghero* (Italy), May 1-4, 1985.

Kaminski, et al., "Radioimmunotherapy of B-Cell Lymphoma with [$^{131}$I] Anti-B1 (Anti-CD20) Antibody," *The New England Journal of Medicine*, Aug. 12, 1993, pp. 459-465, vol. 329, No. 7, Massachusetts Medical Society, USA.

"Continuous cultures of fused cells secreting antibody of predefined specificity," *Nature*, Aug. 7, 1975, pp. 495-497, vol. 256, No. 5517, MRC Laboratory of Molecular Biology, United Kingdom.

Larrick, et al., "PCR Amplification of Antibody Genes," *Methods*, Apr. 1991, pp. 106-110, vol. 2, No. 2, Academic Press, Inc., Harcourt Brace Jovanovich, Publishers, San Diego New York Boston London Sydney Tokyo Toronto.

Leung, et al., "Chimerization of LL2, a Rapidly Internalizing Antibody Specific for B Cell Lymphoma," *Hybridoma*, Dec. 1994, pp. 469-478, vol. 13, No. 6, Mary Ann Liebert, Inc., New Jersey, USA.

Leung, et al., "Engineering a Unique Glycosylation Site for Site-Specific Conjugation of Haptens to Antibody Fragments," *The Journal of Immunology*, Jun. 1, 1995, pp. 5919-5928, vol. 154, No. 11, The Amercian Association of Immunologists, USA.

Leung, et al., "Construction and Characterization of a Humanized, Internalizing, B-Cell (CD22)-Specific, Leukemia/Lymphoma Antibody, LL2," *Molecular Immunology*, 1995, pp. 1413-1427, vol. 32, No. 17/18, Elsevier Science Ltd., Great Britain.

Liu, et al.,"Production of a Mouse-Human Chimeric Monoclonal Antibody to CD20 with Potent Fc-Dependent Biologic Activity," *The Journal of Immunology*, Nov. 15, 1987, pp. 3521-3528, vol. 139, No. 10, The American Association of Immunologists, USA.

Lonberg, et al., "Antigen-specific human antibodies from mice comprising four distinct genetic modifications," *Nature*, Apr. 28, 1994, pp. 656-859, vol. 368.

Longo, "Immunotherapy for non-Hodgkin's Lymphoma," *Current Opinion in Oncology*, Sep. 1996, pp. 353-359, vol. 8, No. 5, Rapid Science Publishers, USA.

Losman, et al., Generation of a High-Producing Clone of a Humanized Anti-B-Cell Lymphoma Monoclonal Antibody (hLL2), *Cancer Supplement*, Dec. 15, 1997, pp. 2660-2666, vol. 80, No. 12, Published for the American Cancer Society by John Wiley & Sons, Inc., USA.

Majolino, et al., "High-dose cyclophosphamide, etoposide and BCNU (CVB) with autologous stem cell rescue in malignant lymphomas," *European Journal of Haematology*, Jul. 1993, pp. 18-24, vol. 51, No. 1.

Mew, et al., "Ability of Specific Monoclonal Antibodies and Conventional Antisera Conjugated to Hematoporphyrin to Label and Kill Selected Cell Lines Subsequent to Light Activation," *Cancer Research*, Sep. 1985, pp. 4380-4386, vol. 45.

McCafferty, et al., "Phage antibodies: filamentous phage displaying antibody variable domains," *Nature*, Dec. 6, 1990, pp. 552-554, vol. 348, No. 6301.

Mack, et al., "A small bispecific antibody construct expressed as a functional single-chain molecule with-high tumor cell cytotoxicity," *Proc. Natl. Acad. Sci. USA*, Jul. 1995, pp. 7021-7025, vol. 92.

Maloney, et al., "Phase I Clinical Trial Using Escalating Single-Dose Infusion of Chimeric Anti-CD20 Monoclonal Antibody (IDEC-C2B8) in Patients With Recurrent B-Cell Lymphoma," *Blood*, Oct. 15, 1994, pp. 2457-2466, vol. 84, No. 8.

Mendez, et al, "Functional transplant of megabase human immunoglobulin loci recapitulates human antibody response in mice," *Nature Genetics*, Feb. 15, 1997, pp. 146-156, vol. 15, No. 2.

Mew, et al., "Photoimmunotherapy: Treatment of Animal Tumors with Tumor-Specific Monoclonal Antibody-Hematoporphyrin Conjugates," *The Journal of Immunology*, Mar. 1983, pp. 1473-1477, vol. 130, No. 3.

Nisonoff, et al., "Separation of Univalent Fragments from the Bivalent Rabbit Antibody Molecule by Reduction of Disulfide Bonds," *Archives of Biochemistry and Biophysics*, 1960, pp. 130-244, vol. 89, No. 2.

Orlandi, et al., "Cloning immunoglobulin variable domains for expression by the polymerase chain reaction," *Proc. Ned. Acad. Sci. USA*, May 1989, pp. 3833-3837, vol. 86.

Oseroff, et al., "Strategies for selective cancer photochemotherapy: antibody-targeted and selective carcinoma cell photolysis," *Photochemistry and Photobiology*, 1987, pp. 8396, vol. 46, No. 1.

Oseroff, et al., Antibody-targeted photolysis: Selective photodestruction of human T-cell leukemia cells using monoclonal antibody-chlorin $e_6$ conjugates, *Proc. Natl. Acad. Sci, USA*, Nov. 1986, pp. 8744-8748, vol. 83.

Pastan, et al., "Immunotoxins," *Cell*, Dec. 5, 1986, pp. 641-648, vol. 47, No. 5.

Pélegrin, et al., "Antibody-Fluorescein Conjugates for Photoimmunodiagnosis of Human Colon Carcinoma in Nude Mice," *Cancer*, May 15, 1991, pp. 2529-2537, vol. 67, No. 10.

Porter, "The Hydrolysis of Rabbit γ-Globulin and Antibodies with Crystalline Papain," *The Biochemical Journal*, Sep. 1959, pp. 119-126, vol. 73, No. 1.

Press, et al., "Radiolabeled-Antibody Therapy of B-Cell Lymphoma With Autologous Bone Marrow Support," Oct. 21, 1993, pp. 1219-1224, vol. 329, No. 17.

Press, et al., "Phase II trial of $^{131}$I-B1 (anti-CD20) antibody therapy with autologous stem cell transplanation for relapsed B cell lymphomas," Aug. 5, 1995, pp. 336-340, vol. 346, No. 8791.

Press, et al., "Monoclonal Antibody 1F5 (Anti-CD20) Serotherapy of Human B Cell Lymphomas," *Blood*, Feb. 1987, pp. 584-591, vol. 69, No. 2.

Press, et al., "Treatment of Refractory Non-Hodgkin's Lymphoma With Radiolabeled MB-1 (Anti-CD37) Antibody," *Journal of Clinical Oncology*, Aug. 1989, pp. 1027-1038, vol. 7, No. 8.

Price, "Production and characterization of synthetic peptide-derived antibodies," pp. 60-85, "from Monoclonal Antibodies: production; enggineering, and clinical application" Cambridge University Press, 1995.

Raag, et al., "Single-chain Fvs," *The FASEB Journal*, Jan. 1995, pp. 73-80, vol. 9.

Riechmann, et al., "Reshaping human antibodies for therapy," *Nature*, Mar. 1988, pp. 323-327, vol. 332, No. 6162.

Robinson, et al., "Chimeric mouse-human anti-carcinoma antibodies that mediate different anti-tumor cell biological activities," *Human Antibodies and Hybridomas*, Apr. 1991, pp. 84-93, vol. 2, No. 2.

Saltzman, et al., "Transport rates of proteins in porous materials with known microgeometry," *Biophysical Journal*, Jan. 1989, pp. 183-171, vol. 55, No. 1, Published for the Biophysical Society by the Rockefeller University Press, USA.

Sambrook, et al., "Molecular Cloning," *A Laboratory Manual*, Second Edition, 1989, Cold Spring Harbor Laboratory Press, USA.

Sanger, et al., "DNA sequencing with chain-terminating Inhibitors," *Proc. Natl. Acad. Sci USA*, Biochemistry, Dec. 1977, pp. 5463-5467, vol. 74, No. 12, Medical Research Council Laboratory of Molecular Biology, England.

Shan, et al., "Signaling events involved in anti-CD20-induced apoptosis of malignant human B cells," *Cancer Immunology Immunother*, 2000, pp. 673-683, Springer-Verlag, OW Press, USA.

Sherwood, et al., "Controlled Antibody Delivery Systems," *Biotechnology*, Nov. 1992, pp. 1446-1449, vol. 10.

Shih, et al., "A Fluorouridine-Anti-Cea Immunoconjugate Is Therapeutically Effective In A Human Colonic Cancer Xenograft Model," *International Journal of Cancer*, Dec. 15, 1990, pp. 1101-1106, vol. 46, No. 6, Publication of the International Union Against Cancer, Wiley-Liss, Inc., USA.

Shih, et al., "Site-Specific Linkage of Methotrexate to Monoclonal Antibodies Using an Intermediate Carrier," *International Journal of Cancer*, May 15, 1988, pp. 832-839, vol. 41, No. 5, Publication of the International Union Against Cancer, Alan R. Liss, Inc., USA.

Shopes, "A Genetically Engineered Human IgG Mutant With Enhanced Cytolytic Activity," *The Journal of Immunology*, May 1, 1992, pp. 2918-2922, vol. 148, No. 9, The American Association of Immunologists, USA.

Singer, et al., "Optimal Humanization of 1B4, an Anti-CD18 Murine Monoclonal Antibody, Is Achieved by Correct Choice of Human V-Region Framework Sequences," *The Journal of Immunology*, Apr. 1, 1993, pp. 2844-2857, vol. 150, No. 7, The American Association of Immunologists, USA.

Tatsuta, et al., "Diagnosis of Gastric Cancers With Fluorescein-Labeled Monoclonal Antibodies to Carcinoembryonic Antigen," *Lasers in Surgery and Medicine*, 1989, pp. 422-426, vol. 9, No. 4, Alan R. Liss, Inc., USA.

Taylor, et al., "Human immunoglobulin transgenes undergo rearrangement, somatic mutation and class switching in mice that lack endogenous Igm," *International Immunology*, 1994, pp. 579-591, vol. 6, No. 4, Oxford University Press, USA.

Tempest, et al., "Reshaping a Human Monoclonal Antibody to Inhibit Human Respiratory Syncytial Virus Infection in Vivo," *Bio/Technology*, Mar. 1991, pp. 266-271, vol. 9.

Upeslacis, et al., "Modification of Antibodies by Chemical Methods," *Monoclonal Antibodies: Principles and Applications*, 1995, pp. 187-230, Chapter 4, Wiley-Liss, Inc., USA.

Van Den Bergh, "Light and porphyrins in cancer therapy," *Chemistry in Britain*, May 1986, pp. 430-439.

Verhoeyen, et al., "Reshaping Human Antibodies: Grafting an Antilysozyme Activity," *Science*, Mar. 25, 1988, pp. 1534-1536, vol. 239, Medical Research Courter Laboratory of Molecular Biology, England.

Ward, et al., "Genetic Manipulation and Expression of Antibodies," *Monoclonal Antibodies: Principles and Applications*, 1995, pp. 137-185, Chapter 3, Wiley-Liss, Inc., USA.

Werner, et al., "Appropriate Mammalian Expression Systems for Biopharmaceuticals," *Arzneimittel Forschung Drug Research*, Aug. 1998, pp. 789-880, vol. 48, Germany.

Wong, "Chemistry of Protein Conjugation and Cross-Linking" 1991, CRC Press, Inc., USA.

Yu, et al."Peptide-Antibody Conjugates for Tumour Therapy: A MHC-Class-II-Restricted Tetanus Toxin Peptide Coupled to an Anti-Ig Light Chain Antibody Can Induce Cytotoxic Lysis or a Human B-Cell Lymphoma by Specific CD4 T Cells," *International Journal of Cancer*, Jan. 15, 1994, pp. 244-248, vol. 56, No. 2, Publication of the International Union Against Cancer, Wiley-Liss, Inc., USA.

Maloney et al., "Newer Treatments for Non-Hodgkin's Lymphoma: Monoclonal Antibodies," Onocology (Oct. 1998), Supplement No. 8, pp. 63-76, XP 002935647, ISSN: 0030-2414.

Gopal et al., "Clinical applications of antiCD20 antibodies," Journal of Laboratory and Clinical Medicine (1999), vol. 134, No. 5, pp. 445-450, XP 002935646, ISSN: 002-2143.

Longo D. L., Current Opinion in Immunology, 8:353-359, 1994.

Kazkaz et al., Current Opinion in Pharmacology, 4:398-402, 2004.

Gorman et al., Arthritis Research therapy, 5(Suppl 4):S17-S21, 2003.
Eisenberg et al., Clinical Immunology, 117:207-213, 2005.
William E. Paul, Fundamental Immunology, 3rd Edition, pp. 292-295, 1993.
Rudikoff et al., Proc. Natl. Acad. Sci. USA, 79:1979-1983, 1982.
Extended International Search Report of Application No. PCT/GB 03/00665 dated Sep. 15, 2004 corresponding to U.S. Appl. No. 11/534,103.

Shan, Damining et al., "Characterization of scFv-Ig Constructs Generated from Anti-CD20 mAb 1F5 Using Linker Peptides of Varying Lengths", The American Association of Immunologists, 1999; pp. 1-7.
Tesch et al; "Treatment of patients with malignant lymphomas with monoclonal antibodies"; Bone Marrow Transplantation (2000) 25, Suppl. 2, pp. S50-S53; 2000 Macmillan Publishers Ltd.

* cited by examiner cA20Vk

```
GACATCCAGCTGACCCAGTCTCCAGCAATCCTGTCTGCATCTCCAGGGGAGAAGGTCACAATGACTTGCAGGGCCAGCTCAAGTGTAAGT          90
 1                     10                      20          27 29 30
 D  I  Q  L  T  Q  S  P  A  I  L  S  A  S  P  G  E  K  V  T  M  T  C  R  A  S  S  S  V  S
                                                                      CDR1

TACATCCACTGGTTCCAGCAGAAGCCAGGATCCTCCCCCAAACCTGGATTTATGCCACATCCAACCTGGCTTCTGGAGTCCCTGTTCGC          180
                       40                      50                      60
 Y  I  H  W  F  Q  Q  K  P  G  S  S  P  K  P  W  I  Y  A  T  S  N  L  A  S  G  V  P  V  R
                                                   CDR2

TTCAGTGGCAGTGGGTCTGGGACTTCTTACTCTCTCACAATCAGCAGAGTGGAAGCTGAAGATGCTGCCACTTATTACTGCCAGCAGTGG          270
                       70                      80                      90
 F  S  G  S  G  S  G  T  S  Y  S  L  T  I  S  R  V  E  A  E  D  A  A  T  Y  Y  C  Q  Q  W

ACTAGTAACCCACCCACGTTCGGAGGGGGGACCAAGCTGGAGATCAAA                                                   318
                       100         107
 T  S  N  P  P  T  F  G  G  G  T  K  L  E  I  K
 CDR3
```

FIG. 1A cA20VH

```
CAGGTCCAACTGCAGCAGCCTGGGGCTGAGCTGGTGAAGCCTGGGGCCTCAGTGAAGATGTCCTGCAAGGCTTCTGGCTACACATTTACC   90
  1                    10                    20                    30
  Q  V  Q  L  Q  Q  P  G  A  E  L  V  K  P  G  A  S  V  K  M  S  C  K  A  S  G  Y  T  F  T

AGTTACAATATGCACTGGGTAAAACAGACACCTGGTCGGGGCCTGGAATGGATTGGAGCTATTTATCCCGGAAATGGTGATACTTCCTAC  180
                      40                    50           52 A
  S  Y  N  M  H  W  V  K  Q  T  P  G  R  G  L  E  W  I  G  A  I  Y  P  G  N  G  D  T  S  Y
           CDR1                                              CDR2

AATCAGAAGTTCAAAGGCAAGGCCACATTGACTGCAGACAAATCCTCCAGCACAGCCTACATGCAGCTGAGCTCTGAGGAC  270
 60                    70                    80  82 A B C
  N  Q  K  F  K  G  K  A  T  L  T  A  D  K  S  S  S  T  A  Y  M  Q  L  S  S  L  T  S  E  D

TCTGCGGTCTATTACTGTGCAAGATCGACTTACTACGGCGGTGACTGGTACTTCGATGTCTGGGGCCAAGGGACCACGGTCACCGTCTCC  360
                     90              100 A  B  C  D        110
  S  A  V  Y  Y  C  A  R  S  T  Y  Y  G  G  D  W  Y  F  D  V  W  G  Q  G  T  T  V  T  V  S
                        CDR3

TCA  363
113
 S
```

*FIG. 1B*

```
                                                                                                                    -91
XbaI                                                                                                                -5
tctagacacacaggacctcaccATGGGATGGAGCTGTATCATCCTCTTCTTGGTAGCAACAGCTACAggta
                      M   G   W   S   C   I   I   L   F   L   V   A   T   A   T AggggctcacagtagcaggcttgaggtctggacatatatgggtgacaatgacatccacttgctttctctccacAGGTGTCCACTCC          -1
                                                                         G  V  H  S            -1

PvuII                                                                                90
GACATCCAGCTGACCCAGTCTCCATCATCCCTGAGCGCATCTGTTGGAGATAGGGTCACTATGACTTGTAGGGCCAGCTCAAGTGTAAGT      30
 D  I  Q  L  T  Q  S  P  S  S  L  S  A  S  V  G  D  R  V  T  M  T  C  R  A  S  S  V  S
                                                                            CDR1

TACATCCACTGGTTCCAGCAGAAACCAGGGAAAGCACCTAAACCCTGGATTTATGCAACTTCGAACCTGGCTTCTGGTGTCCCTGTCCGA     180
 Y  I  H  W  F  Q  Q  K  P  G  K  A  P  K  P  W  I  Y  A  T  S  N  L  A  S  G  V  P  V  R      61
                                                             CDR2

TTCTCTGGCAGCGGATCTGGGACAGATTACACTTTCACCATCAGCTCTCTTCAACCAGAAGACATTGCAACATATTATTGTCAGCAGTGG    270
 F  S  G  S  G  S  G  T  D  Y  T  F  T  I  S  S  L  Q  P  E  D  I  A  T  Y  Y  C  Q  Q  W      91

BglII/BclI                             BamHI
ACTAGTAACCCACCACGTTCGGTGGAGGGACCAAGCTGGAGATCAAACgtgagtagagaatttaaactttgcttcctcagttggatcc       357
 T  S  N  P  P  T  F  G  G  G  T  K  L  E  I  K                                                107
  CDR3

FIG. 2A
```

```
                                                                                          XhoI
                                                                                          ctcgagcacacaggacctcaccAATGGGATGGAGCTGTATCATCCTCTTCTTGGTAGCAACAGCTAcaggta    -91
                                                                                                            M  G  W  S  C  I  I  L  F  L  V  A  T                   -5

AgggggctcacagtagcaggcttcaggtctgagacatatatggtgacaatgacatccactttgccttctctcccCAGGTGTCCACTCC                                                                            -1
                                                                        G  V  H  S                                                                                  -1
PstI
CAGGTCCAACTGCAGCAATCAGGGGCTGAAGTCAAGAAACCTGGGTCATCGGTGAAGGTCTCCTGCAAGGCTTCTGGCTACACCTTTACT                                                                         90
 Q  V  Q  L  Q  Q  S  G  A  E  V  K  K  P  G  S  S  V  K  V  S  C  K  A  S  G  Y  T  F  T                                                                          30

AGTTACAATATGCACTGGGTCAAGCAGGCACCTGGACAGGGTCTTGAATGGATTGGAGCTATTTATCCCGGAAATGGTGATACTTCCTAC                                                                         180
 S  Y  N  M  H  W  V  K  Q  A  P  G  Q  G  L  E  W  I  G  A  I  Y  P  G  N  G  D  T  S  Y                                                                          59
 ───────────                                              ──────────────────────────────
     CDR1                                                              CDR2

AATCAGAAGTTCAAGGGTAAAGCCACACTGACTGCCGACGAATCCACCAATACAGCCTACATGGAGCTGAGCAGCCTGAGGTCTGAGGAC                                                                         270
 N  Q  K  F  K  G  K  A  T  L  T  A  D  E  S  T  N  T  A  Y  M  E  L  S  S  L  R  S  E  D                                                                          86
 ─────────────
                                                                        BstEII
ACGGCATTTTATTACTGTGCAAGATCGACTTACTACGGCGGTGACTGGTACTTCGATGTCTGGGGCCAAGGCACCACGGTCACCGTCTCC                                                                         360
 T  A  F  Y  Y  C  A  R  S  T  Y  Y  G  G  D  W  Y  F  D  V  W  G  Q  G  T  T  V  T  V  S                                                                          112
              ──────────────────────────────────────────
                                  CDR3

TCAGgtgagtccttacaacctctctcttctattcagcttaaatagatttactgcattgtgttggggggaaatgtgtgtatctgaatttc                                                                          450
 S                                                                                                                                                                  113 aggtcatgaaggactagggacaccttgggagtcagaaagggtcattgggagcccggggctgatgcagacagacatcctcagctccagact                                                                         540

BamHI
tcatggccagagaggattttataggatcc                                                                                                                                       565
```

```
              1         10        20         30           40
cA20VH    QVQLQQPGAELVKPGASVKMSCKASGYTFTSYNMHWVKQT
c2B8VH    ........................................
hA20VH    ......S...VK...S...V...............A 50  52 A     60         70
cA20VH    PGRGLEWIGAIYPGNGDTSYNQKFKGKATLTADKSSSTAY
c2B8VH    ........................................
hA20VH    ..Q...............................E.TN...

80 82 A B C        90      100 A B C D    110  113
cA20VH    MQLSSLTSEDSAVYYCARSTYYGGDWYFDVWGQGTTVTVSS
c2B8VH    ..............................N.........
hA20VH    .E....R...T.F.............................S
```

FIG. 3B

```
              1         10         20      28  30        40
cA20Vk    DIQLTQSPAILSASPGEKVTMTCRAS.SSVSYIHWFQQKP
c2B8Vk    Q.V.S...................................
hA20Vk    ........SS....V.DR......................

50        60         70         80
cA20Vk    GSSPKPWIYATSNLASGVPVRFSGSGSGTSYSLTISRVEA
c2B8Vk    ........................................
hA20Vk    .KA.......................D.TF...SLQP 90        100     108
cA20Vk    EDAATYYCQQWTSNPPTFGGGTKLEIK
c2B8Vk    ...........................
hA20Vk    ..I........................
```

| Treatment | Mean | | | |
|---|---|---|---|---|
| | Estimate | Std. Error | 95% Confidence Interval | |
| | | | Lower Bound | Upper Bound |
| Untreated | 22.100 | .575 | 20.972 | 23.228 |
| Rituximab | 47.913 | 4.362 | 39.364 | 56.461 |
| Veltuzumab (hA20) | 78.933 | 5.724 | 67.714 | 90.153 |

```
                        SEQUENCE LISTING

<160> NUMBER OF SEQ ID NOS: 33

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Ser Ser Val Ser Tyr Ile His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Thr Ser Asn Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Trp Thr Ser Asn Pro Pro Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Asn Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ile Tyr Pro Gly Asn Gly Asp Thr Ser Tyr Asn Gln Lys Phe Lys
1               5                   10                  15

Gly
```

```
<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Thr Tyr Tyr Gly Gly Asp Trp Tyr Phe Asp Val
1               5                   10

<210> SEQ ID NO 7
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(318)

<400> SEQUENCE: 7 gac atc cag ctg acc cag tct cca gca atc ctg tct gca tct cca ggg      48
Asp Ile Gln Leu Thr Gln Ser Pro Ala Ile Leu Ser Ala Ser Pro Gly
1               5                   10                  15 gag aag gtc aca atg act tgc agg gcc agc tca agt gta agt tac atc      96
Glu Lys Val Thr Met Thr Cys Arg Ala Ser Ser Ser Val Ser Tyr Ile
            20                  25                  30 cac tgg ttc cag cag aag cca gga tcc tcc ccc aaa ccc tgg att tat     144
His Trp Phe Gln Gln Lys Pro Gly Ser Ser Pro Lys Pro Trp Ile Tyr
        35                  40                  45 gcc aca tcc aac ctg gct tct gga gtc cct gtt cgc ttc agt ggc agt     192
Ala Thr Ser Asn Leu Ala Ser Gly Val Pro Val Arg Phe Ser Gly Ser
    50                  55                  60 ggg tct ggg act tct tac tct ctc aca atc agc aga gtg gag gct gaa     240
Gly Ser Gly Thr Ser Tyr Ser Leu Thr Ile Ser Arg Val Glu Ala Glu
65                  70                  75                  80 gat gct gcc act tat tac tgc cag cag tgg act agt aac cca ccc acg     288
Asp Ala Ala Thr Tyr Tyr Cys Gln Gln Trp Thr Ser Asn Pro Pro Thr
                85                  90                  95 ttc gga ggg ggg acc aag ctg gag atc aaa                             318
Phe Gly Gly Gly Thr Lys Leu Glu Ile Lys
            100                 105

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80
```

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 9
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 9 cag gtc caa ctg cag cag cct ggg gct gag ctg gtg aag cct ggg gcc        48
Gln Val Gln Leu Gln Gln Pro Gly Ala Glu Leu Val Lys Pro Gly Ala
1               5                   10                  15 tca gtg aag atg tcc tgc aag gct tct ggc tac aca ttt acc agt tac        96
Ser Val Lys Met Ser Cys Lys Ala Ser Gly Tyr Thr Phe Thr Ser Tyr
            20                  25                  30 aat atg cac tgg gta aaa cag aca cct ggt cgg ggc ctg gaa tgg att       144
Asn Met His Trp Val Lys Gln Thr Pro Gly Arg Gly Leu Glu Trp Ile
        35                  40                  45 gga gct att tat ccc gga aat ggt gat act tcc tac aat cag aag ttc       192
Gly Ala Ile Tyr Pro Gly Asn Gly Asp Thr Ser Tyr Asn Gln Lys Phe
    50                  55                  60 aaa ggc aag gcc aca ttg act gca gac aaa tcc tcc agc aca gcc tac       240
Lys Gly Lys Ala Thr Leu Thr Ala Asp Lys Ser Ser Ser Thr Ala Tyr
65                  70                  75                  80 atg cag ctc agc agc ctg aca tct gag gac tct gcg gtc tat tac tgt       288
Met Gln Leu Ser Ser Leu Thr Ser Glu Asp Ser Ala Val Tyr Tyr Cys
                85                  90                  95 gca aga tcg act tac tac ggc ggt gac tgg tac ttc gat gtc tgg ggc       336
Ala Arg Ser Thr Tyr Tyr Gly Gly Asp Trp Tyr Phe Asp Val Trp Gly
            100                 105                 110 caa ggg acc acg gtc acc gtc tcc tca                                   363
Gln Gly Thr Thr Val Thr Val Ser Ser
        115                 120

<210> SEQ ID NO 10
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys

```
                          85                  90                  95
Ala Arg Ser Thr Tyr Tyr Gly Gly Asp Trp Tyr Phe Asp Val Trp Gly
            100                 105                 110

Gln Gly Thr Thr Val Thr Val Ser Ser
        115                 120

<210> SEQ ID NO 11
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(64)
<220> FEATURE:
<221> NAME/KEY: sig_peptide
<222> LOCATION: (21)..(64)
<220> FEATURE:
<221> NAME/KEY: CDS
<222> LOCATION: (147)..(477)
<220> FEATURE:
<221> NAME/KEY: sig_peptide
<222> LOCATION: (147)..(159)
<220> FEATURE:
<221> NAME/KEY: mat_peptide
<222> LOCATION: (160)..(477)

<400> SEQUENCE: 11
tctagacaca ggacctcacc atg gga tgg agc tgt atc atc ctc ttc ttg gta       53
                     Met Gly Trp Ser Cys Ile Ile Leu Phe Leu Val
                         -15                 -10 gca aca gct ac  aggtaaggggg ctcacagtag caggcttgag gtctggacat           104
Ala Thr Ala Thr
         -5 atatatgggt gacaatgaca tccactttgc ctttctctcc ac a ggt gtc cac tcc       159
                                             Gly Val His Ser
                                                           -1 gac atc cag ctg acc cag tct cca tca tct ctg agc gca tct gtt gga       207
Asp Ile Gln Leu Thr Gln Ser Pro Ser Ser Leu Ser Ala Ser Val Gly
1               5                   10                  15 gat agg gtc act atg act tgt agg gcc agc tca agt gta agt tac atc       255
Asp Arg Val Thr Met Thr Cys Arg Ala Ser Ser Ser Val Ser Tyr Ile
                20                  25                  30 cac tgg ttc cag cag aaa cca ggg aaa gca cct aaa ccc tgg att tat       303
His Trp Phe Gln Gln Lys Pro Gly Lys Ala Pro Lys Pro Trp Ile Tyr
            35                  40                  45 gcc act tcg aac ctg gct tct ggt gtc cct gtc cga ttc tct ggc agc       351
Ala Thr Ser Asn Leu Ala Ser Gly Val Pro Val Arg Phe Ser Gly Ser
        50                  55                  60 gga tct ggg aca gat tac act ttc acc atc agc tct ctt caa cca gaa       399
Gly Ser Gly Thr Asp Tyr Thr Phe Thr Ile Ser Ser Leu Gln Pro Glu
65                  70                  75                  80 gac att gca aca tat tat tgt cag cag tgg act agt aac cca ccc acg       447
Asp Ile Ala Thr Tyr Tyr Cys Gln Gln Trp Thr Ser Asn Pro Pro Thr
                85                  90                  95 ttc ggt gga ggg acc aag ctg gag atc aaa cgtgagtaga atttaaactt        497
Phe Gly Gly Gly Thr Lys Leu Glu Ile Lys
            100                 105 tgcttcctca gttggatcc                                                  516

<210> SEQ ID NO 12
<211> LENGTH: 125
<212> TYPE: PRT
```

<210> ORGANISM: Artificial Sequence
<220> FEATURE:
<223> OTHER INFORMATION: Description of Artificial Sequence: Synthetic polypeptide

<400> SEQUENCE: 12

```
Met Gly Trp Ser Cys Ile Ile Leu Phe Leu Val Ala Thr Ala Thr Gly
            -15                 -10                 -5
Val His Ser Asp Ile Gln Leu Thr Gln Ser Pro Ser Ser Leu Ser Ala
     -1   1               5                  10
Ser Val Gly Asp Arg Val Thr Met Thr Cys Arg Ala Ser Ser Ser Val
         15                  20                  25
Ser Tyr Ile His Trp Phe Gln Gln Lys Pro Gly Lys Ala Pro Lys Pro
 30                  35                  40                  45
Trp Ile Tyr Ala Thr Ser Asn Leu Ala Ser Gly Val Pro Val Arg Phe
                 50                  55                  60
Ser Gly Ser Gly Ser Gly Thr Asp Tyr Thr Phe Thr Ile Ser Ser Leu
                 65                  70                  75
Gln Pro Glu Asp Ile Ala Thr Tyr Tyr Cys Gln Gln Trp Thr Ser Asn
             80                  85                  90
Pro Pro Thr Phe Gly Gly Gly Thr Lys Leu Glu Ile Lys
         95                 100                 105
```

<210> SEQ ID NO 13
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (23)..(66)
<220> FEATURE:
<221> NAME/KEY: sig_peptide
<222> LOCATION: (23)..(66)
<220> FEATURE:
<221> NAME/KEY: CDS
<222> LOCATION: (149)..(524)
<220> FEATURE:
<221> NAME/KEY: sig_peptide
<222> LOCATION: (149)..(161)
<220> FEATURE:
<221> NAME/KEY: mat_peptide
<222> LOCATION: (162)..(524)

<400> SEQUENCE: 13

```
ctcgagcaca caggacctca cc atg gga tgg agc tgt atc atc ctc ttc ttg        52
                        Met Gly Trp Ser Cys Ile Ile Leu Phe Leu
                            -15                 -10 gta gca aca gct ac   aggtaaggggg ctcacagtag caggcttgag gtctggacat       106
Val Ala Thr Ala Thr
                -5 atatatgggt gacaatgaca tccactttgc ctttctctcc ac a ggt gtc cac tcc        161
                                               Gly Val His Ser
                                                            -1 cag gtc caa ctg cag caa tca ggg gct gaa gtc aag aaa cct ggg tca        209
Gln Val Gln Leu Gln Gln Ser Gly Ala Glu Val Lys Lys Pro Gly Ser
  1               5                  10                  15 tcg gtg aag gtc tcc tgc aag gct tct ggc tac acc ttt act agt tac        257
Ser Val Lys Val Ser Cys Lys Ala Ser Gly Tyr Thr Phe Thr Ser Tyr
             20                  25                  30 aat atg cac tgg gtc aag cag gca cct gga cag ggt ctg gaa tgg att        305
Asn Met His Trp Val Lys Gln Ala Pro Gly Gln Gly Leu Glu Trp Ile
         35                  40                  45
```

```
gga gct att tat ccc gga aat ggt gat act tcc tac aat cag aag ttc      353
Gly Ala Ile Tyr Pro Gly Asn Gly Asp Thr Ser Tyr Asn Gln Lys Phe
        50                  55                  60 aag ggt aaa gcc aca ctg act gcc gac gaa tcc acc aat aca gcc tac      401
Lys Gly Lys Ala Thr Leu Thr Ala Asp Glu Ser Thr Asn Thr Ala Tyr
65              70                  75                  80 atg gag ctg agc agc ctg agg tct gag gac acg gca ttt tat tac tgt      449
Met Glu Leu Ser Ser Leu Arg Ser Glu Asp Thr Ala Phe Tyr Tyr Cys
                85                  90                  95 gca aga tcg act tac tac ggc ggt gac tgg tac ttc gat gtc tgg ggc      497
Ala Arg Ser Thr Tyr Tyr Gly Gly Asp Trp Tyr Phe Asp Val Trp Gly
            100                 105                 110 caa ggc acc acg gtc acc gtc tcc tca ggtgagtcct tacaacctct            544
Gln Gly Thr Thr Val Thr Val Ser Ser
            115                 120 ctcttctatt cagcttaaat agatttact gcatttgttg gggggaaat gtgtgtatct      604 gaatttcagg tcatgaagga ctagggacac cttgggagtc agaaagggtc attgggagcc    664
cgggctgatg cagacagaca tcctcagctc ccagacttca tggccagaga tttataggat    724
cc                                                                   726

<210> SEQ ID NO 14
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gly Trp Ser Cys Ile Ile Leu Phe Leu Val Ala Thr Ala Thr Gly
                -15                 -10                  -5

Val His Ser Gln Val Gln Leu Gln Gln Ser Gly Ala Glu Val Lys Lys
         -1  1               5                  10

Pro Gly Ser Ser Val Lys Val Ser Cys Lys Ala Ser Gly Tyr Thr Phe
            15                  20                  25

Thr Ser Tyr Asn Met His Trp Val Lys Gln Ala Pro Gly Gln Gly Leu
30                  35                  40                  45

Glu Trp Ile Gly Ala Ile Tyr Pro Gly Asn Gly Asp Thr Ser Tyr Asn
                50                  55                  60

Gln Lys Phe Lys Gly Lys Ala Thr Leu Thr Ala Asp Glu Ser Thr Asn
            65                  70                  75

Thr Ala Tyr Met Glu Leu Ser Ser Leu Arg Ser Glu Asp Thr Ala Phe
        80                  85                  90

Tyr Tyr Cys Ala Arg Ser Thr Tyr Tyr Gly Gly Asp Trp Tyr Phe Asp
    95                  100                 105

Val Trp Gly Gln Gly Thr Thr Val Thr Val Ser Ser
110                 115                 120

<210> SEQ ID NO 15
<211> LENGTH: 121
<212> TYPE: PRT
<213> ORGANISM: Mus sp.

<400> SEQUENCE: 15

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
               100                 105                 110

Gln Gly Thr Thr Val Thr Val Ser Ser
               115                 120

<210> SEQ ID NO 16
<211> LENGTH: 102
<212> TYPE: PRT
<213> ORGANISM: Mus sp.

<400> SEQUENCE: 16

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                85                  90                  95

Phe Gly Gly Gly Thr Lys
               100

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cggtgactgg tacttcaatg tctggggcca aggcaccacg                          40

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaagcttgcg gccgcgatcc                                                20

<210> SEQ ID NO 19
<211> LENGTH: 40
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 19
cgtggtgcct tggccccaga cattgaagta ccagtcaccg                              40

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctcgagcac acaggacctc                                                    20

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Thr Tyr Tyr Gly Gly Asp Trp Tyr Phe Asp Tyr
1               5                  10

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggtgactgg tacttcgatt actggggcca aggcaccacg                              40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgtggtgcct tggccccagt aatcgaagta ccagtcaccg                              40

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctcgagcac acaggacctc                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                             primer

<400> SEQUENCE: 25
aaagcttgcg gccgcgatcc                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctctgcagag cccaaatctt                                              20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agaggaagac atccggtccc ccc                                          23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 gggggaccg gatgtcttcc tct                                           23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atggttttct cttcgggggc tgg                                          23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccagcccccg aagagaaaac cat                                          23

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 31
acctgcaggc ggccgtcgca                                              20

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Thr Tyr Tyr Gly Gly Asp Trp Tyr Phe Asn Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser His Tyr Gly Ser Asn Tyr Val Asp Tyr Phe Asp Tyr
1               5                   10
```

STRUCTURAL VARIANTS OF ANTIBODIES FOR IMPROVED THERAPEUTIC CHARACTERISTICS

RELATED APPLICATIONS

This application claims the benefit under 35 U.S.C. 119(e) of U.S. Provisional Patent Application Ser. No. 61/082,399, filed Jul. 21, 2008.

BACKGROUND OF THE INVENTION

1. Field of the Invention

The present invention relates to structural variants of anti-CD20 antibodies and/or antigen binding fragments thereof, preferably involving the amino acid sequences of complementarity-determining regions (CDRs), with improved therapeutic characteristics. In particular embodiments, the structural variation may comprise changes to the third CDR sequence of the antibody heavy chain (CDRH3), for example substitution of an aspartate residue for an asparagine residue at Kabat position 101. In other particular embodiments, the structural variation may comprise an arginine residue at Kabat position 94, which may form a salt bridge with an aspartate at Kabat position 101. In still other particular embodiments, the structural variation may comprise a valine residue at Kabat position 102. Such structural variants may provide improved efficacy for diseases related to proliferation of B-cells, such as B-cell leukemias, lymphomas or autoimmune diseases, as well as other immune diseases implicating B-cells. In preferred embodiments, the improved efficacy may allow administration of low dosages of anti-CD20 antibody or antigen binding fragment thereof, such as 80 mg or less, more preferably 50 mg or less, most preferably 30 mg or less, which may be administered two or more times about one to three weeks apart, or even two or more times weekly.

The anti-CD20 antibody may be a humanized, chimeric or human anti-CD20 antibody, particularly a monoclonal antibody (MAb). Other embodiments may concern therapeutic and/or diagnostic conjugates of humanized, chimeric or human anti-CD20 antibodies and methods of treating B-cell lymphomas and leukemias and various autoimmune diseases, for example using humanized, chimeric or human anti-CD20 antibodies. Still other embodiments may relate to antibody fusion proteins or antigen binding fragments thereof comprising at least one anti-CD20 MAb or antigen binding fragment thereof, in some cases in combination with a second, different antibody, especially anti-CD20 antibody, preferably anti-CD20 MAb, or antigen binding fragment thereof. The humanized, chimeric or human MAbs, antigen binding fragments thereof or antibody fusion proteins may be administered alone, as a therapeutic immunoconjugate or in combination with one or more therapeutic agents, with other naked antibodies or other immunoconjugates. Still other embodiments relate to DNA sequences encoding humanized, chimeric or human anti-CD20 antibodies and antibody fusion proteins, vectors and host cells containing the DNA sequences, and methods of making the humanized, chimeric or human anti-CD20 antibodies.

2. Background

The immune system of vertebrates consists of a number of organs and cell types which have evolved to accurately recognize foreign antigens, specifically bind to, and eliminate/destroy such foreign antigens. Lymphocytes, amongst others, are critical to the immune system. Lymphocytes are divided into two major sub-populations, T cells and B cells. Although inter-dependent, T cells are largely responsible for cell-mediated immunity and B-cells are largely responsible for antibody production (humoral immunity).

In humans, each B-cell can produce an enormous number of antibody molecules. Such antibody production typically ceases (or substantially decreases) when a foreign antigen has been neutralized. Occasionally, however, proliferation of a particular B-cell will continue unabated and may result in cancers known as B-cell lymphomas or leukemias. B-cell lymphomas, such as the B-cell subtype of non-Hodgkin's lymphoma, are significant contributors to cancer mortality. The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease. Devesa et al., *J. Nat. Cancer Inst.* 79:701 (1987).

The majority of chronic lymphocytic leukemias are of B-cell lineage. Freedman, *Hematol. Oncol. Clin. North Am.* 4:405 (1990). This type of B-cell malignancy is the most common leukemia in the Western world. Goodman et al., *Leukemia and Lymphoma* 22:1 (1996). The natural history of chronic lymphocytic leukemia falls into several phases. In the early phase, chronic lymphocytic leukemia is an indolent disease, characterized by the accumulation of small mature functionally-incompetent malignant B-cells having a lengthened life span. Eventually, the doubling time of the malignant B-cells decreases and patients become increasingly symptomatic. While treatment can provide symptomatic relief, the overall survival of the patients is only minimally affected. The late stages of chronic lymphocytic leukemia are characterized by significant anemia and/or thrombocytopenia. At this point, the median survival is less than two years. Foon et al., *Annals Int. Medicine* 113:525 (1990). Due to the very low rate of cellular proliferation, chronic lymphocytic leukemia is resistant to cytotoxic drug treatment. Both chronic and acute lymphocytic leukemias of B-cell origin are suitable targets for the therapies described herein.

Traditional methods of treating B-cell malignancies, including chemotherapy and radiotherapy, have limited utility due to toxic side effects. The use of monoclonal antibodies to direct radionuclides, toxins, or other therapeutic agents offers the possibility that such agents can be delivered selectively to tumor sites, thus limiting toxicity to normal tissues. Also, the presence of B-cell antigens on these B-cell malignancies makes them optimal targets for therapy with unconjugated B-cell antibodies, such as against CD19, CD20, CD21, CD23, and CD22 markers on B-cells. HLA-DR, CD30, CD37, CD40, CD45, CD70, CD79a, and other antigens may serve as targets for normal and malignant B-cells, although they are also expressed on other cell types. Further, certain MUC1, MUC2, MUC3, and MUC4 antigens, preferably MUC1, as well as also insulin-like growth factors (ILGF), insulin-like growth factor receptor, macrophage migration-inhibitory factor (MIF), are also expressed in different hematopoietic malignancies, including B-cell tumors expressing CD20 and other B-cell markers. Still other antigen targets, such as those associated with the vascular endothelium of tumors, including tenascin, vascular endothelium growth factor receptor (VEGFR), and placental growth factor (PlGF), as well as other categories of antigens associated with B-cell malignancies, such as oncogene products (cMET, Kras, bcl-2, bcl-6), are also suitable targets for therapeutic antibodies.

B-cells comprise cell surface proteins which can be utilized as markers for differentiation and identification. One such human B-cell marker is the human B lymphocyte-restricted differentiation antigen, Bp35, referred to as CD20.

CD20 is expressed during early pre-B-cell development and remains until plasma cell differentiation. CD20 is expressed on both normal B cells and malignant B cells whose abnormal growth can lead to B-cell lymphomas and leukemias. Antibodies against the CD20 antigen have been investigated for the therapy of B-cell lymphomas and leukemias. For example, a chimeric anti-CD20 antibody, designated as "IDEC-c2B8" (rituximab), has activity against B-cell lymphomas when provided as unconjugated antibodies at repeated injections of doses exceeding 500 mg per injection. Maloney et al., *Blood* 84:2457 (1994); Longo, *Curr. Opin. Oncol.* 8:353 (1996). About 50 percent of non-Hodgkin's patients, having the low-grade indolent form, treated with this regimen showed responses. Therapeutic responses have also been obtained using $^{131}$I-labeled B1 (tositumomab) anti-CD20 murine monoclonal antibody when provided as repeated doses with pretreatment of unlabeled antibodies exceeding 600 mg per injection. Kaminski et al., *N. Engl. J. Med.* 329:459 (1993); Press et al., *N. Engl. J. Med.* 329:1219 (1993); Press et al., *Lancet* 346:336 (1995). However, these antibodies, whether provided as unconjugated forms or radiolabeled forms, have not shown high rates of objective and durable responses in patients with the more prevalent and lethal form of B-cell lymphoma, the intermediate or aggressive types. Therefore, a need exists to develop an immunotherapy for B-cell malignancies that achieves a therapeutic response of significant duration.

Additional studies targeting CD20 surface antigen have been performed using an anti-CD20 murine monoclonal antibody, IF5, which was administered by continuous intravenous infusion to B-cell lymphoma patients. Extremely high levels (>2 grams) of 1F5 were reportedly required to deplete circulating tumor cells, and the results were described as being "transient." Press et al., "Monoclonal Antibody 1F5 (Anti-CD20) Serotherapy of Human B-Cell Lymphomas." *Blood* 69/2:584-591 (1987). However, a potential problem with this approach is that non-human monoclonal antibodies (e.g., murine monoclonal antibodies) typically lack human effector functionality, i.e., they are unable to mediate complement-dependent lysis or lyse human target cells through antibody-dependent cellular toxicity or Fc-receptor mediated phagocytosis. Furthermore, non-human monoclonal antibodies can be recognized by the human host as a foreign protein and, therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response.

The use of chimeric antibodies is preferred because they do not elicit as strong a HAMA response as murine antibodies. Chimeric antibodies are antibodies which comprise portions from two or more different species. For example, Liu, A. Y. et al, "Production of a Mouse-Human Chimeric Monoclonal Antibody to CD20 with Potent Fc-Dependent Biologic Activity" *J. Immunol.* 139/10:3521-3526 (1987), describe a mouse/human chimeric antibody directed against the CD20 antigen. See also, PCT Publication No. WO 88/04936. An exemplary chimeric antibody would comprise mouse variable region sequences attached to human antibody constant region sequences.

The use of humanized antibodies is even more preferred, in order to further reduce the possibility of inducing a HAMA reaction. As discussed below, techniques for humanization of murine antibodies by replacing murine framework and constant region sequences with corresponding human antibody framework and constant region sequences are well known in the art and have been applied to numerous murine anti-cancer antibodies. Antibody humanization may also involve the substitution of one or more human framework amino acid residues with the corresponding residues from the parent murine framework region sequences.

Another approach that has improved the ability of antibodies to be effective in the treatment of B-cell disorders has been to conjugate a therapeutic agent, such as a radioactive or chemotherapeutic agent to the antibody, such that the agent is localized at the tumor site. For example, the above-referenced 1F5 antibody and other B-cell antibodies have been labeled with $^{131}$I and were evaluated for biodistribution in two patients. See Eary, J. F. et al., "Imaging and Treatment of B-Cell Lymphoma" *J. Nuc. Med.* 31/8:1257-1268 (1990); see also, Press, O. W. et al., "Treatment of Refractory Non-Hodgkin's Lymphoma with Radiolabeled MB-1 (Anti-CD37) Antibody" *J. Clin. Oncol.* 7/8:1027-1038 (1989) (indication that one patient treated with $^{131}$I-labeled IF-5 achieved a partial response); Goldenberg, D. M. et al., "Targeting, Dosimetry and Radioimmunotherapy of B-Cell Lymphomas with $^{131}$I-Labeled LL2 Monoclonal Antibody" *J. Clin. Oncol.* 9/4:548-564 (1991) (three of eight patients receiving multiple injections reported to have developed a HAMA response to this CD22 murine antibody); Appelbaum, F. R. "Radiolabeled Monoclonal Antibodies in the Treatment of Non-Hodgkin's Lymphoma" *Hem./Oncol. Clinics of N. Am.* 5/5:1013-1025 (1991) (review article); Press, O. W. et al. "Radiolabeled-Antibody Therapy of B-Cell Lymphoma with Autologous Bone Marrow Support." *New England Journal of Medicine* 329/17: 1219-12223 (1993) ($^{131}$I-labeled anti-CD20 antibody IF5 and B1-tositumomab); and Kaminski, M. G. et al "Radioimmunotherapy of B-Cell Lymphoma with [$^{131}$I] Anti-B1 (Anti-CD20) Antibody". *NEJM* 329/7:459 (1993) ($^{131}$I-labeled anti-CD20 antibody B1); PCT published application WO 92/07466 (antibodies conjugated to chemotherapeutic agents such as doxorubicin or mitomycin). However, these approaches have not eliminated the obstacles associated with using murine antibodies, despite the fact that many patients with lymphoma who have received prior aggressive cytotoxic chemotherapy are immune suppressed, thus having lower HAMA rates than lymphoma patients who have not been heavily pretreated.

Autoimmune diseases are a class of diseases associated with B-cell disorders. Examples comprise acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, Type-I diabetes mellitus, Henoch-Schönlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis. The most common treatments are corticosteroids and cytotoxic drugs, which can be very toxic. These drugs also suppress the entire immune system, can result in serious infection, and have adverse affects on the bone marrow, liver and kidneys. There is a need for more effective methods of treating autoimmune diseases, particularly Class-III autoimmune diseases. A further need exists for the development of more effective antibodies for the treatment of cancer and/or autoimmune disease.

Still other diseases with immunological dysregulation are suitably treated by the novel compositions and methods described herein, such as hemolytic anemias, cryoglobulinemias, hepatitis (particularly hepatitis C), graft-versus-host disease (GVHD) (particularly after allogeneic stem cell transplantation), allosensitization (particularly with organ transplantation). There is now mounting evidence that B-cells are involved in these pathological states, so depleting B-cells by anti-B-cell therapies is gaining in interest (Roccatello et al., *Clin Rev Allergy Immunol* 2008, 34:111-117; Cutler et al., *Blood* 2006, 108:756-752; Vo et al., *N Engl J Med* 2008, 359:242-251; Vieira et al., *Transplantation* 2004; 77:542-548; Abdallah & Prak, *Clin. Transpl.* 2006:427-37; Zaja et al., *Bone Marrow Transplant.*, 2007, 40:273-77; Saadoun et al., *Curr. Opin. Rheumatol.* 2008, 20:23-8; Antonelli et al., *Clin. Exp. Rheumatol.* 2008, 26:S39-47).

SUMMARY OF THE INVENTION

The present invention provides structural variants of anti-CD20 antibodies and/or antigen binding fragments thereof with improved therapeutic characteristics. In particular embodiments, the structural variation may comprise an aspartate residue at Kabat position 101, for example as a substitution for an asparagine residue, in $V_H$ of CDR3 (CDRH3). In other particular embodiments, the structural variation may comprise an arginine residue at Kabat position 94, which may form a salt bridge with an aspartate at Kabat position 101. In still other particular embodiments, the structural variation may comprise a valine residue at Kabat position 102. The skilled artisan will realize that the possible amino acid substitutions that may be performed are not limited to the particular examples recited above and may comprise substitutions at additional and/or different Kabat positions.

The improved therapeutic characteristics may take a variety of forms, such as a slower dissociation rate from the target antigen, an increase in complement-dependent cytotoxicity (CDC) and/or a reduction in $EC_{50}$ in complement-dependent cytotoxicity (CDC). In preferred embodiments, the characteristics may include efficacy at a lower dosage, preferably a dosage of 80 mg or less for a human subject, more preferably a dosage of 50 mg or less, most preferably a dosage of 30 mg or less. The dosage may be administered two or more times. Preferably, where multiple administrations are provided, they are administered about 1 to 3 weeks apart. But in certain disease setting, a more frequent, fractionated dosing is preferred, such as, for example, twice weekly for 4 or more weeks in chronic lymphocytic leukemia.

In certain embodiments, the anti-CD20 antibodies or antigen binding fragments thereof may be humanized, chimeric or human antibodies that bind to a human B-cell marker, such as anti-CD20 antibodies, of use for the treatment and diagnosis of B-cell disorders, such as B-cell malignancies and autoimmune diseases, as well as other diseases involving B-cells, such as GVHD, hemolytic anemia, cryoglobulinemia, allosensitization, and in organ transplant rejection, as well as certain viral diseases, such as hepatitis C. The humanized, chimeric or human anti-CD20 antibodies may be used for methods of treatment of mammalian subjects, such as humans or domestic animals, as naked antibodies either alone or in combination with one or more therapeutic agents, as immunoconjugates labeled with one or more therapeutic and/or diagnostic agents, as an antibody fusion protein, in pre-targeting methods with targetable constructs that are conjugated to one or more therapeutic or diagnostic agents, or as a multimodal therapy with other antibodies, other therapeutic agents or immunomodulators. The humanized, chimeric or human anti-CD20 antibodies can also be used as a diagnostic imaging agent alone, in combination with other diagnostic imaging agents, and/or in conjunction with therapeutic applications.

The skilled artisan will realize that the disclosed methods and compositions for sequence variations with improved therapeutic characteristics are not limited to anti-CD20 antibodies and may be applied to antibodies against other tumor-associated antigens or autoimmune and other immune disease-associated antigens, including but not limited to carbonic anhydrase IX, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-d, CD67, CD70, CD74, CD79a, CD80, CD83, CD95, CD126, CD133, CD138, CD147, CD154, CEACAM6, B7, ED-B fibronectin, Factor H, FHL-1, Flt-1, Flt-3, folate receptor, GROB, HMGB-1, hypoxia inducible factor (HIF), HM1.24, insulin-like growth factor-1 (ILGF-1), ILGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-25, IP-10, MAGE, mCRP, MCP-1, MIP-1A, MIP-1B, MIF, MUC1, MUC2, MUC3, MUC4, NCA-66, NCA-95, NCA-90, Ia, HLA-DR, tenascin, Le(y), RANTES, T101, TAC, Tn antigen, Thomson-Friedenreich antigens, tumor necrosis antigens, TNF-α, TRAIL receptors (R1 and R2), VEGFR, EGFR, PlGF, complement factors C3, C3a, C3b, C5a, C5, and oncogene products, including bcl-2, bcl-6, Kras and cMET.

Other embodiments may be directed to anti-CD20 MAbs or antigen binding fragments thereof that contain specific murine CDRs or a combination of murine CDRs from more than one murine or chimeric anti-CD20 MAb. These MAbs can be humanized, chimeric or human anti-CD20 MAbs. The CDR sequences may include, but are not limited to, light chain CDR sequences CDRL1 (RASSSVSYIH, SEQ ID NO:1), CDRL2 (ATSNLAS, SEQ ID NO:2) and CDRL3 (QQWTSNPPT, SEQ ID NO:3) and heavy chain CDR sequences CDRH1 (SYNMH, SEQ ID NO:4), CDRH2 (AIYPGNGDTSYNQKFKG, SEQ ID NO:5) and CDRH3 (STYYGGDWYFDV, SEQ ID NO:6).

Various embodiments may concern bispecific antibodies or antibody fusion proteins comprising at least two anti-CD20 MAbs or antigen binding fragments thereof or a first MAb comprising an anti-CD20 MAb or antigen binding fragment thereof and a second MAb. The second MAb may bind to a tumor-associated antigen, such as those listed above, or a hapten, for example on a targetable conjugate.

Other embodiments may concern therapeutic or diagnostic conjugates of anti-CD20 MAbs or antigen binding fragments thereof or antibody fusion proteins, bound to at least one therapeutic agent or at least one diagnostic agent. Antibodies and fusion proteins with multiple therapeutic agents of the same or different type are also encompassed. In alternative embodiments, the anti-CD20 antibodies, antigen binding fragments or fusion proteins may be used in therapeutic or diagnostic pre-targeting methods, for example using bispecific antibodies with one arm that binds specifically to a cell, disease, tissue or pathogen (e.g., hepatitis-C-associated target antigen) and a second arm that binds to a targetable conjugate attached to one or more diagnostic or therapeutic agents. Methods of pre-targeting with bispecific antibodies are well known in the art (see, e.g., U.S. Pat. Nos. 7,300,644; 7,138, 103; 7,074,405; 7,052,872; 6,962,702; 6,458,933, the Examples section of each of which is incorporated herein by reference).

Alternative embodiments may concern methods of using the anti-CD20 MAbs or antigen binding fragments thereof or antibody fusion proteins for therapy, either alone, in combination with one or more other therapeutic agents, for example as the antibody component of a therapeutic immunoconjugate with one or more therapeutic agents or as a naked antibody, antigen binding fragment or fusion protein administered alone or in combination with one or more therapeutic agents. Use for diagnostic methods in combination with one or more diagnostic agents is also contemplated. In preferred embodiments, the disease to be diagnosed or treated is a B-cell mediated immune disease, autoimmune disease, B-cell lymphoma or leukemia. B-cell mediated immune disease refers to a sub-class of autoimmune disease, as well as the other immune diseases discussed above (e.g., GVHD, cryoglobulinemia, hemolytic anemia, allosensitization, transplant organ rejection) in which the disease state is primarily mediated by production of autoantibodies, rather than by autoreactive T lymphocytes, or by a combination of B- and T-cell immunity.

BRIEF DESCRIPTION OF THE FIGURES

FIG. 1. Variable light chain (cA20Vk) and variable heavy chain (cA20VH) sequences of cA20, a chimeric anti-CD20 antibody. The CDR region sequences are shown in bold and underlined. The amino acid residues and the nucleotides are numbered sequentially and same numbering system is used for humanized V sequences shown in FIG. 2. The light chain variable region is shown in FIG. 1A (SEQ ID NOS 7 & 8) and the heavy chain variable region is shown in FIG. 1B (SEQ ID NOS 9 & 10). The Kabat numbering scheme was used for amino acid residues. Amino acid residues numbered by a letter represent the insertion residue according to Kabat, and have the same number as that of the previous residue.

FIG. 2. Nucleotide and amino acid sequences of the hA20 light chain hA20Vk (FIG. 2A) (SEQ ID NOS 11 & 12), and heavy chain hA20VH1 (FIG. 2B) (SEQ ID NOS 13 & 14), as well as the adjacent flanking sequences of the VKpBR2 (FIG. 2A) and VHpBS2 (FIG. 2B) staging vectors, respectively. The non-translated nucleotide sequences are shown in lowercase. The restriction sites used for subcloning are underlined and indicated. The secretion signal peptide sequence is indicated by a double underline.

FIG. 3. Comparison of the variable region sequences of cA20 (SEQ ID NOS 10 & 8), rituximab (from murine C2B8, SEQ ID NOS 15 & 16) and hA20 (SEQ ID NOS 14 & 12). Dots indicate homology to cA20. CDR sequences are in boxes. The heavy chain (FIG. 3A) and light chain (FIG. 3B) variable region sequences are shown.

DETAILED DESCRIPTION OF THE INVENTION

Definitions

Figure 4:
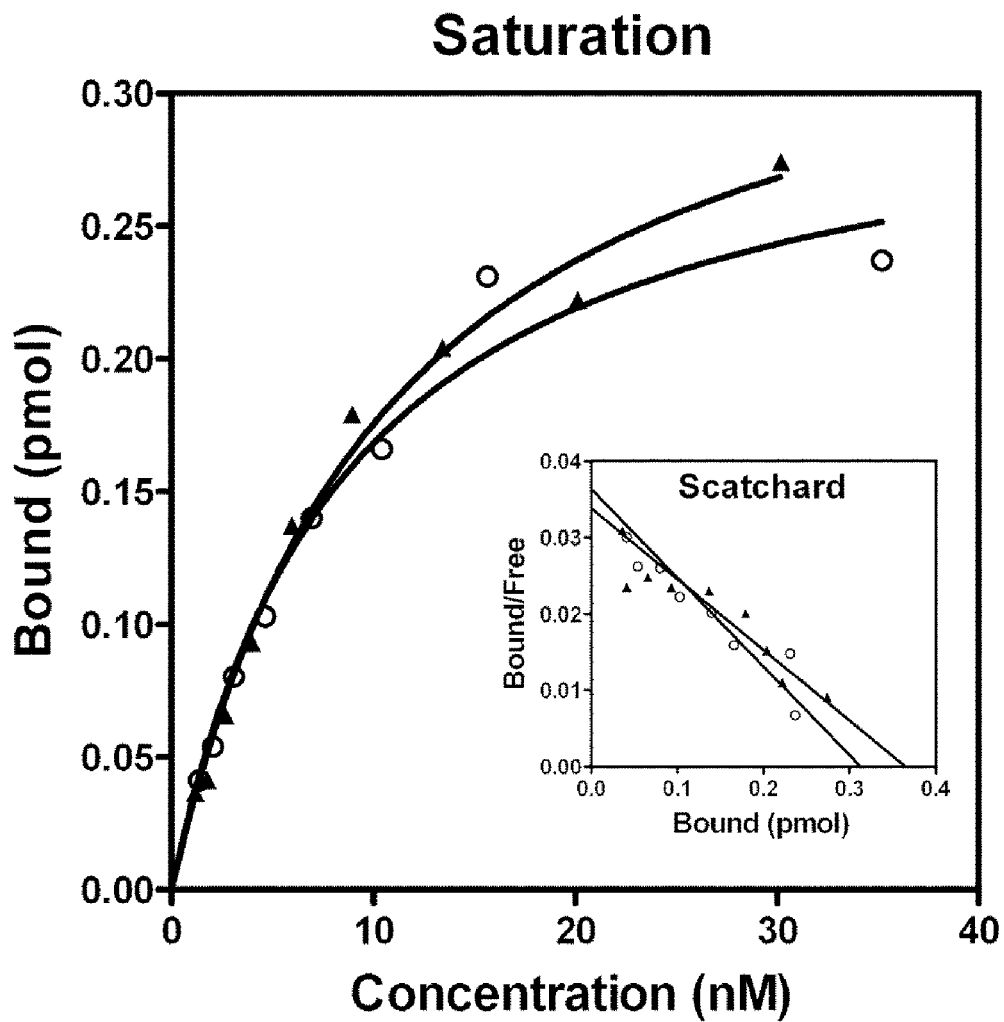
FIG. 4. Scatchard analysis—the binding characteristics of veluzumab and rituximab were determined by binding the $^{125}$I-labeled MAbs to Raji cells. Direct cell surface saturation binding and Scatchard plot analysis (inset)—closed triangles veluzumab; circles rituximab. $B_{max}$ and $K_d$ were determined by non-linear regression analysis using a one-site binding model with Prism software. These results are representative of one of three repeated experiments.

As used herein, an antibody refers to a full-length (i.e., naturally occurring or formed by normal immunoglobulin gene fragment recombinatorial processes) immunoglobulin molecule (e.g., an IgG antibody) or an immunologically active, antigen-binding portion of an immunoglobulin molecule, like an antibody fragment.

An antibody fragment is a portion of an antibody such as F(ab')$_2$, F(ab)$_2$, Fab', Fab, Fv, scFv and the like. Regardless of structure, an antibody fragment binds with the same antigen that is recognized by the intact antibody. For example, an anti-CD20 monoclonal antibody fragment binds to CD20. The term "antibody fragment" also includes isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region. As used herein, the term "antibody fragment" does not include portions of antibodies without antigen binding activity, such as Fc fragments.

A naked antibody refers to an antibody or antigen binding fragment thereof which is not conjugated to a therapeutic agent. The Fc portion of the antibody molecule may provide effector functions, such as complement fixation and ADCC (antibody dependent cell cytotoxicity), which set mechanisms into action that may result in cell lysis. However, it is possible that the Fc portion is not required for therapeutic function, with other mechanisms, such as apoptosis, coming into play. Naked antibodies may include polyclonal and monoclonal antibodies, as well as recombinant antibodies, such as chimeric, humanized or human antibodies.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Non-limiting examples of therapeutic agents include antibodies, antibody fragments, drugs, toxins, nucleases, hormones, immunomodulators, chelators, boron compounds, photoactive agents, oligonucleotides (e.g. anti-sense oligonucleotides or RNAi) and radioisotopes.

A diagnostic agent is a detectable molecule or atom that may be conjugated to an antibody, antibody fragment, targetable construct or other moiety for delivery to a cell, tissue, pathogen or other target associated with a disease or medical condition. Useful diagnostic agents include, but are not limited to, radioisotopes, ultrasound, dyes (such as with the biotin-streptavidin complex), contrast agents, fluorescent compounds or molecules and enhancing agents (e.g. paramagnetic ions for magnetic resonance imaging).

An immunoconjugate is a conjugate of an antibody component with at least one therapeutic or diagnostic agent. An antibody component may be conjugated with multiple therapeutic and/or diagnostic agents to form an immunoconjugate.

The term antibody fusion protein may refer to a recombinantly produced antigen-binding molecule in which one or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or different epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope type. Monospecific, multivalent fusion proteins have more than one binding site for an epitope but only bind with one epitope. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase. Another preferred immunomodulator fusion protein is an immunocytokine, such as fusing an interferon to a specific antibody or multivalent antibody or multispecific antibody as described herein.

A multispecific antibody is an antibody that can bind simultaneously to at least two targets that are of different structure, e.g., two different antigens, two different epitopes on the same antigen, or a hapten and/or an antigen or epitope. One specificity may be for a B-cell, T-cell, myeloid-, plasma- or mast-cell antigen or epitope. Another specificity may be to a different antigen on the same cell type, such as CD20, CD19, CD21, CD23, CD37, CD45, CD70, CD79a, CD80, HLA-DR, CD74, MUC1 or CD22 on B-cells. Multispecific, multivalent antibodies are constructs that have more than one binding site, and the binding sites are of different specificity.

A bispecific antibody is an antibody that can bind simultaneously to two targets which are of different structure. In preferred embodiments, bispecific antibodies (bsAb) and bispecific antibody fragments (bsFab) have at least one arm that specifically binds to, for example, a B-cell, T-cell, myeloid-, plasma- or mast-cell antigen or epitope and at least one other arm that specifically binds to a targetable conjugate that bears a therapeutic or diagnostic agent.

Improved Anti-CD20 Antibodies

Advances in medical therapy during the last ten years have witnessed the introduction of 9 antibodies for the treatment of diverse cancers (Sharkey and Goldenberg, CA Cancer J. Clin. 2006, 56:226-243). Most of these new biological therapeutics are used in combination with conventional cytotoxic drugs, indicating that the antibodies require additional measures to improve their efficacy (Id.). This is best exemplified with rituximab, the first-generation chimeric anti-CD20 monoclonal antibody (MAb) that was approved initially as a monotherapy for the treatment of non-Hodgkin lymphoma (NHL) (Castillo et al., *Exp Hematol.* 2008, 36:755-768). Rituximab is well known in the art and is commercially available from Biogen/IDEC and Genentech (see, e.g., U.S. Pat. Nos. 5,736, 137; 5,776,456; 6,399,061; 6,455,043; 6,846,476). Based on this success, efforts are underway to introduce improved anti-CD20 antibodies (Stein et al., *Clin Cancer Res.* 2004, 10:2868-78; Teeling et al., *Blood.* 2004, 104:1793-1800; Vugmeyster et al., *J Immunother.* 2005, 28:212-219, Umana et al., *Ann Oncol.* 2008, 19(Suppl 7), abstract 98; Forero et al., Proc 99th *Ann Meeting of the Am Assoc Cancer Res*, 2008, abstract LB-70; Glennie et al., *Mol. Immunol.* 2007, 44:3823-37).

Most of these new anti-CD20 MAbs are intended to reduce the murine components while enhancing FcγR or complement-mediated functions (Glennie et al., *Mol. Immunol.* 2007, 44:3823-37; Maloney, *Hematology Am Soc Hematol Educ Program.* 2007:226-232; Martin et al., *Semin Hematol.* 2008, 45:126-132). One of the first second-generation MAbs developed to mitigate the infusion-related reactions experienced with rituximab is the hA20 MAb now termed veltuzumab (e.g., Qu et al., *Blood* 2008, 111:2211-19; Stein et al., *Clin Cancer Res.* 2004, 10:2868-78; U.S. Pat. No. 7,151,164, the Examples section of which is incorporated herein by reference). Veltuzumab has a shorter infusion time than rituximab while indicating a higher complete response (CR) rate than has been reported for rituximab (Morschhauser et al., Proc Am Soc Clin Oncol, J Clin Oncol. 2007, 25(18S): 449s; Goldenberg et al., *Proc Amer Soc Clin Oncol, J. Clin. Oncol.* 2008, 26(15S):142s). As described in the Examples below, veltuzumab was recombinantly engineered using the backbone framework regions of the humanized anti-CD22 MAb, epratuzumab or hLL2 (see, e.g., Leung et al., *Mol. Immunol.* 1995, 32:1413-1427; U.S. Pat. Nos. 6,306,393; 6,183,774 and 7,074,403, the Examples section of each incorporated herein by reference), while having identical light chain CDRs, identical heavy chain CDR1 and CDR2, but a different CDR3-$V_H$ (CDRH3) construct, compared to rituximab, as shown in Table 1 below.

As discussed in the Examples below, as a result of the differences in sequence, veltuzumab has unique characteristics in terms of significantly improved complement-dependent cytotoxicity (CDC) in the Daudi cell line, slower off-rates in all three lymphoma cell lines tested, compared to rituximab, and potent anti-B-cell activity in cynomolgus monkeys and therapeutic effects in human lymphoma-murine models, as well as significantly better control of Raji lymphoma xenografts in mice as compared to rituximab, thus corroborating the activity observed in patients at very low doses. See, Goldenberg et al., 2009, "Properties and structure-function relationships of veltuzumab (hA20), a humanized anti-CD20 monoclonal antibody," *Blood* 113:1062-70. Surprisingly, as described in the Examples below, these functional differences between veltuzumab and rituximab are related to a non-conservative single amino acid change in the heavy chain third complementarity-determining region (CDRH3) (Kabat residue 101) of rituximab. Such a non-conservative change would not be considered by one skilled in the art due to the lack of a reasonable chance or the reduced chance of success to improve the antibody in the designated characteristics.

In various embodiments, the present invention provides humanized, chimeric or human anti-CD20 antibodies, and antibody fusion proteins thereof, useful for treatment of mammalian subjects, humans and domestic animals, alone, as a conjugate or administered in combination with other therapeutic agents, including other naked antibodies and antibody therapeutic conjugates.

In preferred embodiments, the instant anti-CD20 MAbs or antigen binding fragments thereof comprise an aspartate residue at Kabat position 101, an arginine residue at Kabat position 94, and a valine residue at Kabat position 102 of CDR3's $V_H$. More preferably, the anti-CD20 antibodies and antigen binding fragments thereof comprise the CDR sequences of veltuzumab, comprising light chain CDR sequences CDRL1 (RASSSVSYIH, SEQ ID NO:1), CDRL2 (ATSNLAS, SEQ ID NO:2) and CDRL3 (QQWTSNPPT, SEQ ID NO:3) and heavy chain CDR sequences CDRH1 (SYNMH, SEQ ID NO:4), CDRH2 (AIYPGNGDTSYNQKFKG, SEQ ID NO:5) and CDRH3 (STYYGGDWYFDV, SEQ ID NO:6). In most preferred embodiments, the anti-CD20 antibody is veltuzumab.

The humanized anti-CD20 MAb or antigen binding fragment thereof may comprise the CDRs of a murine anti-CD20 MAb (or sequences derived from the CDRs of a murine anti-CD20 antibody) and the framework (FR) and constant regions of the light and heavy chain variable regions of one or more human antibodies, while retaining the B-cell, B-cell lymphoma and B-cell leukemia targeting characteristics of the parent murine anti-CD20 MAb. The humanized anti-CD20 MAb or antigen binding fragment thereof may further comprise at least one amino acid from the corresponding FRs of the parent murine MAb. Specifically, the humanized anti-CD20 MAb or antigen binding fragment thereof may contain at least one amino acid residue corresponding to amino acids 1, 5, 27, 30, 38, 48, 67, 68, 70, 95, 115 or 116 of the heavy chain variable region shown in FIG. 2B (hA20VH1, SEQ ID NO:14) and/or at least one amino acid residue corresponding to amino acid residues 4, 21, 35, 38, 45, 46, 59, 99, 104 or 106 of the light chain variable region shown in FIG. 2A (hA20Vk, SEQ ID NO:12). The murine framework amino acid residues can be substituted in the human FR regions of the light and heavy variable chains if necessary to maintain proper binding or to enhance binding to the CD20 antigen. More preferably the humanized anti-CD20 MAb or antigen binding fragment thereof comprises the amino acid sequences of hA20Vk (SEQ ID NO:12) and hA2VH1 (SEQ ID NO:14).

Chimeric anti-CD20 MAbs or antigen binding fragments thereof may comprise the variable region sequences of a murine anti-CD20 antibody (or derived from a murine anti-CD20 antibody), attached to human antibody constant region sequences. In preferred embodiments, the light and heavy chain variable regions of a chimeric anti-CD20 MAb comprise the CDR sequences of cA20Vk (SEQ ID NO:8) and cA20VH (SEQ ID NO:10), shown in FIGS. 1A and 1B. Most preferably, the chimeric anti-CD20 MAb or antigen binding fragment thereof comprises the light and heavy chain variable region sequences of cA20Vk (SEQ ID NO: 8) and cA20VH (SEQ ID NO:10).

Certain embodiments may concern a human anti-CD20 MAb or antigen binding fragment thereof, having substantially the B-cell, and B-cell lymphoma and leukemia cell targeting and cell binding characteristics of a murine anti-CD20 MAb, wherein the CDRs are as set forth above for the chimeric and humanized anti-CD20 MAbs as shown in FIGS. 1 and 2.

Other embodiments may encompass antibody fusion proteins or antigen binding fragments thereof comprising at least one anti-CD20 MAb or antigen binding fragments thereof, as described above. The antibody fusion protein or antigen binding fragment thereof is also intended to encompass an antibody fusion protein or antigen binding fragment thereof comprising at least one first anti-CD20 MAb or antigen binding fragment thereof as described above and at least one second MAb or antigen binding fragment thereof, other than the anti-CD20 MAb or antigen binding fragment thereof described above. More preferably this second MAb is a MAb reactive with B7, CD4, CD5, CD8 CD14, CD15, CD16, CD19, CD20, CD21, CD22, CD23, CD25, CD30, CD32b, CD33, CD37, CD38, CD40, CD40L, CD45, CD46, CD52, CD54, CD55, CD59, CD70, CD74, CD80, CD95, CD126, CD133, CD138, CD154, CEACAM6, ED-B fibronectin, Factor H, FHL-1, Flt-1, Flt-3, folate receptor, GROB, HMGB-1, hypoxia inducible factor (HIF), HM1.24, insulin-like growth factor-1 (ILGF-1), insulin-like growth factor-1 receptor (ILGF-1R), IFN-γ, IFN-α, IFN-β, IL-2, IL-4R, IL-6R, IL-13R, IL-15R, IL-17R, IL-18R, IL-6, IL-8, IL-12, IL-15, IL-17, IL-25, IP-10, MAGE, mCRP, MCP-1, MIP-1A, MIP-1B, MIF, MUC1, MUC2, MUC3, MUC4, NCA-66, Ia, HM1.24, HLA-DR, tenascin, T101, TAC, TRAIL-R1, TRAIL-R2, VEGFR, EGFR, PlGF, complement factor C5, and an oncogene product (e.g., Kras, cMET, bcl-2, bcl-6) or a combination thereof, and even an anti-CD20 MAb that is different than the anti-CD20 MAb described herein.

The humanized, chimeric or human anti-CD20 antibody may possess enhanced affinity binding with the epitope, as well as antitumor and anti-B-cell activity, as a result of CDR mutation and manipulation of the CDR and other sequences in the variable region to obtain a superior therapeutic agent for the treatment of B-cell disorders, including B-cell lymphomas and leukemias and autoimmune diseases and also other immune diseases involving B-cells (GVHD, hemolytic anemia, organ transplant rejection).

Amino Acid Substitutions

It may also be desirable to modify the amino acid sequences to improve effector function, e.g., to enhance antibody-dependent cell-dependent cytotoxicity (ADCC) and/or complement-dependent cytotoxicity (CDC). One or more amino acid substitutions or the introduction of cysteine in the Fc region may be made, thereby improving internalization capability and/or increased complement-dependent cell killing and ADCC. See Caron et al., *J. Exp. Med.* 176:1191-1195 (1991) and Shopes, Br. *J. Immunol.* 148:2918-2022 (1992), incorporated herein by reference. An antibody fusion protein may be prepared that has dual Fc regions with both enhanced complement lysis and ADCC capabilities.

Changes to the Fc region to enhance effector function or other antibody functional characteristics have been reported (see, e.g., Lazar et al., *Proc. Natl. Acad. Sci. USA* 2006, 103:4005-10; Stavenhagen et al., *Cancer Res.* 2007, 67:8882-90; Hinton et al., *J. Immunol.* 2006, 176:346-56; Idusogie et al., *J. Immunol.* 2001, 166:2571-75) and any such known Fc region amino acid substitutions may be utilized in the claimed methods and compositions. For example, replacement of a serine residue with an aspartate residue at Kabat position 239 was reported to enhance ADCC activity (Lazar et al., ibid., 2006). Substitution of phenylalanine 243 with leucine, arginine 292 with proline, tyrosine 300 with leucine, valine 305 with isoleucine and proline 396 with leucine also appeared to optimize ADCC activity (Stagenhagen et al., 20007). Replacement of threonine 250 with glutamine and methionine 428 with leucine resulted in an apparent increase in serum half-life (Hinton et al., ibid., 2006). Substitution of lysine 326 with tryptophan and glutamate 333 with serine appeared to increase CDC activity (Idusogie et al., ibid., 2001). These and other known modifications to enhance antibody physiological function may be combined with changes to variable region sequence, described herein, to produce anti-CD20 antibodies of improved therapeutic characteristics.

In certain embodiments, the disclosed methods and compositions may involve production and use of antibodies or antigen-binding fragments thereof with one or more substituted amino acid residues. As discussed below, methods for making monoclonal antibodies against virtually any target antigen are well known in the art. Typically, these result in production of murine antibodies against a target antigen. As is well known in the art, the antigen-binding specificity of murine monoclonal antibodies is determined largely by the hypervariable complementarity determining region (CDR) sequences. Murine antibodies generally comprise 6 CDR sequences, 3 on the antibody light chain and 3 on the heavy chain. As described in detail below, chimeric, humanized or human versions of murine antibodies may be constructed by techniques such as CDR grafting, where the murine CDR sequences are inserted into, for example, human antibody framework and constant region sequences, or by attaching the entire murine variable region sequences to human antibody constant region sequences. In alternative embodiments, the variable region sequences of an antibody may be constructed, for example, by chemical synthesis and assembly of oligonucleotides encoding the entire light and heavy chain variable regions of an antibody.

In various embodiments, the structural, physical and/or therapeutic characteristics of chimeric, humanized or human antibodies may be optimized by replacing one or more amino acid residues.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred, but not required.

Other considerations include the size of the amino acid side chain. For example, it would generally not be preferred to replace an amino acid with a compact side chain, such as glycine or serine, with an amino acid with a bulky side chain, e.g., tryptophan, tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, *Biochemistry*, 13:222-245; 1978, *Ann. Rev. Biochem.*, 47: 251-276; 1979, *Biophys. J.*, 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (O) glu, asn; Glu (E) gln, asp; Gly (G) ala; H is (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For CDR residues, the residue in the free antibody would normally be assumed to be solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Preparation of Monoclonal Antibodies Including Chimeric, Humanized or Human Antibodies Techniques for preparing monoclonal antibodies against virtually any target antigen are well known in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization or chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat. Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat. Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). The affinity of humanized antibodies for a target may also be increased by selected modification of the CDR sequences (WO0029584A1).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric, humanized or human antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g., Johnson and Chiswell, *Current Opinion in Structural Biology* 3:5564-571 (1993). Human antibodies may also be generated by in vitro activated B-cells. See U.S. Pat. Nos. 5,567,610 and 5,229,275, the Examples section of each of which is incorporated herein by reference. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Production of Antibody Fragments

Antibody fragments which recognize specific epitopes can be generated by known techniques. The antibody fragments are antigen binding portions of an antibody, such as $F(ab')_2$, Fab', $F(ab)_2$, Fab, Fv, scFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, *Science,* 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. Nos. 4,704,692, 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991), incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. For example, an enzymatic cleavage using papain produces two monovalent Fab fragments and an Fc fragment. These methods are described, for example, by Goldenberg, U.S. Pat. Nos. 4,036,945 and 4,331,647 and references contained therein, which patents are incorporated herein by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al., *Lancet* 1990; 355:368-371). Pre-targeting methods with bispecific antibodies comprising at least one binding site for a tumor-associated antigen (TAA) or other disease target, as well as at one binding site for a targetable construct conjugated to therapeutic or diagnostic agents, are also well known in the art (see, e.g., U.S. Pat. Nos. 7,300,644; 7,138,103; 7,074,405; 7,052,872; 6,962,702; 6,458,933, the Examples section of each of which is incorporated herein by reference).

Bispecific antibodies comprising the antigen-binding variable region sequences of any known anti-TAA antibody may be utilized, including but not limited to hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 7,074,403), hMu-9 (U.S. Pat. No. 7,387,773), hL243 (U.S. patent application Ser. No. 11/368,296), hMN-14 (U.S. Pat. No. 6,676,924), hRS7 (U.S. Pat. No. 7,238,785), hMN-3 (U.S. patent application Ser. No. 10/672,278) and hR1 (U.S. Provisional Patent Application Ser. No. 61/145,896, filed Jan. 20, 2009), the Examples section of each cited patent or application incorporated herein by reference.

Other antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206' 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Numerous methods to produce bispecific or multispecific antibodies are known, as disclosed, for example, in U.S. Patent Application Publication No. 20050002945, filed Feb. 11, 2004, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, *Nature,* 1983; 305:537-540).

Another method for producing bispecific antibodies uses heterobifunctional cross-linkers to chemically tether two different monoclonal antibodies (Staerz, et al., *Nature* 1985; 314:628-631; Perez, et al., *Nature* 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan, *Proc Natl Acad Sci USA* 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al., *Proc Natl Acad Sci USA* 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. Nos. 4,946,778 and 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Patent Application Publ. Nos. 20060228357 (now issued U.S. Pat. No. 7,550,143); 20060228300 (now issued U.S. Pat. No. 7,521,056); 20070086942 (now issued U.S. Pat. No. 7,534,866); 20070140966 (now issued U.S. Pat. No. 7,527,787); 20070264265 and 20090060862 and U.S. Ser. No. 12/418,877, filed Apr. 8, 2009, the Examples section of each of which is incorporated herein by reference). The technique utilizes complementary protein binding domains, referred to as anchoring domains and dimerization and docking domains, which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multi specific antibodies, either as naked antibody moieties or in combination with a wide range of other effector molecules such as immunomodulators, enzymes, chemotherapeutic agents, chemokines, cytokines, diagnostic agents, therapeutic agents, radionuclides, imaging agents, anti-angiogenic agents, growth factors, oligonucleotides, hormones, peptides, toxins, pro-apoptotic agents, or a combination thereof. Any of the techniques known in the art for making bispecific or multi specific antibodies may be utilized in the practice of the presently claimed methods.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct or targetable conjugate) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are well known in the art, for example, as disclosed in Goodwin et al., U.S. Pat. No. 4,863,713; Goodwin et al., *J. Nucl. Med.* 29:226, 1988; Hnatowich et al., *J. Nucl. Med.* 28:1294, 1987; Oehr et al., *J. Nucl. Med.* 29:728, 1988; Klibanov et al., *J. Nucl. Med.* 29:1951, 1988; Sinitsyn et al., *J. Nucl. Med.* 30:66, 1989; Kalofonos et al., *J. Nucl. Med.* 31:1791, 1990; Schechter et al., *Int. J. Cancer* 48:167, 1991; Paganelli et al., *Cancer Res.* 51:5960, 1991; Paganelli et al., *Nucl. Med. Commun.* 12:211, 1991; U.S. Pat. No. 5,256,395; Stickney et al., *Cancer Res.* 51:6650, 1991; Yuan et al., *Cancer Res.* 51:3119, 1991; U.S. Pat. No. 6,077,499; U.S. Ser. Nos. 09/597,580; 10/361,026; 09/337,756; 09/823,746; 10/116,116; 09/382,186; 10/150,654; U.S. Pat. Nos. 6,090,381; 6,472,511; U.S. Ser. No. 10/114,315; U.S. Provisional Application No. 60/386,411; U.S. Provisional Application No. 60/345,641; U.S. Provisional Application No. 60/3328,835; Provisional Application No. 60/426,379; U.S. Ser. Nos. 09/823,746; 09/337,756; U.S. Provisional Application No. 60/342,103; and U.S. Pat. No. 6,962,702.

A pre-targeting method of treating or diagnosing a disease or disorder in a subject may be provided by: (1) administering to the subject a bispecific antibody or antigen binding antibody fragment; (2) optionally administering to the subject a clearing composition, and allowing the composition to clear the antibody from circulation; and (3) administering to the subject the targetable construct, containing one or more chelated or chemically bound therapeutic or diagnostic agents. The technique may also be utilized for antibody dependent enzyme prodrug therapy (ADEPT) by administering an enzyme conjugated to a targetable construct, followed by a prodrug that is converted into active form by the enzyme.

Therapeutic and Diagnostic Agents

In certain embodiments, the antibodies, antigen binding antibody fragments or fusion proteins described herein may be administered alone, as a "naked" antibody, antigen binding fragment thereof or fusion protein. In alternative embodiments, the antibody, antigen binding fragment thereof or fusion protein may be administered before, concurrently with, or after at least one other therapeutic agent. In other alternatives, an antibody, antigen binding fragment thereof or fusion protein may be covalently or non-covalently attached to at least one therapeutic and/or diagnostic agent to form an immunoconjugate.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{72}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from barium compounds, gallium compounds and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Therapeutic agents are preferably selected from the group consisting of a radionuclide, an immunomodulator, an anti-angiogenic agent, a cytokine, a chemokine, a growth factor, a hormone, a drug, a prodrug, an enzyme, an oligonucleotide, an interference RNA, a pro-apoptotic agent, a photoactive therapeutic agent, a cytotoxic agent, which may be a chemotherapeutic agent or a toxin, a second antibody or fragment thereof and a combination thereof. The drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epidophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -β; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, Flt-1, angiostatin, thrombospondin, endostatin, tumor necrosis factor (TNF, such as TNF-α) and LT. As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. Some useful diagnostic nuclides may include $^{124}$I, $^{123}$I, $^{131}$I, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photo-activated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Other useful therapeutic agents comprise oligonucleotides, especially antisense oligonucleotides that preferably are directed against oncogenes and oncogene products of B-cell malignancies, such as bcl-2. Preferred antisense oligonucleotides include those known as siRNA or RNAi.

Immunoconjugates

Any of the antibodies, antigen binding antibody fragments or antibody fusion proteins described herein may be conjugated to one or more therapeutic or diagnostic agents. The therapeutic agents do not need to be the same but can be different, e.g., a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antigen binding antibody fragment. However, it is possible to introduce a carbohydrate moiety into the light chain variable region of a full length antibody or antigen binding antibody fragment. See, for example, Leung et al., *J. Immunol.* 154: 5919 (1995); Hansen et al., U.S. Pat. No. 5,443,953 (1995), Leung et al., U.S. Pat. No. 6,254,868, each incorporated herein by reference. The engineered carbohydrate moiety is used to attach the therapeutic or diagnostic agent.

In some embodiments, a chelating agent may be attached to an antibody, antigen binding antibody fragment or fusion protein or to a targetable construct and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. patent application Ser. No. 12/112,289, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radio-imaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F—Al conjugate may be complexed with chelating groups, such as DOTA, NOTA or NETA that are attached directly to antibodies or used to label targetable constructs in pre-targeting methods. Such F-18 labeling techniques are disclosed in U.S. patent application Ser. No. 12/112,289, the Examples section of which is incorporated herein by reference.

Methods of Therapeutic Treatment

Various embodiments concern methods of treating a B-cell lymphoma or leukemia cell disease or an autoimmune disease in a subject, such as a mammal, including humans, domestic or companion pets, such as dogs and cats, comprising administering to the subject a therapeutically effective amount of an antibody, antigen binding fragment thereof or fusion protein. In preferred embodiments, the antibody or antigen binding fragment thereof is an anti-CD20 MAb. In certain embodiments, the therapy may utilize a "naked antibody" that does not have a therapeutic agent bound to it.

The administration of a "naked" anti-CD20 antibody can be supplemented by administering concurrently or sequentially a therapeutically effective amount of another "naked antibody" that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM6, B7, MUC1, MUC2, MUC3, MUC4, Ia, HM1.24, HLA-DR, tenascin, Flt-1, Flt-3, VEGFR, PlGF, ILGF, ILGF-1R, IL-6, IL-25, tenascin, MIF, complement factor C5, an oncogene, oncogene product, bcl-2, bcl-6, Kras, cMET, or a combination thereof.

Both the naked anti-CD20 therapy alone or in combination with other naked MAbs can be further supplemented with the administration, either concurrently or sequentially, of at least one therapeutic agent, as discussed above. Multimodal therapies may include therapy with naked anti-CD20 antibodies supplemented with administration of anti-CD22, anti-CD19, anti-CD21, anti-CD74, anti-CD80, anti-CD23, anti-CD45, or HLA-DR (including the invariant chain) antibodies in the form of naked antibodies, fusion proteins, or as immunoconjugates. Immunoconjugates may comprise an antibody or antigen binding fragment thereof conjugated to one or more of any therapeutic and/or diagnostic agent as discussed above. The naked anti-CD20 antibodies or antigen binding fragments thereof may also be supplemented with naked antibodies against a MUC1 antigen that is expressed on certain B-cells. Various antibodies of use, such as anti-CD19 and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; and U.S. Patent Application Publ. Nos. 20080131363; 20080089838; 20070172920; 20060193865; 20060210475; 20080138333; and 20080146784, the Examples section of each listed patent or patent application incorporated herein by reference.

In another form of multimodal therapy, subjects receive naked anti-CD20 antibodies, and/or immunoconjugates, in conjunction with standard cancer chemotherapy. For example, "CVB" (1.5 g/m cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1. In a preferred multimodal therapy, both chemotherapeutic drugs and cytokines are co-administered with an antibody, immunoconjugate or fusion protein, preferably comprising an anti-CD20 antibody or antigen binding fragment thereof. Generally, co-administration would refer to the simultaneous administration of two or more agents, such as an antibody and a therapeutic agent. The cytokines, chemotherapeutic drugs and antibody or immunoconjugate can be administered in any order, or together.

Immunoconjugates or naked antibodies can be formulated according to known methods to prepare pharmaceutically useful compositions, whereby the immunoconjugate or naked antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody can be formulated for intravenous administration via, for example, bolus injection or continuous infusion. Preferably, the antibody is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. Preferably, the antibody is infused over a period of less than about 4 hours, and more preferably, over a period of less than about 3 hours. This is preferably performed by infusing slowly at first. For example, a dose of 25 to 50 mg is infused within 15-30 minutes and the remainder of the dose is infused over a period of up to 2-3 hrs.

Generally, the dosage of an administered immunoconjugate, fusion protein or naked antibody for humans will vary depending upon such factors as the patient's age, weight, height, sex, general medical condition and previous medical history. With therapeutic antibodies of lower efficacy than veltuzumab, it may be desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. Dosages may range from 1 to 20, 5 to 10, 2 to 10, 10 to 20, 5 to 15, 1 to 10, 1 to 5, 2 to 5 mg/kg or any range in between 1 and 20 mg/kg. The dosage may be repeated as needed, for example, once per week for 4-10 weeks, once per week for 8 weeks, once per week for 4 weeks, or twice or 3-times per week for 2-8 weeks. It may also be given less frequently, such as every other week for several months, or monthly or quarterly for many months, as needed in a maintenance therapy.

Alternatively, an antibody such as a naked anti-CD20 MAb, may be administered as one dosage every 2 or 3 weeks, repeated for a total of at least 3 dosages. Or, the antibodies may be administered once per week for 4-8 weeks. If the dosage is lowered to approximately 200-300 mg/m$^2$ (340 mg per dosage for a 1.7-m$^2$ patient, or 4.9 mg/kg for a 70 kg patient) or less, it may be administered once weekly for 4 to 8 weeks. Alternatively, the dosage schedule may be decreased, namely every 2 or 3 weeks for 2-3 months. The dosing schedule can optionally be repeated at other intervals and dosage may be given through various parenteral routes, with appropriate adjustment of the dose and schedule.

In an exemplary embodiment, NHL or an autoimmune disease may be treated with 4 weekly infusions of a humanized anti-CD20 antibody at a dose of 100-400 mg/m$^2$ weekly for 4 consecutive weeks (i.v. (intravenously) over 2-6 hours), repeated as needed over the next months/yrs. Alternatively, the humanized anti-CD20 antibody may be administered at a dose of 100-300 mg/m$^2$ once every other week or every third week, for 4 to 8 injections. In another alternative, NHL may be treated with 4 weekly infusions as above, or injections less frequently as above, but combined with epratuzumab (anti-CD22 humanized antibody) on the same days, at a dose of 360 mg/m$^2$, given as i.v. (intravenously) infusion over 1 hour, either before, during or after the anti-CD20 monoclonal antibody infusion. Or, the antibodies used in combination therapy may also be infused in alternative sequences, such that they are alternated on different weeks, resulting in each being given every other week for a total injection sequence for each of 4 to 8 or more doses. These dosage schedules may then be repeated at different intervals, such as every 3-6 months, depending on the patient's clinical status and response to each therapy regimen. In a further alternative, NHL may be treated with 4 weekly infusions, or less frequent infusions, of an anti-CD20 antibody, combined with one or more injections of CD22 MAb radiolabeled with a therapeutic isotope such as yttrium-90 (at a total dose of Y-90 between 5 and 35 mCi/meter-square as one or more injections over a period of weeks or months). U.S. Ser. No. 09/590,284, incorporated herein by reference, discloses immunotherapy of autoimmune disorders using an anti-CD22 antibody.

In preferred embodiments, a naked or conjugated anti-CD20 antibody that has been engineered to be particularly efficacious, such as veltuzumab, may be administered at very low dosages for treatment of diseases such as B-cell diseases, such as B-cell lymphomas or leukemias, systemic lupus erythematosus, follicular lymphoma, non-Hodgkin's lymphoma or immune thrombocytopenic purpura, or pemphigus vulgaris, as well as such immune diseases as GVHD, hemolytic anemia, cryoglobulinemia, allosensitization, and organ transplant rejection. As described in the following Examples, doses as low as 80 mg or less of veltuzumab, more preferably 50 mg or less, most preferably 30 mg or less, may be efficacious when administered to a human subject. Such dosages may preferably be administered two or more times to the subject at an interval of about one to three weeks, and may even be given more than once weekly, e.g., twice or thrice weekly, such as in a fractionated dosing which may continue over several weeks (which may be preferred in certain diseases, such as, for example, chronic lymphocytic leukemia). Surprisingly, such low doses of highly efficacious anti-CD20 antibodies such as veltuzumab have been found to be effective to deplete circulating B-cells and/or to inhibit the growth of B-cell related tumors. Administration of low dosage anti-CD20 antibodies is preferably by intravenous or subcutaneous delivery.

As described in the Examples below, preferred protocols for low-dosage administration of veltuzumab have been found to work well in the practice of the claimed methods and may be utilized. For example, in a mouse model system of Burkitt lymphoma, a single i.p. (intraperitoneal) or s.c. (subcutaneously) injection of as low as 5 µg veltuzumab per 20 gm mouse produced a significant decrease in mortality compared to controls (Example 13). Extrapolating to a 70 kg human the 5 µg dosage would be equivalent to a single 17.5 mg injection of veltuzumab. A higher mouse dosage of 20 µg veltuzumab (equivalent to 70 mg for a 70 kg individual), administered as a single i.p. or s.c. injection, resulted in a four-fold increase in mean survival time (Example 13). Dosages in mice as low as 0.05 µg single dose (equivalent to 0.175 mg for a 70 kg individual) still resulted in a significant improvement in survival relative to controls, with a two-fold increase in mean survival time. While such low dosages may produce significant improvement relative to controls, the effective treatment of B-cell related diseases may utilize somewhat higher dosages for better therapeutic effects. Non-limiting examples include administration of 80 mg i.v. veltuzumab in 2 doses at an interval of two weeks (Example 15), 4 once-weekly doses of 138 mg (80 mg/m$^2$) i.v. veltuzumab (Example 15), 4 doses of 80 mg veltuzumab administered s.c. at two week intervals (Example 15), 4 weekly doses of 80 mg/m$^2$ i.v. veltuzumab (Example 15), 2 doses of 10 mg veltuzumab s.c. at two week interval (Example 17), doses of 40 mg veltuzumab s.c. twice weekly for 6 weeks (Example 18), 2 doses of 40 mg veltuzumab s.c. 2 weeks apart (Example 19), 3 doses of 120 mg veltuzumab s.c. weekly (Example 20), an initial i.v. injection of 15 mg veltuzumab followed by 40 mg s.c. weekly for 3 weeks (Example 21), 4 s.c. injections of 40 mg veltuzumab at zero, 8, 12 and 21 days (Example 22) and 4 s.c. injections of 80 mg veltuzumab two weeks apart (Example 16). It is noteworthy that in the latter case (Example 16), a single s.c. injection of 80 mg veltuzumab produced a significant regression of a tumor neck mass and rapid depletion of circulating B-cells. Example 24 shows that 4 once-weekly doses of veltuzumab as low as 80 mg/m$^2$ resulted in complete responses in at least some human patients with NHL.

The skilled artisan will realize that the disclosed dosages of veltuzumab are exemplary only and that other non-limiting dosages may be utilized in the practice of the claimed methods, such as 5, 10, 15, 20, 25, 30, 35, 40, 45, 50, 55, 60, 65, 70, 75, 80, 85, 90, 95 or 100 mg veltuzumab (total dose) or 5, 10, 15, 20, 25, 30, 35, 40, 45, 50, 55, 60, 65, 70, 75, 80, 85, 90, 95 or 100 mg/m$^2$ veltuzumab, administered i.v. or more preferably s.c. Potential useful ranges of In certain embodiments, veltuzumab may be provided in the form of prefilled syringes or autoinjection pens, formulated for s.c., i.v. or other parenteral injection, at a dosage of 10 to 180, 10 to 100 mg, 20 to 80 mg, 30 to 60 mg, 40 to 50 mg or any other range of dosages.

Exemplary ranges of low-dosage veltuzumab for s.c., i.v. or i.p. administration may be less than 1 mg, 1 to 2 mg, 1 to 5 mg, 1 to 10 mg, 1 to 20 mg, 1 to 50 mg, 1 to 75 mg, 1 to 100 mg, 2 to 5 mg, 2 to 10 mg, 2 to 20 mg, 2 to 50 mg, 2 to 75 mg, 2 to 100 mg, 5 to 10 mg, 5 to 20 mg, 5 to 30 mg, 5 to 40 mg, 5 to 50 mg, 5 to 60 mg, 5 to 75 mg, 5 to 100 mg, 10 to 20 mg, 10 to 30 mg, 10 to 40 mg, 10 to 50 mg, 10 to 60 mg, 10 to 75 mg, 10 to 100 mg, 20 to 30 mg, 20 to 40 mg, 20 to 50 mg, 20 to 60 mg, 20 to 75 mg, 20 to 100 mg, 25 to 40 mg, 25 to 50 mg, 25 to 60 mg, 25 to 75 mg, 25 to 100 mg, 30 to 40 mg, 30 to 50 mg, 30 to 60 mg, 30 to 75 mg, 30 to 100 mg, 40 to 50 mg, 40 to 60 mg, 40 to 75 mg, 40 to 100 mg, 50 to 60 mg, 50 to 75 mg, 50 to 100 mg, 60 to 70 mg, 60 to 80 mg, 60 to 90 mg, 60 to 100 mg or 75 to 100 mg. Alternatively, the same ranges in mg/m$^2$ may be administered to a human subject. As discussed in the Examples below, such low dosages of veltuzumab have been shown to be effective at least in animal model systems and some exemplary human subjects with B-cell related leukemias or lymphomas or autoimmune diseases, or other immune diseases.

The compositions described herein are particularly useful for treatment of various autoimmune diseases as well as indolent forms of B-cell lymphomas, aggressive forms of B-cell lymphomas, chronic lymphatic leukemias, acute lymphatic leukemias, and Waldenström's macroglobulinemia, as well as GVHD, cryoglobulinemia, hemolytic anemia, allosensitization, and organ transplant rejection. For example, the humanized anti-CD20 antibody components and immunoconjugates can be used to treat both indolent and aggressive forms of non-Hodgkin's lymphoma, various autoimmune diseases (e.g., rheumatoid arthritis, SLE, Sjögren's syndrome, pemphigus vulgaris, immune thrombocytopenic purpura), and various other immune diseases (organ transplant rejection, such as kidney and heart rejection, GVHD after allogeneic stem cell transplantion, and immune hemolytic anemia).

As discussed supra, the antibodies can be used for treating B-cell lymphoma and leukemia, and other B-cell diseases or disorders. Exemplary types of cancers that may be targeted include acute lymphoblastic leukemia, chronic lymphocytic leukemia, Hodgkin's lymphoma, non-Hodgkin's lymphoma and multiple myeloma.

Anti-CD20 antibodies can be used to treat B-cell related autoimmune diseases, including Class III autoimmune diseases such as immune-mediated thrombocytopenias (acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, rheumatoid arthritis, polyglandular syndromes, bullous pemphigoid, diabetes mellitus, Henoch-Schönlein purpura, post-streptococcal nephritis, erythema nodosum, Takayasu's arteritis, Addison's disease, sarcoidosis, ulcerative colitis, erythema multiforme, IgA nephropathy, polyarteritis nodosa, ankylosing spondylitis, Goodpasture's syndrome, thromboangitis obliterans, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

Anti-CD20 antibodies may also induce apoptosis in cells expressing the CD20 antigen. For example, it was demonstrated that apoptosis could be induced using lymphoid cells that have Fc-receptors reactive with the IgG1-Fc of CD20 MAbs that are crosslinked. See Shan et al., *Cancer Immunol. Immunother.* 48(12):673-683 (2000). Further, it was reported that aggregates of a chimeric CD20 MAb, i.e., homopolymers, induced apoptosis. See Ghetie et al., *Blood* 97(5): 1392-1398 (2000) and Ghetie et al., *Proc. Natl. Acad. Sci. USA* 94(14): 7509-7514 (1997).

Kits

Various embodiments may concern kits containing components suitable for treating or diagnosing diseased tissue in a patient. Exemplary kits may contain at least one antibody, antigen binding fragment or fusion protein as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, an anti-CD20 antibody or antigen binding fragment thereof, such as veltuzumab, may be provided in the form of a prefilled syringe or autoinjection pen containing a sterile, liquid formulation or lyophilized preparation of antibody (e.g., Kivitz et al., Clin. Ther. 2006, 28:1619-29).

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Expression Vectors

Still other embodiments may concern DNA sequences comprising a nucleic acid encoding an antibody, antigen binding fragment thereof, fusion protein or bispecific antibody. Exemplary sequences that may be encoded and expressed include an anti-CD20 MAb or antigen binding fragment thereof, a fusion protein comprising at least one anti-CD20 antibody or antigen binding fragments thereof, a fusion protein comprising at least one first antibody or antigen binding fragment thereof and at least one second antibody or antigen binding fragment thereof. The first and second antibodies may comprise an anti-CD20 antibody, an antibody against a tumor or B-cell associated antigen such as B7, CD4, CD5, CD8 CD14, CD15, CD16, CD19, CD20, CD21, CD22, CD23, CD25, CD30, CD32b, CD33, CD37, CD38, CD40, CD40L, CD45, CD46, CD52, CD54, CD55, CD59, CD70, CD74, CD79a, CD80, CD95, CD126, CD133, CD138, CD154, CEACAM6, ED-B fibronectin, IL-2, IL-6, IL-25, MUC1, MUC2, MUC3, MUC4, MIF, NCA-66, Ia, HM1.24, HLA-DR, tenascin, T101, TAC, TRAIL-R1, TRAIL-R2, VEGFR, EGFR, PlGF, ILGF, ILGF-IR, Flt-1, Flt-3, tenascin, complement factor C5, an oncogene product, Kras, cMET, bcl-2, bcl-6, and/or a hapten on a targetable construct.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express MAbs in a selected host cell, immunoglobulin enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci. USA* 63: 78-85 (1969).

Also encompassed is a method of expressing antibodies or antigen binding fragments thereof or fusion proteins. The skilled artisan will realize that methods of genetically engineering expression constructs and insertion into host cells to express engineered proteins are well known in the art and a matter of routine experimentation. Host cells and methods of expression of cloned antibodies or antigen binding fragments have been described, for example, in U.S. patent application Ser. Nos. 11/187,863, filed Jul. 25, 2005; U.S. Pat application Ser. No. 11/253,666, filed Oct. 20, 2005 and U.S. Pat application Ser. No. 11/487,215, filed Jul. 14, 2006, the Examples section of each of which is incorporated herein by reference.

General Techniques for Construction of Anti-CD20 Antibodies

The Vκ (variable light chain) and $V_H$ (variable heavy chain) sequences for anti-CD20 antibodies may be obtained by a variety of molecular cloning procedures, such as RT-PCR, 5'-RACE, and cDNA library screening. Specifically, the V genes of an anti-CD20 MAb from a cell that expresses a murine anti-CD20 MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci., USA,* 86: 3833 (1989)). Based on the V gene sequences, a humanized anti-CD20 MAb can then be designed and constructed as described by Leung et al. (*Mol. Immunol.,* 32: 1413 (1995)).

cDNA can be prepared from any known hybridoma line or transfected cell line producing a murine anti-CD20 MAb by general molecular cloning techniques (Sambrook et al., Molecular Cloning, A laboratory manual, $2^{nd}$ Ed (1989)). The Vκ sequence for the MAb may be amplified using the primers VK1BACK and VK1FOR (Orlandi et al, 1989) or the extended primer set described by Leung et al. (*BioTechniques,* 15: 286 (1993)). The $V_H$ sequences can be amplified using the primer pair VH1BACK/VH1FOR (Orlandi et al., 1989) or the primers annealing to the constant region of murine IgG described by Leung et al. (*Hybridoma,* 13:469 (1994)).

PCR reaction mixtures containing 10 μl of the first strand cDNA product, 10 μl of 10×PCR buffer [500 mM KCl, 100 mM Tris-HCl (pH 8.3), 15 mM MgCl$_2$, and 0.01% (w/v) gelatin] (Perkin Elmer Cetus, Norwalk, Conn.), 250 μM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified Vκ and VH fragments can be purified on 2% agarose (BioRad, Richmond, Calif.). The humanized V genes can be constructed by a combination of long oligonucleotide template syntheses and PCR amplification as described by Leung et al. (*Mol. Immunol.*, 32:1413 (1995)).

PCR products for Vκ can be subcloned into a staging vector, such as a pBR327-based staging vector, VKpBR, that contains an Ig promoter, a signal peptide sequence and convenient restriction sites to facilitate in-frame ligation of the Vκ PCR products. PCR products for $V_H$ can be subcloned into a similar staging vector, such as the pBluescript-based VHpBS. Individual clones containing the respective PCR products may be sequenced by, for example, the method of Sanger et al. (*Proc. Natl. Acad. Sci., USA,* 74: 5463 (1977)).

Expression cassettes containing the Vκ and $V_H$ sequences, together with the promoter and signal peptide sequences, can be excised from VKpBR and VHpBS, respectively, by double restriction digestion as HindIII-BamHI fragments. The Vκ and $V_H$ expression cassettes can be ligated into appropriate expression vectors, such as pKh and pG1g, respectively (Leung et al., *Hybridoma,* 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric, humanized or human anti-CD20 MAb by, for example, an ELISA assay. Alternatively, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al. (*J. Immunol. Methods* 125:191 (1989) and also shown in Losman et al., *Cancer,* 80:2660 (1997)). Another vector that is useful is the GS vector, as described in Barnes et al., *Cytotechnology* 32:109-123 (2000). Other appropriate mammalian expression systems are described in Werner et al., *Arzneim.-Forsch./Drug Res.* 48(II), Nr. 8, 870-880 (1998).

Co-transfection and assay for antibody secreting clones by ELISA, can be carried out as follows. About 10 μg of VKpKh (light chain expression vector) and 20 μg of VHpG1g (heavy chain expression vector) can be used for the transfection of 5×10$^6$ SP2/0 myeloma cells by electroporation (BioRad, Richmond, Calif.) according to Co et al., *J. Immunol.,* 148: 1149 (1992). Following transfection, cells may be grown in 96-well microtiter plates in complete HSFM medium (Life Technologies, Inc., Grand Island, N.Y.) at 37° C., 5% CO$_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis. Transfectoma clones that are positive for the secretion of chimeric, humanized or human heavy chain can be identified by ELISA assay.

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 μl membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by ELISA and its concentration adjusted to about 1 mg/ml using PBS. Sodium azide, 0.01% (w/v), is conveniently added to the sample as preservative.

EXAMPLES

Example 1

Construction of Chimeric and Humanized Anti-CD20 Antibodies

The construction of chimeric (cA20) and humanized (hA20, veltuzumab) anti-CD20 antibodies was performed as described in U.S. Pat. No. 7,151,164, the Examples section of which is incorporated herein by reference. (See also, Stein et al., *Clin Cancer Res* 2004; 10: 2868-2878.) The variable region DNA and amino acid sequences of cA20 and hA20 are disclosed, respectively, in FIG. 1 and FIG. 2.

The CDR sequences of cA20 and hA20 are identical to those of rituximab (parental murine MAb C2B8), with the exception of the third CDR of the heavy chain (CDRH3). For convenience, the heavy chain CDR sequences are referred to as CDRH1-H3 and the light chain CDRs as CDRL1-L3. Of the reported CDRH3 sequences for anti-CD20 antibodies, only C2B8 and the corresponding rituximab have an asparagine residue at Kabat position 101.

The framework region sequences of veltuzumab (hA20) were constructed using the same human IgG donor framework regions (FRs) as the humanized anti-CD22 antibody epratuzumab (Leung et al., *Mol Immunol* 1995; 32: 1413-1427). Specifically, FR1, FR2, and FR3 of the human EU antibody and FR4 of the human NEWM antibody were selected for the heavy chain and the FRs of the human REI antibody were selected for the light chain of the humanized hA20 antibody. As disclosed in U.S. Pat. No. 7,151,164, key murine residues were retained in the FRs to maintain the binding specificity and affinity of veltuzumab for CD20 similar to those of the parental murine antibody. The heavy chain of hA20 (hA20VH1) contains nine changes from the human EU frameworks, while the light chain of hA20 (hA20Vκ) contains seven amino acid changes from the REI framework (U.S. Pat. No. 7,151,164).

A comparison of the variable region sequences of cA20, hA20 and rituximab (from c2B8) is shown in FIG. 3. As indicated in FIGS. 3A and 3B, cA20 differs from veltuzumab (hA20) in the variable framework regions but has identical CDRs as veltuzumab. The framework region sequences of cA20 are identical to those of rituximab (c2B8), with the exception of three amino acid residues at the N-terminal end of the light chain, while the framework region sequences of rituximab and veltuzumab differ at 18 residues in the light chain and 14 residues in the heavy chain. The CDR sequences of rituximab differ from those of veltuzumab (hA20) and cA20 only at Kabat position 101 of the $V_H$ of CDR3.

As described in the following Examples, veltuzumab and rituximab differ significantly with respect to the rate of dissociation from CD20 positive lymphoma cells and in certain therapeutic characteristics in vivo and in vitro. To determine whether or not these changes in characteristics were attributable to the differences in framework sequence or the substitution of Asp for Asn at Kabat position 101 of CDR3's $V_H$, a mutant of veltuzumab, designated D101N, was engineered with a non-conservative single amino acid change of aspartic acid to asparagine at position 101 in CDRH3. Thus, D101N has the same CDRs as rituximab but identical FRs to veltuzumab. Further details of the construction of D101N are provided below. Table 1 compares the CDRH3 sequences of veltuzumab, cA20, D101N, rituximab, and 1F5, all of which have identical CDRH1 and CDRH2 sequences.

TABLE 1

Comparison of CDRH3[1]

| | SEQ ID NO: | Kabat numbering | | | | | | | | | | | |
|---|---|---|---|---|---|---|---|---|---|---|---|---|---|
| | | 95 | | | | | 100 | | | | | 101 | 102 |
| Veltuzumab | 6 | S | T | Y | Y | G | G | — | D | W | Y | F | D | V |
| D101N | 32 | • | • | • | • | • | • | — | • | • | • | • | N | • |
| cA20 | 6 | • | • | • | • | • | • | — | • | • | • | • | • | • |
| Rituximab | 32 | • | • | • | • | • | • | — | • | • | • | • | N | • |
| 1F5 | 33 | • | H | • | G | S | N | Y | V | D | • | • | • | Y |

[1]Residues marked as • are identical to those of veltuzumab in the same position.

Example 2

Construction of D101N Sequence Variant of Veltuzumab

All restriction endonucleases and other enzymes were purchased from New England Biolabs (Beverly, Mass.). Oligonucleotides were synthesized by Sigma Genosys (Haverhill, UK). PCR reactions were performed using Amplitaq polymerase (Applied Biosystems, Foster City, Calif.) and a Perkin Elmer (Wellesley, Mass.) GeneAmp PCR system 9600. Two PCR reactions using hA20-pdHL2 (see U.S. Pat. No. 7,151,164) vector as a template and the oligonucleotide primer pairs of 5' D101N (cggtgactggtacttcaatgtctggggccaaggcaccacg SEQ ID NO:17) and 3' Hind3 (aaagcttgcggccgcgatcc SEQ ID NO:18) or 3' D101N (cgtggtgccttggccccagacattgaag taccagtcaccg SEQ ID NO:19) and 5' XhoI (cctcgagcacacaggacctc SEQ ID NO:20) produced 210 bp or 510 bp amplimers, respectively. A third PCR reaction using a mixture of the 210 bp and 510 bp products as template and the 5' XhoI and 3' Hind3 primers produced a 680 bp amplimer, which was gel isolated and cloned into the pGemT PCR cloning vector (Promega, Madison, Wis.). The sequence of the amplimer was confirmed by automated DNA sequencing. The 680 bp fragment was excised from the pGemT vector with XhoI and Hind III restriction enzymes and ligated into the hA20-pdHL2 vector, which was prepared by digestion with the same enzymes. The sequence of the final vector, D101N-hA20-pdHL2, was confirmed by automated DNA sequencing.

Example 3

Scatchard Analysis of Binding of Anti-CD20 Antibodies

Cell Lines

In the following Examples, the murine hybridoma 1F5 and the human Burkitt lymphoma lines, Daudi, Raji and Ramos, were purchased from the American Type Culture Collection (Manassas, Va.). The non-Burkitt lymphoma cell lines used were: SU-DHL-6 from Dr. Alan Epstein (University of Southern California, Los Angeles, Calif.), and WSU-FSCCL from Dr. Mitchell Smith (Fox Chase Cancer Center, Philadelphia, Pa.). The cells were grown as suspension cultures in DMEM (Life Technologies, Inc. Gaithersburg, Md.), supplemented with 10% fetal bovine serum, penicillin (100 units/ml), streptomycin (100 µg/ml), and L-glutamine (2 mM).

Scatchard Analysis

The maximum number of binding sites per Raji cell and the apparent dissociation constants of veltuzumab and rituximab were determined by nonlinear regression analysis of the saturation binding data obtained with the radioiodinated samples and Raji cells, using Prism software (GraphPad Software Inc., San Diego, Calif.). Raji cells ($5 \times 10^5$) were incubated with radioiodinated MAbs in an assay volume of 225 µl, using tissue culture media as diluent, for 1 h at 37° C. or room temperature. Cells then were washed twice with PBS containing 1% horse serum, and cell pellets were counted in a gamma counter. The MAbs were titrated at a 2:3 serial dilution starting with approximately $2 \times 10^6$ cpm/2 µg MAb/tube, run in triplicate. Non-specific binding was measured by including replicate unlabeled MAb. Immunoreactivity of the radiolabeled MAbs, measured by binding to anti-idiotype antibodies, was 90% or greater.

The results shown in FIG. 4 demonstrate that both the number of binding sites per cell and the equilibrium dissociation constants (functional $K_d$) were similar for veltuzumab and rituximab. The number of binding sites per Raji cell was calculated to range from $2.0 \times 10^5$-$4.2 \times 10^5$ for veltuzumab versus $1.8 \times 10^5$-$3.6 \times 10^5$ for rituximab. In replicate assays, the apparent dissociation constant values ranged from 6.23-12.02 nM for veltuzumab versus 6.70-8.63 nM for rituximab. These values are similar to those reported previously by ourselves and others, as well as in the prescribing information for rituximab (Melhus et al., Cancer Biother. Radiopharm., 22: 469-479, 2007; Stein et al., Clin. Cancer Res., 10: 2868-2878, 2004).

Example 4

Competitive Cell Surface Binding Assay

Ag (Antigen)-binding specificity and affinity studies of the anti-CD20 Abs cA20, hA20, and c1F5, purified by affinity chromatography on a Protein A column were evaluated by a cell surface competitive binding assay with murine 2B8 and rituximab (IDEC Pharmaceuticals Corp., San Diego, Calif.). A constant amount (100,000 cpm, ~10 µCi/µg) of $^{125}$I-labeled m2B8 or rituximab was incubated with Raji cells in the presence of varying concentrations (0.2-700 nM) of competing Abs (cA20, hA20, m$^2$B8, c1F5, or rituximab) at 4° C. for 1-2 h. Unbound Abs were removed by washing the cells with PBS. Radioactivity associated with the cells was determined after washing. The results (not shown) demonstrated that cA20, hA20 and cIF5 all competed for binding to CD20 with rituximab (c2B8) and murine 2B8.

Example 5

Comparison of Dissociation or Off-Rates

Figure 5:
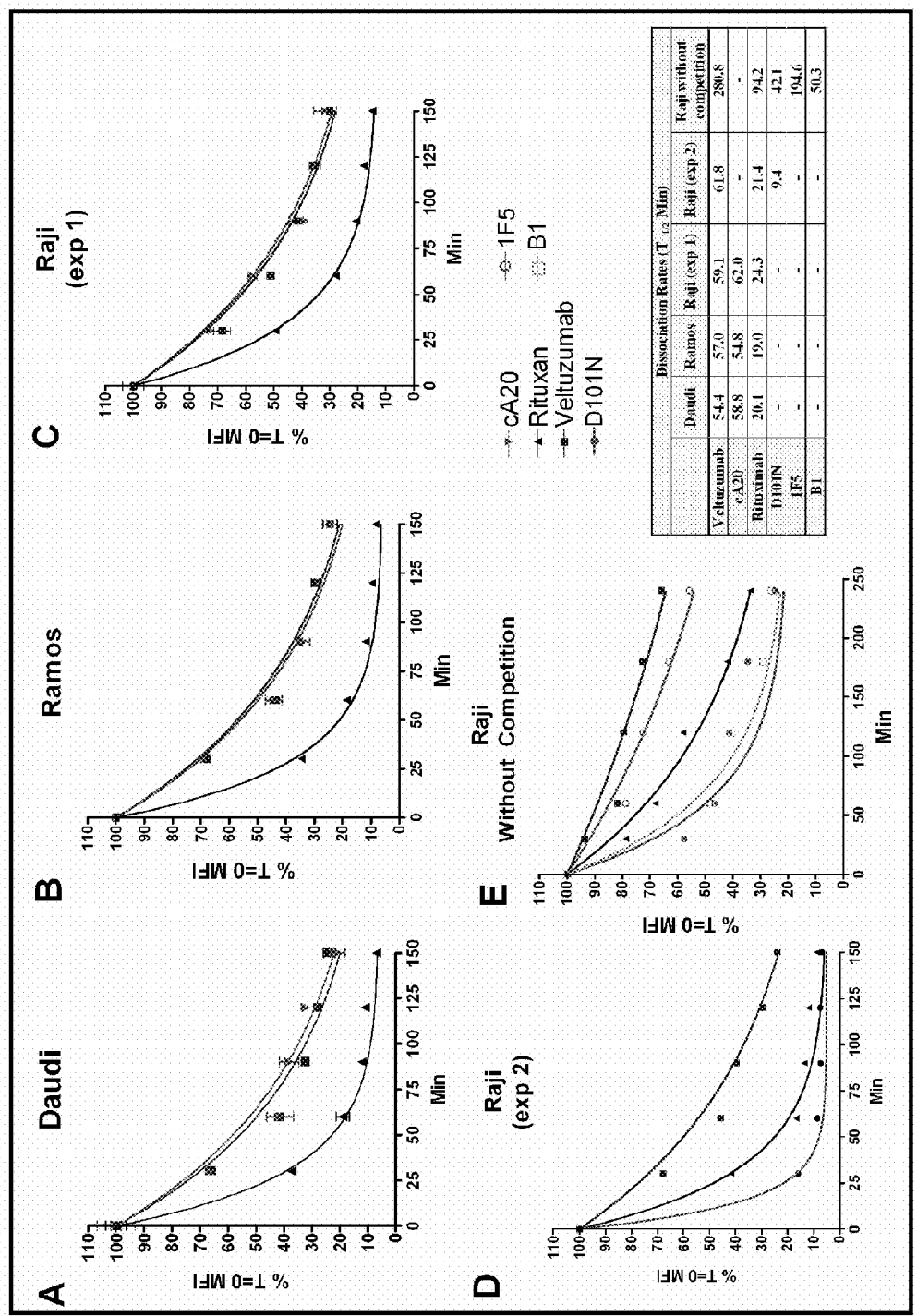
FIG. 5. Comparison of dissociation rates of veluzumab and rituximab from live cells. Daudi (A), Ramos (B), and Raji (C-E) cells were stained with PE-labeled rituximab (closed triangle), veluzumab (closed square), cA20 (upside down closed triangle), D101N (closed circle), 1F5 (open circle) or BI (tositumomab) (open square). The labeled MAbs were incubated at 37° C. with (A-D) or without (E) excess veluzumab Fab'-NEM and the cells analyzed by flow cytometry over time. The off-rate was determined by non-linear regression (one phase exponential decay) and P-values were generated by F-test using GraphPad Prism software.

The dissociation rates of veltuzumab, rituximab, cA20, D101N, 15F and tositumomab (anti-CD20, BEXXAR®, GlaxoSmithKline) were compared by flow cytometry using Daudi, Raji and Ramos cells (FIG. 5). Each MAb was labeled with phycoerythrin (PE) using a Zenon R-Phycoerythrin Human IgG labeling kit following the manufacturer's suggested protocol (Invitrogen, Molecular Probes, Z-25455). Cells (Daudi, Raji, or Ramos) in 0.5 mL of CM (phenol red-free RPMI 1640 media supplemented with 10% FBS) at $1 \times 10^6$ cells/mL were incubated with 5 µg of each PE-labeled MAb at room temperature for 30 min, pelleted at 400×g, washed twice with CM, resuspended in 1.5 mL of CM, and split into two 0.75-mL aliquots. To prevent rebinding, N-ethyl-maleimide (NEM)-blocked veltuzumab-Fab' was added to each replicate (1 mg/mL final concentration) and the mean fluorescence intensity (MFI) was immediately measured to determine the maximal binding (T=0) using a Guava PCA and Guava Express software (Guava Technologies, Inc., Hayward, Calif.). Subsequent measurements were taken at 30-min intervals. The percent maximal binding, which is the quotient of the MFI at T=X divided by that at T=0, was plotted against time, and the results analyzed by Prism software (GraphPad Software Inc., San Diego, Calif.) to yield the half-life or off-rates.

The dissociation rates of veltuzumab, rituximab and cA20 from Daudi (FIG. 5A), Ramos (FIG. 5B) and Raji (FIG. 5C) cells were compared in the presence of excess veltuzumab-Fab'-NEM at 37° C. Additional measurements were performed to compare the dissociation of veltuzumab, rituximab, and D101N from Raji cells (FIG. 5D) under similar conditions. For each cell line tested, the half-life of veltuzumab on average was 2.7-fold (±0.3) longer than that of rituximab (P<0.0001), but indistinguishable from that of cA20 (P>0.2). In contrast, the D101N mutant dissociates from Raji cells with an off-rate two- and six-fold faster than rituximab and veltuzumab, respectively. These results indicate that the change of $Asn_{101}$ to $Asp_{101}$ is responsible for the slower dissociation of veltuzumab. We also compared the dissociation of veltuzumab, rituximab, D101N, 1F5, and tositumomab from Raji cells (FIG. 5E) in the absence of the competing veltuzumab-Fab'-NEM, and found that veltuzumab has the longest half-life (281 min), followed by 1F5 (195 min), rituximab (94 min), tositumomab (50 min), and D101N (42 min).

Example 6

In-Vitro Cell Proliferation Inhibition by MTT Assay

The in-vitro cytotoxicity assay was based on the method of Mosmann (J Immunol Methods, 65: 55-63, 1983). Briefly, cell lines were plated at $1-2 \times 10^4$ cells/well (100 µl) in 96-well plates, to which antibodies were added (100 µl). After incubation for 4 days at 37° C. in a humidified $CO_2$ (5%) incubator, 25 µl of 5.0 mg/ml MTT [3-(4,5-dimethylthiazol-2-yl)-2,5-diphenyltetrazolium bromide] was added, and the cells were incubated for an additional 4 h at 37° C. Plates were then centrifuged and supernatants removed. Pellets were dissolved using 100 µl DMSO/well and optical density was measured at 570 nm on a microplate reader (Molecular Devices, Sunnyvale, Calif.). Because unlabeled rituximab and veltuzumab were reported previously to require crosslinking for cytotoxic activity (Stein et al., Blood, 104: 3705-3711, 2004), goat-anti-human IgG (GAH) was added to some of the wells. Veltuzumab and rituximab were used at a final concentration of 5 µg/ml and GAH was used at 20 µg/ml. All tests were performed in 4 replicates.

Figure 6:
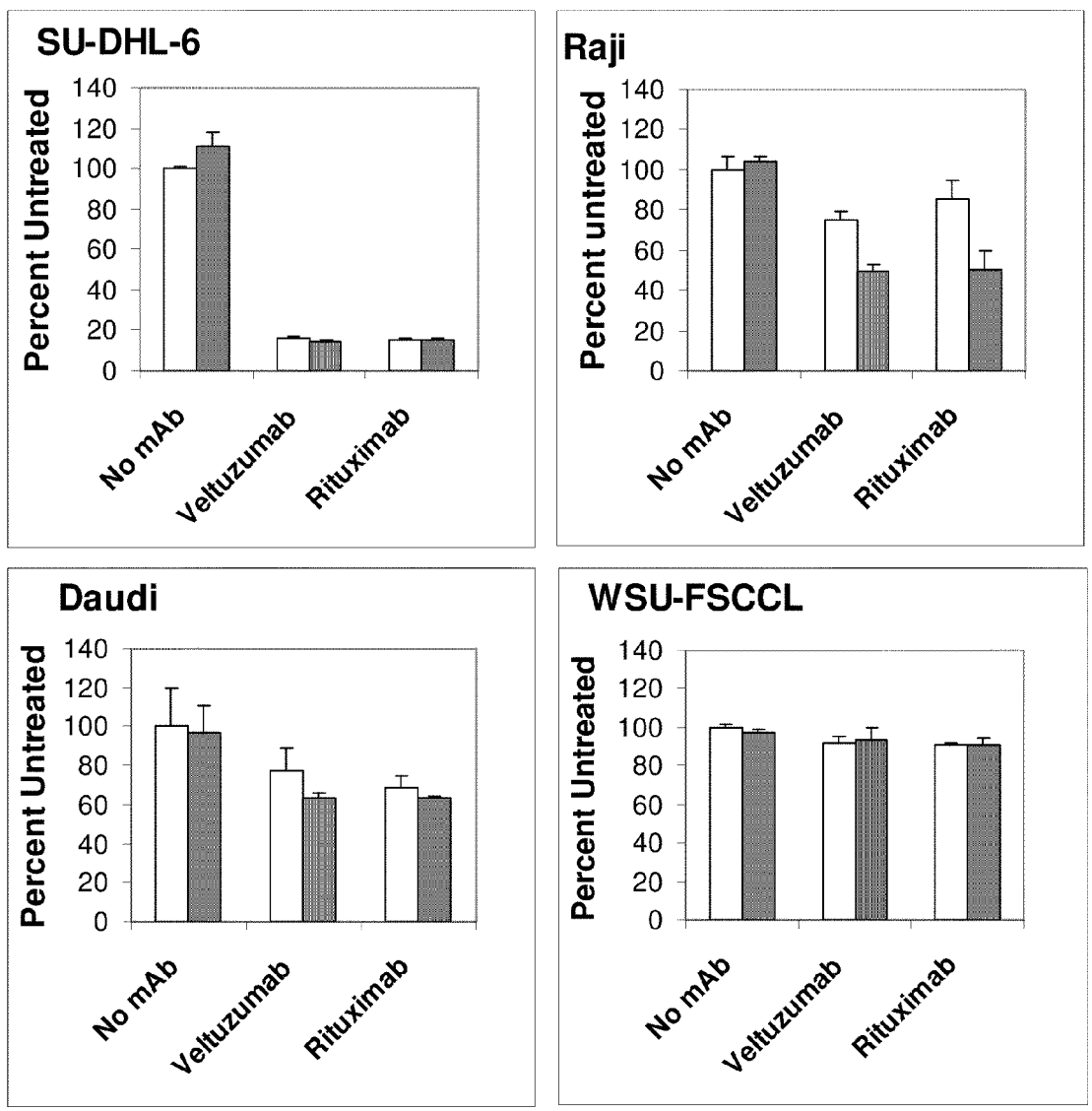
FIG. 6. Effects of veluzumab and rituximab on proliferation of non-Hodgkin's lymphoma cell lines. Anti-proliferative effects were assessed by MTT cytotoxicity assays. Cells were cultured with the MAbs with or without a second antibody for crosslinking. White bars, no second antibody; gray bars with GAH second antibody; error bars, SD.

The ability of veltuzumab and rituximab to inhibit proliferation was examined using MTT cytotoxicity assays on four lymphoma cell lines, SU-DHL-6, Daudi, Raji, and WSU-FSCCL, which differ in their expression levels of CD20 (Stein et al., Clin Cancer Res, 10: 2868-2878, 2004). While the sensitivity to both MAbs correlated with CD20 expression (SU-DHL-6>Raji>Daudi>WSU-FSCCL), no significant differences in potency were observed between veltuzumab and rituximab within a cell line (FIG. 6). Crosslinking with second antibody (GAH, goat anti-human IgG) increased the efficacy of veltuzumab and rituximab on Raji and Daudi cells, two cell lines with intermediate levels of CD20 expression and sensitivity to killing by anti-CD20 MAbs (FIG. 6). Inhibition of proliferation of cell lines on either extreme of anti-CD20 sensitivity (e.g., SU-DHL-6, which is very sensitive, and WSU-FSCCL, which is very insensitive) did not benefit by the addition of second antibody (FIG. 6).

Example 7

B- and T-Cell Depletion in Vitro

Figure 7:
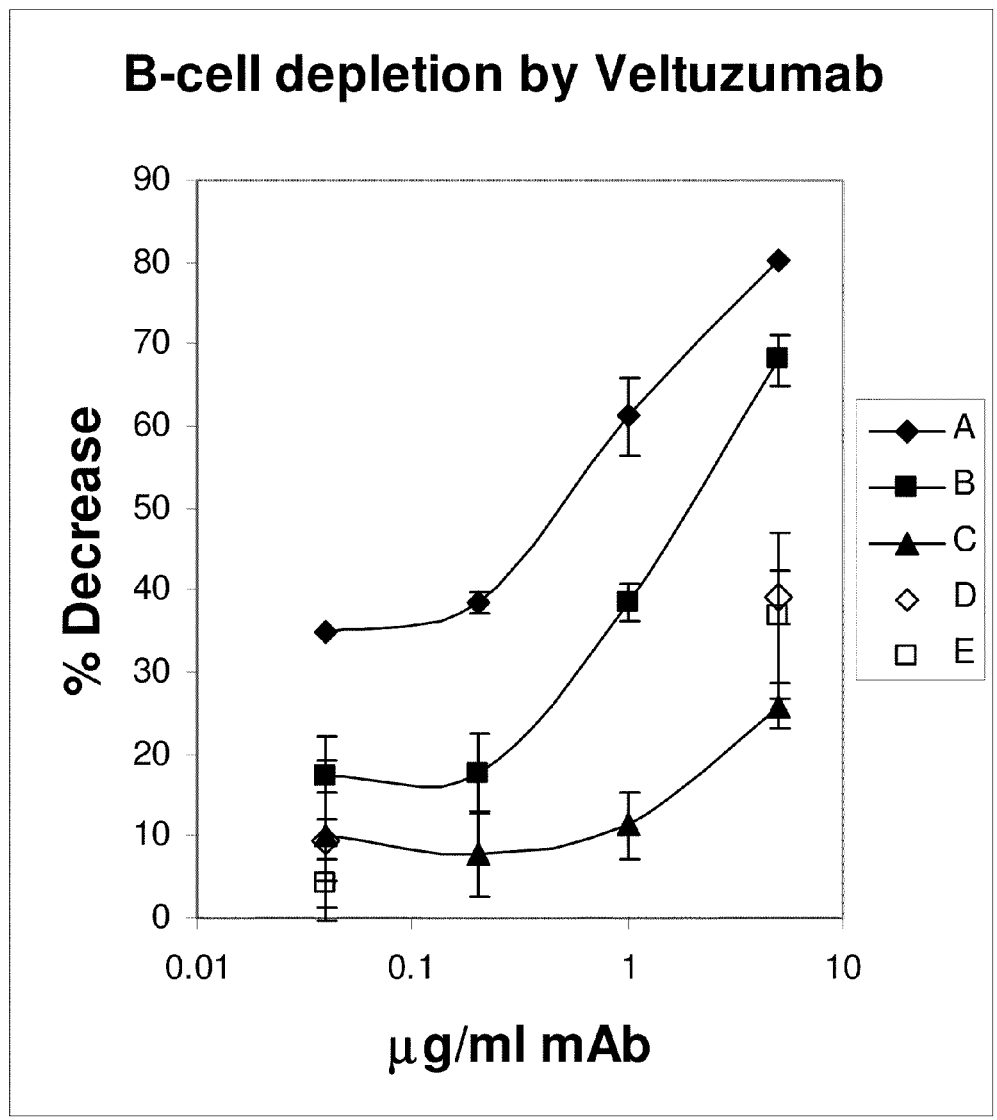
FIG. 7. In vitro depletion of B-cells from healthy blood donors. The effect of veluzumab on peripheral blood lymphocytes from healthy volunteers was evaluated in vitro using flow cytometry. Decrease in the percent of CD19+ cells present in the lymphocyte gate after a two-day incubation of heparinized whole blood of healthy volunteers with veluzumab is shown. Each line represents a different blood donor. Error bars, SD.

The effects of veltuzumab on human peripheral blood lymphocytes of healthy volunteers were assessed in vitro using flow cytometry. Aliquots of whole blood were incubated with veltuzumab for two days followed by analysis of B-cells (CD19+) and T-cells (CD3+) by FACS. Controls included no antibody and a negative control humanized MAb (anti-CEACAM5 monoclonal antibody, hMN-14). Incubation of whole blood with veltuzumab led to significant decreases in the number of B-cells, but not T-cells (FIG. 7). Decreases of B-cells ranged from 26-80% using 5 µg/ml, and 11-61% using 1 µg/ml (P values vs. untreated cells<0.05 with 1 µg/ml [6.7 nM] for 3/3 blood donors and 5 µg/ml [33.3 nM] for 5/5 blood donors). Because whole blood was used in the incubation mixtures, the decreases observed in the cell counts could be due to CDC or ADCC, as well as direct signaling.

Example 8

Complement-Dependent Cytotoxicity (CDC) Assays

A fluorometric method was used to evaluate and compare CDC activity of veltuzumab vs. rituximab. Daudi, Raji or Ramos cells ($1 \times 10^6$/mL) were seeded (50 µL per well) in black 96-well plates (Nunc) and incubated for 3 h at 37° C. and 5% $CO_2$ with each test MAb (0.001 to 10 µg/mL) in the presence of human complement (Quidel Corp., San Diego, Calif.) at 1/20 final dilution. The indicator dye, AlamarBlue (BioSource, Camarillo, Calif.), was added and the incubation continued overnight. Viable cells were then quantified by measuring the fluorescence intensity with excitation at 530 nM and emission at 590 nM using a BioTek Synergy™HT Multi-Detection Microplate Reader and KC4 Signature Software (BioTek Instruments, Inc., Winooski, Vt.).

The dose-response curves generated from the mean of 6 replicate determinations were analyzed using Prism software to obtain $EC_{50}$ values. In the case of Daudi cells, to account for day-to-day variations in the assay, as well as to increase the precision of the $EC_{50}$ estimates, the experiments used a multi-factorial design, where the assay for each antibody was performed in triplicate each day, and repeated on three different days for a total of 9 assays per antibody. The samples included 3 different lots of veltuzumab and one of rituximab. Statistical analysis of the $EC_{50}$ data was based on a 2-way analysis of variance (ANOVA) model with day and antibody type as factors. Dunnett's multiple comparison procedure was utilized to perform the 3 comparisons of all 4 constructs at an overall experimental error rate of 0.05.

With Daudi as the target cells for CDC, we observed consistently a lower value of $EC_{50}$ for veltuzumab (Table 2) when compared to rituximab. Further measurements addressing any effect of day-to-day variation as well as any differences in $EC_{50}$ patterns amongst the antibodies across different days indicated that the mean difference in $EC_{50}$ observed between rituximab and each of the three lots of veltuzumab was consistently statistically significant (P<0.0001). However, no differences between veltuzumab and rituximab were observed with CDC results in the other two cell lines, Raji and Ramos.

TABLE 2

Comparison of Veltuzumab versus Rituximab: Summary of CDC Results ($EC_{50}$) in the Daudi cell line.

| Antibody | No. of Experiments (N) | $EC_{50}$ (g/mL) Mean ± Std. Dev. | Mean Difference (Vmab-Rmab) | 95% Confidence Interval [1] |
|---|---|---|---|---|
| Rituximab | 9 | 0.1485 ± 0.0200 | | |
| Veltuzumab (Lot 1) | 9 | 0.0990 ± 0.0232 | −0.0495 | (−0.0611, −0.0378) |
| Veltuzumab (Lot 2) | 9 | 0.0843 ± 0.0215 | −0.0642 | (−0.0758, −0.0525) |
| Veltuzumab (Lot 3) | 9 | 0.0904 ± 0.0239 | −0.0581 | (−0.0697, −0.0464) |

[1] Based on 2-way ANOVA model adjusted for multiple comparisons using Dunnett's method.

Example 9

Antibody-Dependent Cellular Cytotoxicity (ADCC) Assays

Induction of ADCC was measured using peripheral blood mononuclear cells (PBMCs) and Daudi as effector and target cells, respectively. Daudi cells were incubated with each test antibody in triplicate at 5 μg/mL for 30 min at 37° C. and 5% $CO_2$. Freshly isolated peripheral blood mononuclear cells (PBMCs) obtained from healthy volunteers were then added at a predetermined optimal effector-to-target ratio of 50:1. Following a four hour incubation, cell lysis was assessed by CytoTox-One (Promega, Madison, Wis.). ADCC was determined for MAb+effector cells, MAb+target cells, and MAb+target cells+effector cells. Control wells containing MAb alone and target cells alone also were processed.

To evaluate the results, the mean background value obtained from wells with media alone was subtracted from all other wells, and the % lysis was calculated using the following equation in which MET represents wells containing MAb, effector and target cells; ET is wells containing effector and target cells; T, wells containing target cells only; and Max is wells containing target cells and lysis buffer:

$$\% \text{ Lysis} = \frac{MET - ET}{\text{Max} - T} \times 100.$$

The level of ADCC activity of five lots of veltuzumab was compared to those of rituximab and a negative control MAb (hMN-14) by measuring cytolysis of the CD20-expressing Daudi cell line. Effector cell function was provided by PBMCs freshly isolated from two volunteer blood donors. The results indicated that rituximab and each of the 5 lots of veltuzumab produced statistically similar (P=0.12) levels of ADCC (40-45% lysis) (data not shown). Rituximab and veltuzumab both showed significantly higher levels of ADCC (P<0.0001) compared to the control MAb (9.9% lysis, humanized anti-CEA labetuzumab).

Example 10

Effects of Natural Killer (NK) Cell and Neutrophil Depletion on Therapy

Depletion of NK cells and neutrophils was performed as described previously (Hernandez-Ilizaliturri et. al., Clin Cancer Res 9:5810-12, 2003). Briefly, each mouse received 100 μL of anti-mouse Gr-1 ascites i.p. (provided by Dr. F. J. Hernandez-Ilizaliturri, Roswell Park Cancer Institute, Buffalo, N.Y.) and 100 μg anti-mouse IL-2 receptor antibody (TMβ-1, BD PharMingen, Inc., San Jose, Calif.) one day before inoculating $1 \times 10^6$ Raji cells, followed by two more i.p. injections of anti-mouse Gr-1 ascites on Days 6 and 13. Depletion was confirmed by FACS analysis of blood samples taken from 1 depleted and 1 non-depleted mouse on Days 3 and 13. Veltuzumab (200 μg) or saline was administered i.v. on Days 3, 5, 7, and 11.

Figure 11:
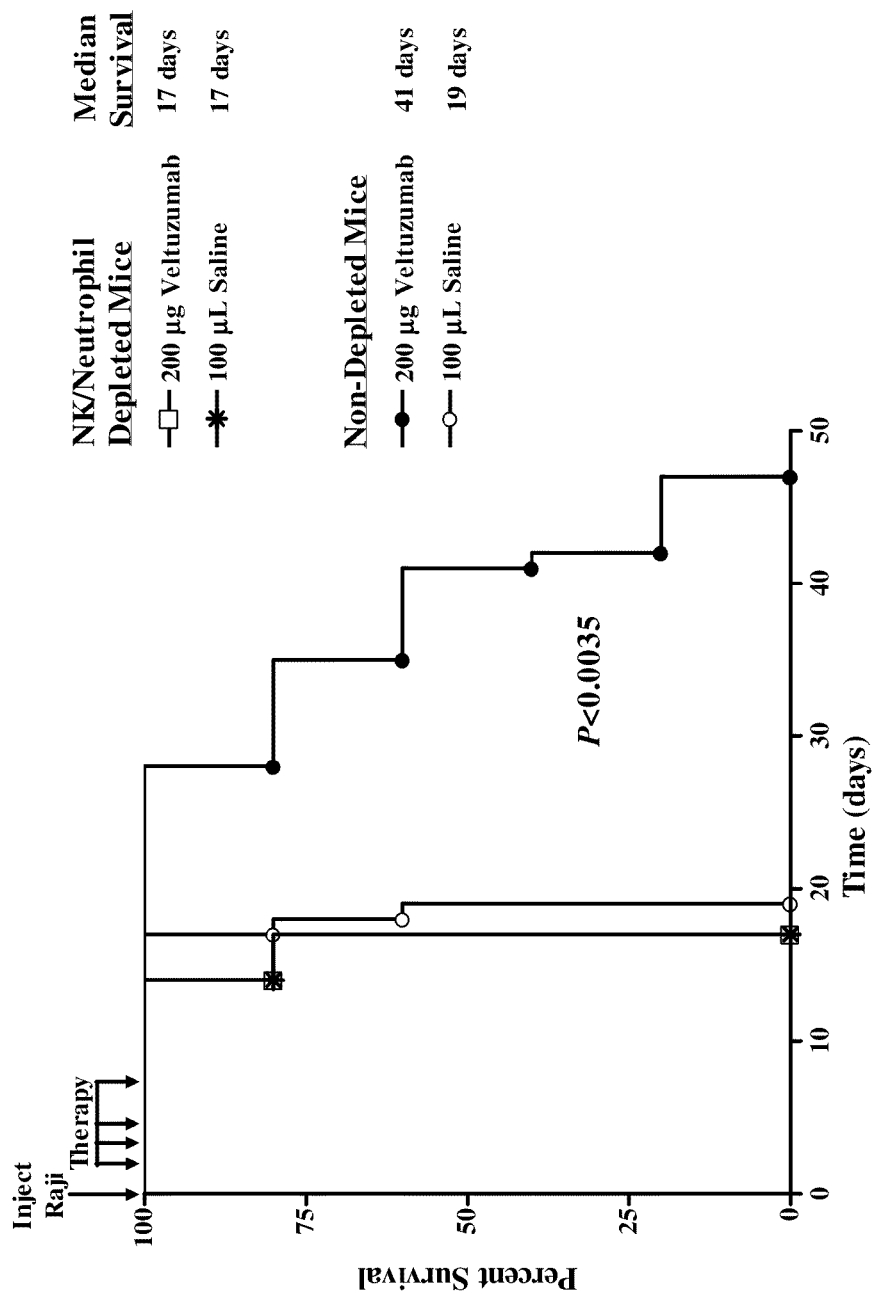
FIG. 11. The effect of depleting NK cells and neutrophils on anti-lymphoma activity was assessed in SCID mice. C.B. 17 SCID mice were depleted of NK and neutrophils as described in the Methods section and injected with $1 \times 10^6$ Raji cells i.v. Therapy with veluzumab began on day 3 with mice receiving 200 µg veluzumab i.v. on days 3, 5, 7, and 11. Control mice received 100 µL saline.

The role of effector cells on veltuzumab's inhibition of Raji tumor growth in vivo was examined (FIG. 11). In those animals depleted of NK and neutrophils, there was no difference between saline control and treated mice, both having the same MST (16.4±1.3 days). In contrast, in the non-depleted mice, veltuzumab-treated mice had a significantly improved MST over the saline controls (38.6±7.3 vs. 18.4±0.9 days; P<0.0035).

Example 11

Analysis of Serum Pharmacokinetics in Mice after i.p. or s.c. Administration.

Twelve 9-week-old naïve female Swiss-Webster mice (Taconic Farms; Germantown, N.Y.) were weighed prior to injection and grouped six to a cage such that the mean and standard deviations between the two sets of mice were not significantly different. Veltuzumab, 1 nmole (150 μg), was administered either as a 200 μL i.p. or s.c. injection. Serum samples were taken by retro-orbital bleeding at 0.5, 1, 4, 6, 24, 48, 120, 168 and 336 h and stored frozen until analysis for veltuzumab.

A capture ELISA was used to quantify the amount of veltuzumab in the serum samples. A 96-well assay plate (Nunc Maxisorp Certified Flat-Bottom Immuno Modular w/frame; NalgeNunc International Corp., Rochester, N.Y.) was coated with a rat anti-veltuzumab idiotype monoclonal antibody, WR2 (Immunomedics, Inc., Morris Plains, N.J.). A standard curve was constructed by making 8 serial dilutions of veltuzumab (100 to 1.56 ng/mL). The murine serum samples were appropriately diluted and, together with the standards, pipetted into triplicate wells. Bound veltuzumab was detected with a peroxidase-conjugated goat anti-human polyclonal antibody (Jackson ImmunoResearch Laboratories, Inc., West Grove, Pa.), and the plates developed using an OPD solution (o-phenylenediamine dihydrochloride, Sigma-Aldrich, St. Louis, Mo.). The plates were incubated in the dark until the color developed in the standard curve wells (~20 min). At this time, 4N sulfuric acid was added to the wells to stop the reaction, and the plates read on a plate reader at $OD_{490}$ nm.

Using Prism software (GraphPad Software, Inc.), the concentration of veltuzumab was calculated in the mouse serum samples based on the standard curve. To ensure accuracy, each sample was run multiple times and the mean value from all these runs was used in the PK-analysis. Plasma concentrations that were determined from the above assay were converted to nmol/mL and analyzed using the WinNonLin PK software package (v5.1, Pharsight Corp., Mountain View, Calif.). Non-compartmental analysis was performed on both the i.p. and s.c. data (representing the best-fit model).

Figure 12:
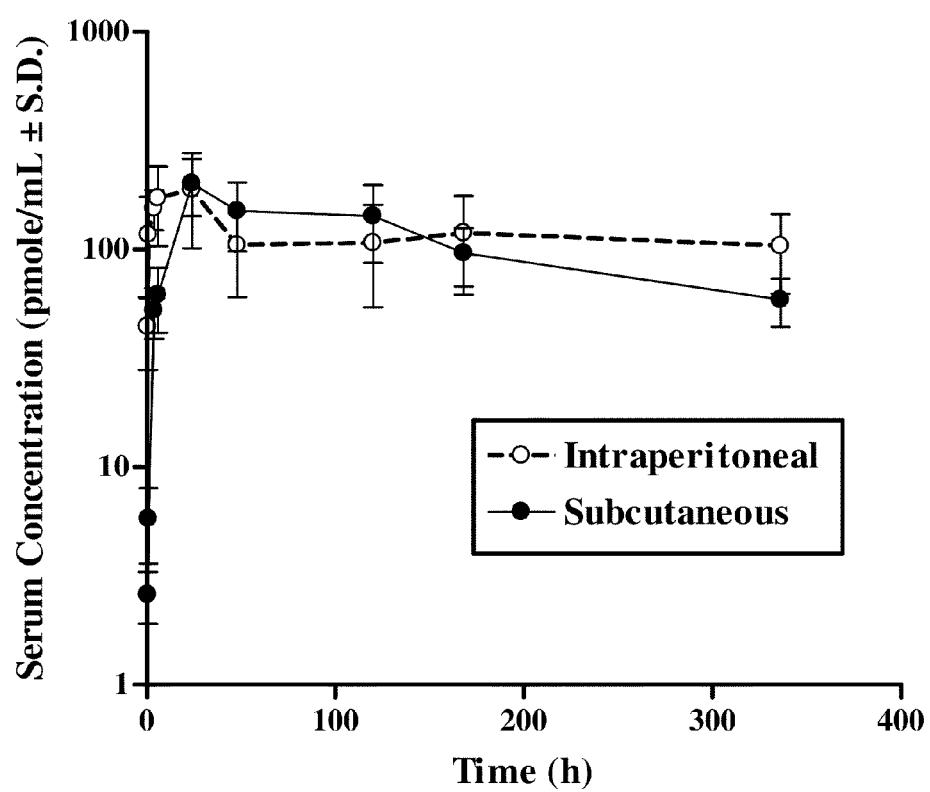
FIG. 12. Serum pharmacokinetics—veluzumab (150 µg) was administered to naive Swiss-Webster mice either via the i.p. or s.c. route. Animals were bled over a 14-day period and serum was assayed for veluzumab concentrations as described in Example 11 (N=6).

While serum concentrations and clearance of veltuzumab were very similar between those animals injected i.p. versus s.c. (FIG. 12), several of their respective PK-parameters were significantly different (Tables 3 and 4). In terms of maximum serum concentrations ($C_{max}$) and the time to $C_{max}$ ($T_{max}$), there were no significant differences between the injection routes. This was also true for comparisons between clearance (Cl) and area under the curve (AUC) values. However, notable differences were observed in the terminal half-life ($T_{1/2}$) and mean residence time (MRT), with the i.p. route yielding significantly higher values for each (P=0.0316 and P=0.0357, respectively).

TABLE 3

Pharmacokinetics of hA20 with Intraperitoneal Injection
Individual Mouse Serum PK of hA20 IgG Administered as a Single Intraperitoneal Injection.

| Animal No. | Injected Dose (pmoles) | $C_{max}$ (pmole/mL) | $T_{max}$ (h) | $T_{1/2}$ (h) | $AUC_{0 \to \infty}$ (h * pmole/mL) | Cl (mL/h) | $MRT_{0 \to \infty}$ (h) |
|---|---|---|---|---|---|---|---|
| 1 | 1000 | 143.7 | 24 | 308.5 | 86,170 | 0.0116 | 540.8 |
| 2 | 1000 | 173.9 | 24 | 225.9 | 54,204 | 0.0184 | 379.2 |
| 3 | 1000 | 229.8 | 24 | 846.1 | 214,007 | 0.0047 | 1219.5 |
| 4 | 1000 | 246.5 | 24 | 562.8 | 149,725 | 0.0067 | 840.1 |
| 5 | 1000 | 76.5 | 24 | 292.8 | 28,628 | 0.0349 | 439.6 |
| 6 | 1000 | 296.7 | 24 | 333.0 | 107,101 | 0.0093 | 500.8 |
| Mean | | 195 | | 428 | 106,639 | 0.0143 | 653 |
| (Stdv) | | (79) | | (235) | (67,288) | (0.0112) | (320) |

The tumor-free Swiss-Webster mice used in our PK study weighed an average of 30 g. Whole blood volume in mice is estimated based on their weight and uses a range of 5.5 to 7% of body weight as mL of whole blood. If we use an average of 6.25%, our mice had approximately 1.9 mL whole blood of which approximately 50% is serum or 0.95 mL. We injected 150 μg into these mice i.p., so if all of it ended up in the blood we would have a serum concentration of approximately 158 μg/mL. We found that after injecting 150 μg of veltuzumab into these 30 g mice, we achieved a $C_{max}$ of 30 μg/mL serum, or 5.3-fold less than what could be maximally expected.

TABLE 4

Pharmacokinetics of hA20 with Subcutaneous Injection
Individual Mouse Serum PK of hA20 IgG Administered as a Single Subcutaneous Injection.

| Animal No. | Injected Dose (pmoles) | $C_{max}$ (pmole/mL) | $T_{max}$ (h) | $T_{1/2}$ (h) | $AUC_{0 \to \infty}$ (h * pmole/mL) | Cl (mL/h) | $MRT_{0 \to \infty}$ (h) |
|---|---|---|---|---|---|---|---|
| 1 | 1000 | 227.2 | 24 | 166.1 | 45,734 | 0.0219 | 261.3 |
| 2 | 1000 | 256.1 | 24 | 173.4 | 55,139 | 0.0181 | 265.4 |
| 3 | 1000 | 172.7 | 24 | 244.9 | 66,351 | 0.0151 | 355.9 |
| 4 | 1000 | 204.1 | 24 | 189.7 | 58,214 | 0.0172 | 278.4 |
| 5 | 1000 | 195.5 | 24 | 162.5 | 41,018 | 0.0244 | 247.9 |
| 6 | 1000 | 162.6 | 24 | 185.0 | 43,580 | 0.0229 | 280.3 |
| Mean | | 203 | | 187 | 51,673 | 0.0199 | 282 |
| (Stdv) | | (35) | | (30) | (9,844) | (0.0037) | (38) |

Using the above observations, we injected 50 ng (0.05 μg) into ~20-g SCID mice for our lowest therapy dose. Based on their weight, they should have approximately 1.14 mL whole blood volume, of which 0.57 mL is serum. If all 50 ng resided in the blood, there would be a serum concentration of 87.7 ng/mL. Given the same kinetics as observed in the normal mouse PK studies, we estimate a $C_{max}$ concentration of approximately 16.5 ng/mL veltuzumab in the serum (87.7 ng/mL divided by 5.3). This does not take into account the presence of Daudi cells that can be an antigen sink in these mice, and thus lower the serum concentration.

Example 12

Tolerability and Toxicokinetics in Cynomologus Monkeys

An exploratory single- and repeated-dose study of intravenous and s.c. injections of veltuzumab was conducted in cynomolgus monkeys (Macaca fascicularis) at SNBL USA, Ltd. (Everett, Wash.). Sixteen male and 16 female monkeys weighing 2.5 to 6.6 kg (3-7 years old) were given i.v. or s.c. doses of 0, 6.7, 33.5, and 67 mg/kg (which correspond to 80, 375, and 800 mg/m$^2$ doses, respectively, in humans), either once or three times (2 weeks apart). The monkeys were examined regularly, with blood sampling taken for MAb titers and PK, blood chemistry, coagulation, and hematology testing, as well as urinalysis, and then postmortem evaluation of lymphoid tissue status in spleen, mandibular, and mesenteric lymph nodes.

Veltuzumab administered i.v. or s.c. as single or multiple doses was well tolerated, with no clinical or persistent laboratory test abnormalities noted other than B-cell depletion in the circulation and lymphatic organs. Post-mortem changes in the animals receiving all doses included follicular lymphoid depletion of the spleen, mandibular, and mesenteric lymph nodes at all doses (data not shown). Transient decreases in white blood cells, neutrophils, lymphocytes, and basophils were noted, but only a rapid and persistent reduction in the number of peripheral blood B-cells was observed (not shown). These effects occurred within 2 days of dosing by either route and were present at doses of 6.7 mg/kg or higher. The animals recovered at either 28 days when treated once, or at 56 days when given 3 doses. Pharmacokinetic analyses (data not shown) indicated that the half-life was estimated at 5 to 8 days after i.v. injection or 6-13 days following s.c. administration, and the $T_{max}$ for both routes ranged from 2 to 5 days. $C_{max}$ following i.v. injection was linear and showed no accumulation, and the $AUC_{0-27}$ days was greater for i.v. administration than for the s.c. route (not shown). This is likely related to the longer period required for the MAb to enter the blood stream via the s.c. route with a similar rate of clearance. The dose-normalized AUC values showed accumulation of veltuzumab after i.v.-infusion or s.c. administration at all dose levels, but the mean volume of distribution was greater after s.c. administration than after i.v. infusion at all dose levels (not shown). These results indicate that at the lowest single dose of 6.7 mg/kg (equivalent to 80 mg/m$^2$ in humans), rapid depletion of peripheral and splenic B-cell depletion occurs for veltuzumab given either by i.v. and s.c. routes at this low dose.

Example 13

In-Vivo Efficacy of Veltuzumab in Mouse Models

These studies were performed in C.B.17 homozygous severe combined immune deficient (SCID) mice of approximately 20 grams (7-week-old when received from Taconic, Germantown, N.Y.). For the Daudi (Burkitt's lymphoma) model, mice were inoculated i.v. on Day 0 with 1.5×10$^7$ cells, weighed, and randomly assigned to six treatment and two control groups (8 per group). On Day 1, mice in a treatment group received a single dose of veltuzumab (5, 20, or 60 µg) s.c. or i.p., and those in the control groups received either saline (200 µL) or 60 µg of a non-Daudi targeting isotype-matched anti-CEACAM5 monoclonal antibody, hMN-14 IgG (labetuzumab, Immunomedics, Inc., Morris Plains, N.J.).

In addition to this study, a minimal effective dose experiment was performed in the same Daudi model. Groups of 14 mice received a single dose of veltuzumab (0.5, 0.25, 0.1, or 0.05 µg) i.p with saline given to controls. In the WSU-FSCCL follicular cell lymphoma model, each mouse in groups of 15 was inoculated with 2.5×10$^6$ cells i.v. and 5 days later received a single dose of veltuzumab (0.035, 0.35, 3.5, or 35 µg) i.p. Animals were monitored daily and sacrificed humanely when hind-limb paralysis developed, when they became moribund, or if they lost more than 20% of initial body weight. Survival curves were analyzed using Kaplan-Meier plots (log-rank analysis), using the Prism (v4.03) software package (GraphPad Software, Inc.).

Intraperitoneal Versus Subcutaneous Therapy of Burkitt Lymphoma Xenografts.

Figure 8:
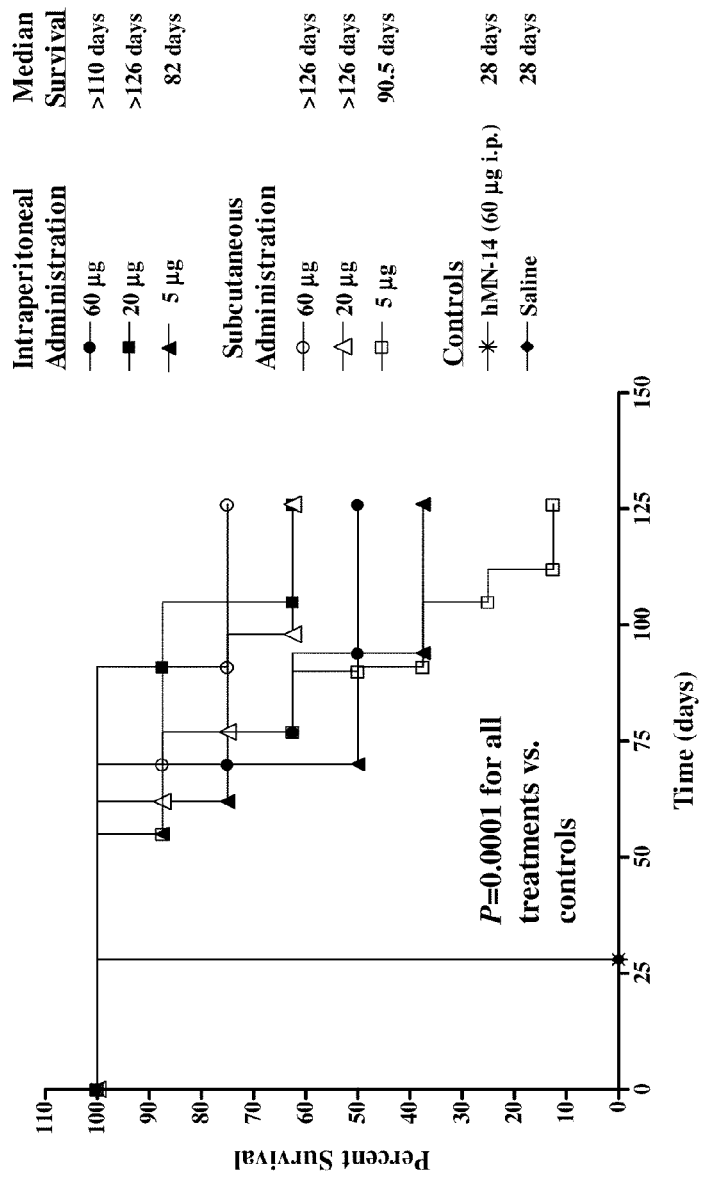
FIG. 8. Survival curves for veluzumab in a disseminated Burkitt's lymphoma xenograft model comparing intraperitoneal versus subcutaneous administration. C.B. 17 SCID mice were administered $1.5 \times 10^7$ Daudi cells i.v. on day 0. Therapy with veluzumab began on day 1 with mice receiving either a single i.p. or single s.c. injection of veluzumab. Doses administered were 60, 20, or 5 µg veluzumab. Control mice received an i.p. injection of either saline or 60 µg hMN-14 IgG (labetuzumab, anti-CEACAM5 isotype matched antibody).

Mice bearing disseminated disease were treated with single i.p. or s.c. injections of veltuzumab. All three doses of veltuzumab, regardless of whether administered i.p. or s.c., significantly increased survival of mice in comparison to the saline and labetuzumab control groups (FIG. 8, P=0.0001). Comparisons between equal doses administered i.p. and s.c. did not yield any significant differences (FIG. 8). While the control mice succumbed to disease (hind-limb paralysis) on day 28, the mean survival times (MSTs) of the two 60-µg groups were 101.9±26.8 and 114.6±21.8 days for i.p. and s.c., respectively, with 4/8 and 6/8 mice still alive when the study ended on Day-126. Similar results were obtained for the animals given 20 µg, with the MSTs of 116.4±14.0 (i.p.) and 108.4±26.2 (s.c.) days, and 5/8 mice alive at the end of the study in both groups. Only at the lowest dose (5 µg) was a >50% mortality rate observed (3/8 and 1/8 mice were still alive at the end of the study in each i.p./s.c. group), but these mice still had a >3.2-fold increase in the MSTs (91.1±30.9 and 91.6±22.5 days for i.p. and s.c., respectively) compared to controls.

Minimum Effective Dose of Veltuzumab in Daudi Burkitt Lymphoma Xenografts.

Figure 9:
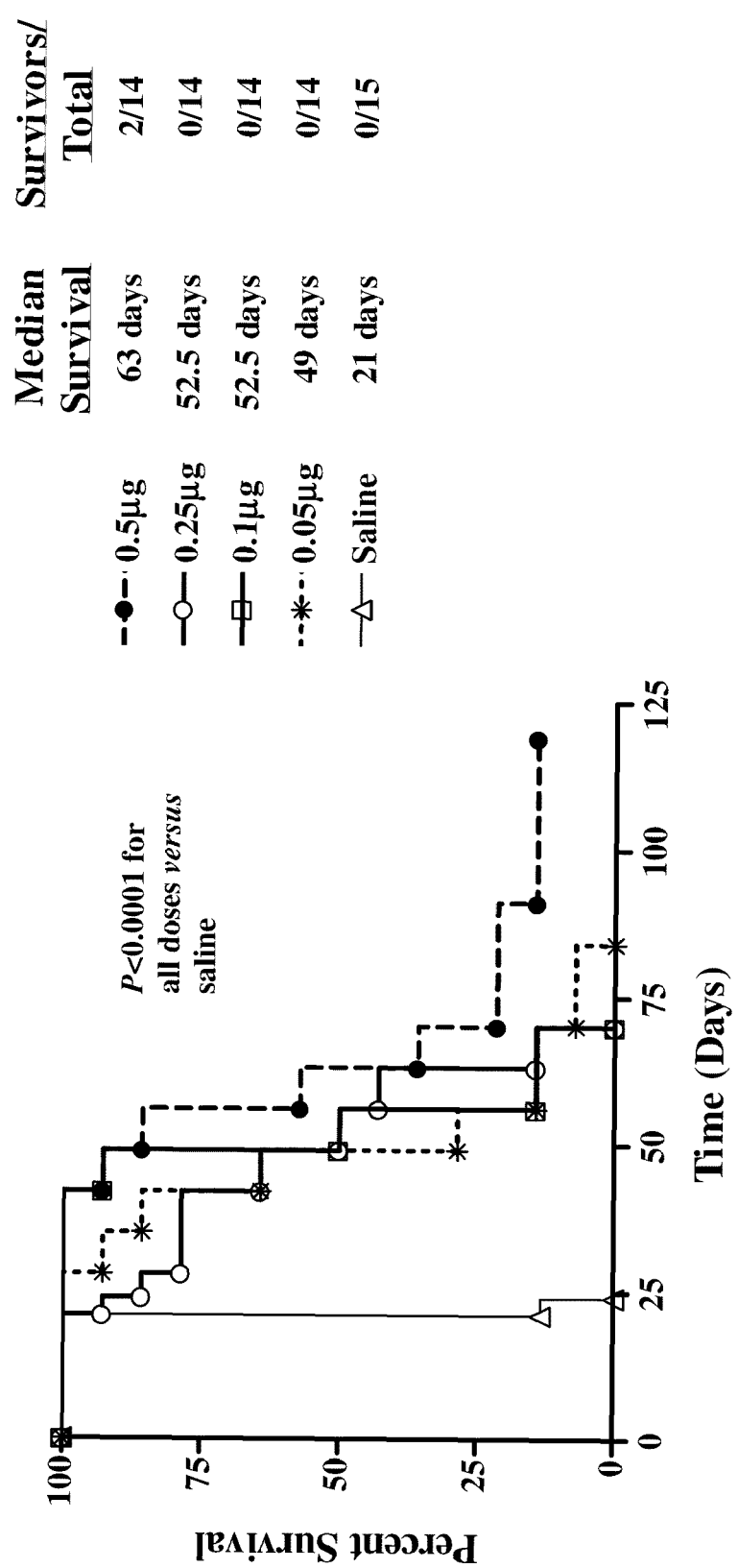
FIG. 9. The minimal effective dose of veluzumab was determined in a disseminated Burkitt lymphoma xenograft model. C.B. 17 SCID mice were administered $1.5 \times 10^7$ Daudi cells i.v. on day 0. Therapy with veluzumab began on day 1 with mice receiving a single i.p. injection of veluzumab. Doses administered were 0.5, 0.25, 0.1, or 0.05 µg veluzumab. Control mice received a 200 µL i.p. of saline.

Since a single 5 µg dose of veltuzumab proved to be potent in the Daudi disseminated Burkitt lymphoma model, even lower doses (0.5, 0.25, 0.1, and 0.05 µg) were then examined in this same disease model. Remarkably, all four doses improved survival significantly (P<0.0001) when compared to saline control mice (FIG. 9). For example, mice receiving a single dose of 0.5 µg had a 3-fold improvement in the MST compared to controls (69.5±23.9 vs. 21.4±1.1 days). Even the lowest tested dose of 0.05 µg (50 ng) increased the MST (50±8 days) by more than 2-fold over the controls.

Minimum Effective Dose of Veltuzumab in Follicular Cell Lymphoma Xenografts.

Figure 10:
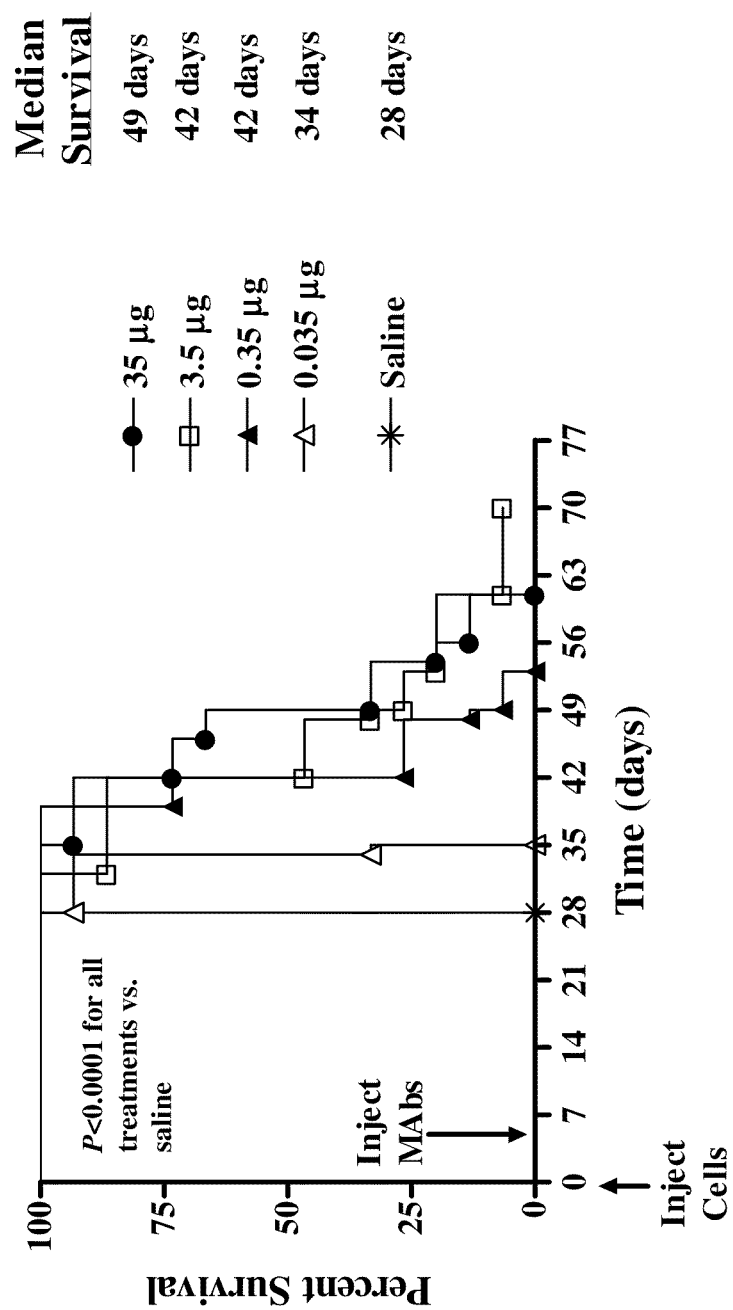
FIG. 10. Representative survival curves of mice bearing disseminated follicular cell lymphoma and treated with decreasing doses of veluzumab. C.B. 17 SCID mice were administered $2.5 \times 10^6$ WSU-FSCCL cells i.v. on day 0. On day 5 mice received a single i.p. injection of veluzumab at a dose of 35, 3.5, 0.35, or 0.035 µg. Control mice received only saline.

In a disseminated follicular cell lymphoma model, WSU-FSCCL xenografts, groups of mice were administered single i.p. injections of veltuzumab (FIG. 10). Each group received a 10-fold dilution ranging from a high of 35 µg to a low of 0.035 µg (35, 3.5, 0.35, and 0.035 µg). Therapy did not start until 5 days after the administration of the WSU-FSCCL cells. All four doses significantly increased survival of the mice when compared to the saline control (FIG. 10, control MST=28 days; P<0.0001). The MST of mice administered the 35-µg dose (44.3±4.9 days) was not significantly different from that of the 3.5-µg group (39.5±4.6 days), but was significantly (P<0.021) longer than that of the 0.35- and 0.035-µg (35 ng) groups (40.5±1.6 days and 33.3±2.1 days, respectively). However, all mice, except for one in the 3.5-µg group, succumbed to disease progression by Day-61.

Example 14

Veltuzumab Shows Improved In Vivo Efficacy Compared to Rituximab in a Mouse Model System SCID mice were inoculated with human Burkitt lymphoma (Raji) cells by tail vein injection. At 5, 10, 15 and 20 days after inoculation, the mice received either rituximab or veltuzumab (hA20) at 10 mg/kg/dose. The results of cumulative survival are shown in FIG. 13.

Figure 13:
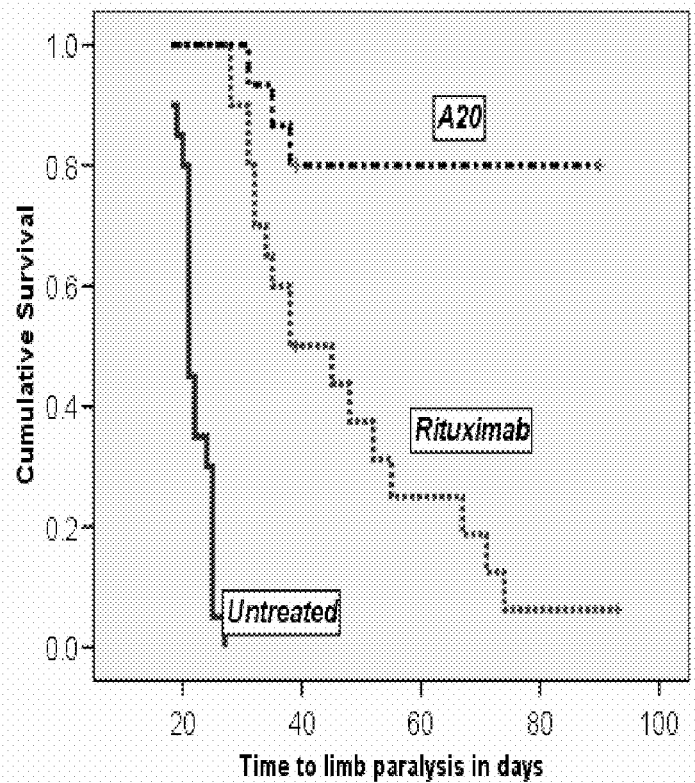
FIG. 13. Veluzumab is more effective than rituximab in controlling the growth of lymphoma in vivo in SCID mice. SCID mice were inoculated with Raji cells by tail vein injection. On days +5, +10, +15 and +20, the mice received either rituximab or veluzumab (hA20) at 10 mg/kg/dose. Treatment with veluzumab resulted in a significantly longer cumulative survival time compared to treatment with an identical dosage of rituximab (P 0.005).

As seen in FIG. 13, SCID mice injected with Raji lymphoma cells and treated with veltuzumab (hA20) showed a significant improvement (P=0.005) in cumulative survival compared to mice treated with an identical dose of rituximab. In this study, time to limb paralysis was used as a surrogate end-point for survival. FIG. 13 shows that at over 90 days after inoculation, SCID mice with Raji lymphoma that had been treated with veltuzumab exhibited about an 80% survival rate, while equivalent mice treated with rituximab exhibited a survival rate close to zero. The lower part of FIG. 13 shows that the estimated median cumulative survival was 22.1 days for control mice, 47.9 days for mice treated with rituximab and not yet reached for mice treated with veltuzumab.

These results demonstrate that the replacement of Kabat 101 asparagine with aspartate in the CDRH3 sequence produces a significant improvement in in vivo efficacy in a mouse model system using human Burkitt lymphoma cells.

Example 15

Treatment with Low-Dose Veltuzumab

Idiopathic Thrombocytopenic Purpura

A 39-year-old female with a 6-month history of ITP had received steroids as standard of care without satisfactory improvement of platelet levels. She received 2 doses of 80 mg/m$^2$ veltuzumab administered intravenously 2 weeks apart. In spite of the low dose, her B-cell levels were depleted following the first dose, and her serum antibody levels increased to 10 μg/mL after the first dose, reaching 19 μg/mL after the second dose, and then clearing slowly but still measurable (1 μg/mL) 8 weeks later. Most importantly, her platelet levels rapidly increased from 24,000/mm$^3$ at study entry to normal limits (>150,000/mm$^3$) within 4 days after the first dose. This complete response is currently continuing and her platelets are still >150,000/mm$^3$ at the last evaluation 18 weeks after treatment. Interestingly, the patient also suffered from ulcerative colitis, and went off therapy for this condition during the trial with veltuzumab. During veltuzumab therapy, all signs and symptoms of ulcerative colitis abated over the current 18-week followup, which appears to be a collateral effect of this B-cell therapy.

Marginal Zone Lymphoma

A 79-year-old female with marginal zone lymphoma was initially diagnosed 12 years earlier and previously treated with CHOP and then CVP, but no rituximab. She presented with stage-IV disease including 2 enlarged iliac lymph nodes and bone marrow involvement. She received 4 once-weekly doses of 138 mg (80 mg/m$^2$) veltuzumab administered intravenously. B-cell levels were depleted following the first dose, and serum antibody levels increased with successive doses, reaching 120 μg/ml after the last dose and then clearing slowly with values still measurable (5 μg/ml) at last evaluation, 12 weeks later. Most importantly, the patient had an excellent response to treatment, with regression of the iliac lymph nodes to normal size on a CT scan and a negative bone marrow biopsy. The complete response is currently continuing at the last evaluation, 15 months after treatment.

Follicular Lymphoma

A 42-year-old female with a 15-year history of follicular lymphoma had received multiple prior treatment regimens, including intravenous veltuzumab to which she had achieved a 9-month response. She received 80 mg veltuzumab injected subcutaneously every two weeks for a total of 4 doses. In spite of the low dose administered by this route, B-cell levels were depleted following the first dose. Serum antibody levels measured over several days following the initial dose showed levels increasing slowly to 10 μg/ml, which is comparable to levels obtained with intravenous administration. At the 4-week followup after the last treatment, examination of the patient revealed evidence of most enlarged lymph nodes with disease regressing, and at 4 weeks later, the repeat examination, including computed tomography scans, showed that the sum of all dimensions of involved lymph nodes were reduced by more than 50% compared to the cumulative dimensions of these nodes at baseline, indicating that the patient had at this point a partial response. Further evaluations are pending for this recent patient, but the demonstration of good bioavailability and the evidence of activity with B-cell depletion as well as >50% reduction of disease proves that the s.c. route was effective.

Follicular Lymphoma

A 41-year-old male with stage-IV, grade-3, follicular lymphoma was initially diagnosed 8 years earlier and had previously been treated with CHOP chemotherapy but no rituximab. He received 4 once-weekly doses of 80 mg/m$^2$ veltuzumab administered intravenously. B-cell levels were depleted following the first dose, and serum antibody levels increased with successive doses, reaching 86 μg/mL after the last dose and then clearing slowly with values still measurable (4 μg/mg) at last evaluation, 12 weeks later. Most importantly, there was complete disappearance of all disease including a 3.6 cm scalp lesion that had been present at study entry. The complete response continued until 9 months after treatment, at which time a new lesion was seen by FDG-PET imaging. This patient also shows that the low dose of veltuzumab was potent, inducing a complete response in this patient, including ablation of circulating B-cells after only a single administration of 80 mg/m$^2$ of veltuzumab.

Example 16

Therapy of Follicular Large Cell Lymphoma

AF is a 63-year-old white male with Grade-3 follicular large-cell non-Hodgkiin's lymphoma, proven to be CD20+ by lymph node biopsy in January of 2004. His stage at diagnosis was stage 3, but presents now in stage 2. His prior therapy in 1992 included doxorubicin, vincristine, high-dose cyclophosphamide, which resulted in a remission of 24 months. In 1996, he received a regimen of ICE (ifosfamide, carboplatin and etoposide), and also stem-cell therapy, followed by consolidation radiation to a retroperitoneal mass. He responded for 88 months. He recently presented with no B-symptoms, no significant CBC, serum chemistry or serum immunoglobulin abnormalities, 687 CD3-T cells/μL, 32 CD19-B-cells/μL and enlarged supraclavicular node of 10×8 cm, left and right axillary masses of 2.0 and 2.8 cm diameters, and a lateral neck mass of 2-3 cm. The patient was given four s.c. injections of 80 mg veltuzumab, two weeks apart. There were no significant adverse reactions or safety issues, only minor transient erythematous reactions and tenderness at the injection sites. At four days after the first injection, CD19+

B-cells in the blood were measured as 0, so were completely ablated. The patient's large neck mass shrank, as measured by palpation, by 50% 4 days after the first injection, and he indicated that he was feeling better. CT scans are pending in another 4 weeks. The patient apparently had a rapid depletion of circulating B-cells and a significant regression of his neck mass after a single s.c. injection of 80 mg veltuzumab.

This surprising result shows that a single 80 mg s.c. injection of the CDRH3 (Kabat 101) substituted anti-CD20 humanized antibody veltuzumab is capable of ablating peripheral B-cells and significantly shrinking an apparent B-cell tumor mass. This is the first report of such a low dose s.c. injection of veltuzumab producing such a profound effect on circulating and sessile B-cells, as well as a NHL masses.

Example 17

Evans Syndrome

MT is a 3-year old Asian female followed since age 11 months for multiple hematological autoantibodies and pancytopenia. At age 11 months she presented with diarrhea, red spots on her legs, blood in stools, diffuse petechiae and purpura on head, neck, trunk, and extremities, cervical adeonopathy, including several 1-cm axillary nodes, slightly enlarged spleen, increased fatigue, decreased appetite, bruising, and blasts on peripheral blood smear, increased sed rate (116 mm/h), D-dimer elevated, and bone marrow aspirate showing a hypercellular marrow (>90% cellularity), erythroid, myeloid and megakaryocyte precursors being abundant (maturation arrest myelocyte/metamyelocyte level but mature neutrophils seen). Red cell precursors also showed some maturation arrest, but no cytogenetic abnormalities. Lab studies also indicated elevations in immunoglobulins IgA, IgG, and IgM, and an increase in circulating CD19+ B-cells (48%). There was also evidence of a strong positive neutrophil antibody and a strong positive platelet antibody, with IIb/IIIa specificity. The patient was first given steroids, but had a poor or no initial response. Therefore, she was given two courses of rituximab. In the first course, she received 4 weekly doses and the platelet count stabilized, but she continued to be anemic and neutropenic. Her CD20 and CD19 lymphocytes decreased, but after only 5-6 weeks, these increased dramatically. A second course of rituximab involved 3 weekly doses, and over several weeks, her platelet count, hemoblobin and absolute neutrophil normalized, and after 2-3 months, red cell and platelet antibodies resolved. This remission to rituximab lasted for 9 months, but then thrombocytopenia was noted on a routine CBC, and again red cell, neutrophil and platelet antibody was detected. The patient was then given prednisone and intravenous immunoglobulin, and showed a partial response.

Then a third course of rituximab, 2 weekly doses, was given, and two episodes of anaphylaxis resulted, requiring aggressive medical management. The patient showed a transient response, 2-3 months, but pancytopenia and hematological antibodies recurred. The patient has since had transfusions for her anemia, with red cell antibodies and anemia being her most significant problem, with intermittent episodes of thrombocytopenia; she was not responsive to steroids or intravenous immunoglobulin.

Since the next option is splenectomy or a course of cytotoxic chemotherapy, she is given an experimental regimen of veltuzumab, consisting of 10 mg subcutaneously, repeated at a dose of 10 mg veltuzumab given subcutaneously 2 weeks later. Prior to the second dose, depletion of circulating CD19-positive B-cells is found, and improvement in her red blood cell and platelet counts is observed. Two weeks after the second s.c. injection of veltuzumab, the patient's general condition shows improvement, her red blood cell, neutrophil, and platelet antibodies are barely measureable, and all hematological abnormalities show significant improvement, with platelet, neutrophil, and RBC counts being at the lower end of the normal ranges. At 2 months post therapy, the patient continues to be in remission. No evidence of any anaphylaxis is noted at anytime during the veltuzumab therapy, indicating that there is no immune crossreactivity ro rituximab, and that very low subcutaneous doses of veltuzumab are therapeutic in this patient with Evans syndrome.

Example 18

Chronic Lymphocytic Leukemia

RT is a 47-year-old female with a 3-year history of chronic lymphocytic leukemia, now relapsed after a course of alemtuzumab (CAMPATH®), but prior history shows that she had responses of various durations to chlorambucil and other cytotoxic drugs. She presents now with evidence of CLL in her bone marrow and also an elevated peripheral lymphocyte count with prominent blasts of 58,000/cmm. She is given subcutaneous injections of 40 mg veltuzumab twice weekly for 6 weeks, and after the second injection, the peripheral lymphocyte count drops by 55%. Two weeks after the fourth s.c. injection, her peripheral blood counts are slightly above the normal range, but more importantly, bone marrow aspiration shows a definite good partial response, and the clinical picture of fatigue, petechiae, and diffuse enlarged cervical and other lymph nodes improve dramatically.

Example 19

Immune Thrombocytopenic Purpura (ITP)

RH is a 66-year-old male with a history of ITP for 1.5 years, 4 prior therapies, no splenectomy, and presenting with 26,000 platelets/cmm at baseline. He is given 2 doses of 40 mg veltuzumab subcutaneously, 2 weeks apart. Prior to the second injection, measurement of his blood CD19+ lymphocytes shows >90% reduction. Two weeks after the second injection of veltuzumab, his platelet count shows a doubling, which increases to 70,000 by the $5^{th}$ week post therapy, which is maintained until week 11, when the platelet count again falls to counts of <5,000/cmm. The patient is then retreated twice with 30 mg veltuzumab s.c., again 2 weeks apart. Four days after the second injection the platelet count rises to 28,000/cmm, and then to 42,000/cmm by week 3 post therapy. At 6 weeks post therapy, the platelet count is significantly improved to 67,000/cmm, and the patient is considered to have a good partial response, with no evidence of bleeding or petechiae during veltuzumab therapy, and returns to full-time activity and work.

Example 20

Rheumatoid Arthritis

FH is a 37-year-old female who gradually develops painful joints, particularly her wrists, over 3 months, with pain and early morning stiffness of about 40 min. On examination, both her wrists and the metacarpophalangeal joints of both her hands are swollen and tender, but are not deformed; there are no nodules or vasulitic lesions. She has an elevated C-reactive protein (CRP) level of 30 mg/l but otherwise normal laboratory findings, but with a positive rheumatoid factor and antinuclear antibodies. She clearly is at the beginning of RA and is first treated with ibuprofen. However, despite some initial symptomatic improvement, the pain, stiffness and swelling of the hands persist, and 2 months later, her knees are similarly affected. Six months after the initial presentation, she develops 3 subcutaneous nodules on the left elbow, small, painless and immobile, but not tender. X-rays of the hands show bony erosions in the metacarpal heads, again an elevated CRP (53 mg/l). She is now given 120 mg veltuzumab subcutaneously for 3 weekly injections. Her first evidence of improvement occurs after the second injection, when she notices that her morning joint pain and stiffness is reduced to about 15 minutes, and within 2 weeks after the third injection, she experiences improved mobility, her joints appear to have reduced swelling, and her CRP levels falls to 15 mg/l, slightly above the normal range. Her symptoms and signs of RA are markedly improved for the next 8 weeks of followup. No methotrexate or steroid therapy is required during the veltuzumab treatment or for the 2 months thereafter.

Example 21

Sjögren's Syndrome with Arthritis

K.S. is a 41-year-old woman who is referred to an oral surgeon for evaluation of a dry mouth. Except for an elevated sedimentation rate (ESR, 60 mm/h), she has no remarkable laboratory abnormalities. She develops a mild conjunctivitis and sore eyes 2 months later. Her rheumatoid factor becomes positive, her total serum proteins are raised (100 g/l), as also is her IgG level (30 g/l). The Schirmer test is markedly abnormal (only 3 mm of the filter strip in the right eye and 1 mm of that in the left eye became wet). She is treated with methylcellulose eye drops to prevent corneal ulceration, and over the next year shows a steady elevation of rheumatoid factor titer and anti-nuclear antibodies, and also develops evidence of polyarthritic changes in her hands and wrists. She is considered to have a mild Sjögren's syndrome and receives non-steroidal anti-inflammatory drugs (NSAIDs) for the arthritis, but these have no effect on the sicca complex. She is then given a course of veltuzumab, starting with an intravenous infusion of 15 mg, followed after a week by three more subcutaneous injections of 40 mg veltuzumab weekly. Two weeks after the completion of this therapy course, her polyarthritic symptoms and signs show considerable improvement, but the most dramatic effect is the improvement of her salivation, confirmed by an improved Schirmer test. The patient now has only minimal dry mouth and no conjunctivitis or sore eyes, and this remission is maintained for 4 months.

Example 22

Desensitization During Renal Transplantation

SW is a 56-year-old, 55 kg, woman with 5 previous living births and with end-stage renal disease and is waiting for a transplant to replace her left kidney. She is highly HLA sensitized, showing high titers of anti-HLA antibodies. She is undergoing regular hemodialysis. In order to undergo renal transplantation, she requires desensitization to the anti-HLA antibodies, and therefore is administered one intravenous dose of 120 g of human polyclonal immune globulin (10% formulation), followed 4 days later by an s.c. injection of 40 mg veltuzumab. The veltuzumab s.c. injection is repeated on day 8, day 12, and again on day 21. After the first injection, the blood CD19+ B-cells totally disappear, and 8 weeks after the 4$^{th}$ s.c. injection of veltuzumab, they remain depleted.

Prior to receiving the intravenous immune globulin, she is given 40 mg intravenous methylprednisolone, 650 mg oral acetaminophen, and 50 mg diphenhydramine. No premedication is given prior to the subsequent veltuzumab injections. Following this course of pre-transplant therapy, the panel-reactive antibody level is reduced significantly, and T-cell flow-cytometric cross-matching shows a 50% drop prior to transplantation. Three months later, the patient receives a kidney transplant from a deceased donor, and a typical induction therapy immediately thereafter (30 mg alemtuzumab s.c.) and then immunosuppressive therapy consisting of prednisone, mycophenolate mofetil, and tacrolimus, tapered over the next year, as well as prophylactic antibiotics, are given. She has no rejection episode as monitored for the year post transplantation, and her renal functions normalize. This appears to be a successful case of desensitizing a patient in need of a renal transplant quite effectively, resulting in a successful transplant.

Example 23

Structure-Function Relationships and Therapeutic Characteristics in Anti-CD20 Antibodies Approaches to improve on rituximab, the first chimeric anti-CD20 MAb introduced into lymphoma and autoimmune disease therapy, include reducing the murine component by CDR-grafting (humanization) and making fully human MAbs from transgenic mice, targeting a different CD20 epitope, and enhancing CDC or ADCC activity by altering Fc structures (Forero et al., *Proc 99$^{th}$ Ann Meeting of the Am Assoc Cancer Res,* 2008, abstract LB-70; Glennie et al., *Mol. Immunol.* 2007, 44:3823-37). However, it is not yet known which of these modifications will result in a more potent anti-CD20 MAb, as measured either by B-cell depletion, control of autoimmunity, or lymphoma responses in patients, especially when they are refractive or resistant to rituximab.

At present, rituximab induces objective responses, mostly partial responses, in about half of patients with follicular lymphoma (Castillo et al., *Exp Hematol.* 2008, 36:755-768), yet both the optimal therapeutic dose and schedule still remain undefined. Despite the use of rituximab in virtually all NHL patients for the past decade, its mechanisms of action, as well as those of other anti-CD20 MAbs, either in model systems or patients, remain debated among numerous studies demonstrating cell killing mediated by CDC, ADCC, and direct signaling with apoptotic effects. (Glennie et al., *Mol. Immunol.* 2007, 44:3823-37; Maloney, *Hematology Am Soc Hematol Educ Program.* 2007:226-232; Martin et al., *Semin Hematol.* 2008; 45: 126-132.)

Because of our observations that rituximab combined with epratuzumab showed evidence of improved responses in NHL patients, with no increased side-effects over those resulting from monotherapy with rituximab (Goldenberg, *Expert Rev Anticancer Ther.* 2006, 6:1341-1353; Leonard et al., *J Clin Oncol.* 2005, 23:5044-5051; Strauss et al., *J Clin Oncol.* 2006, 24:3880-3886) our original purpose was to construct a humanized anti-CD20 MAb that could be combined with epratuzumab, but would be more tolerable for rapid infusions due to having the FRs of epratuzumab. The first characterization study of veltuzumab reported similarities to rituximab in terms of epitope binding, affinity, ADCC, CDC, and cell growth inhibition in vitro (Stein et al., *Clin Cancer Res.* 2004, 10:2868-78). After treating patients with indolent NHL, the anticipated improved tolerability and infusion profile was confirmed, but also a high rate of complete responses (CR/CRu) was found. The Phase I/II trial in 82 indolent NHL patients demonstrated complete response rates for all doses tested (27% for all follicular lymphoma patients for doses between 80 and 750 mg/m$^2$ once-weekly×4 weeks) (Morschhauser et al., *Proc Am Soc Clin Oncol, J Clin Oncol.* 2007, 25(18S):449s, Abstract 8032; Goldenberg et al., *Proc Amer Soc Clin Oncol, J. Clin. Oncol.* 2008, 26(15S): 142s, Abstract. 3043; Morschhauser et al., *J Clin Oncol,* 2009 Jul. 10; 27(20):3346-53. Epub 2009 May 18) exceed those reported for repeated use of rituximab at its conventional dose in comparable patients (Davis et al., *J Clin Oncol.* 2000, 18:3135-3143). These findings prompted us to re-evaluate the functional properties of veltuzumab in comparison to rituximab.

Studies in cynomolgus monkeys (Example 12) have confirmed the effects of various i.v. and s.c. doses, and we found that a single dose as low as the equivalent of 80 mg/m$^2$ in humans, given by either route, is sufficiently potent to induce peripheral blood and lymphatic organ B-cell depletion. In addition, enhanced survival and even cures were demonstrated in mice bearing CD20+ lymphoma xenografts after a single, i.p. or s.c. dose as low as 0.05 µg. In these mouse studies, a dose-response was observed, but no significant difference between the i.v. or s.c. routes was noted.

Although different anti-CD20 MAbs have shown some variations in functional properties and epitope specificities, mediating different CDC and cell-killing effects (Nishida et al., *Int J Oncol.* 2007, 31:29-40), virtually all recognize the large, extracellular loop and partially or completely cross-block each other (Polyak et al., *J Immunol.* 1998, 161:3242-3248; Polyak and Deans, 2002, 99:3256-3262; Perosa et al., *Blood* 2006, 107:1070-1077) except ofatumumab, which is reported to bind to a novel epitope of CD20 (Teeling et al., *J Immunol.* 2006, 177:362-371). Veltuzumab crossblocks binding by rituximab (Stein et al., *Clin Cancer Res.* 2004, 10:2868-78), suggesting either the same epitope is recognized by both MAbs or binding to an adjacent epitope could result in steric hindrance.

In the Examples above, the binding and dissociation parameters of veltuzumab and rituximab were compared both by Scatchard analyses (Example 3) and off-rate measurements (Example 5). The Scatchard analyses confirmed that veltuzumab and rituximab have similar affinity for cell-surface CD20 and number of binding sites per cell (Example 3). Surprisingly, statistically significant differences between veltuzumab or cA20 vs. rituximab or D101N were found in a slower off-rate (i.e., longer cell-surface retention) in all 3 human lymphoma cell lines tested (Example 5), and a higher CDC-mediated cell killing in Daudi lymphoma cells by veltuzumab (Example 8), compared to rituximab or D101N. Whether measured in the presence or absence of a competitive binder, veltuzumab and cA20, both containing $Asp_{101}$ instead of $Asn_{101}$ in CDR3-$V_H$, yielded significantly (P<0.0001) slower off rates (~2.5-fold) than rituximab or D101N (Example 5).

The demonstration of CDC activity for veltuzumab in Daudi being significantly more than rituximab or D101N is also intriguing, since the Fc portion of veltuzumab is derived from that of epratuzumab, which fails to show CDC functions (Carnahan et al., Mol. Immunol. 2007, 44:1331-41). This suggests that rapid internalization of epratuzumab may prevent it from residing on the cell surface long enough to form the membrane attack complexes. The results above also suggest that the off-rate difference between veltuzumab and rituximab is not related to the enhanced CDC observed in Daudi cells, as first postulated for ofatumumab (Teeling et al., *Blood* 2004, 104:1793-1800), since this difference was not observed for CDC in two other cell lines that also showed a significantly slower off-rate with veltuzumab compared to rituximab (Examples 5 and 8). Since these results with veltuzumab involve evidently a different targeted epitope of CD20 than ofatumumab, it does not appear that such off-rate changes are due to the position of the epitope, as postulated by Teeling et al. (2004). Nevertheless, it appears that such off-rate changes, as suggested by Teeling et al. (2004) for ofatumumab and reported herein for veltuzumab, may explain why a given anti-CD20 antibody functions at lower concentrations than other MAbs (e.g., rituximab), such as we have found with veltuzumab (Examples 12 and 13). Whether CDC plays a role remains unknown.

It is unlikely that these differences are related to veltuzumab having the FRs of epratuzumab. The $V_H$ and $V_K$ chains of cA20 differ from those of rituximab in six positions, but except for the 101-residue in CDRH3, the remaining five residues (two in FR4-$V_H$ and three in FR1-$V_K$) are unlikely to be responsible for the differential off-rates. Du et al. (*Mol. Immunol.* 2008, 45:2861-2868) reported a weaker interaction of the CDRs of another anti-CD20 MAb, c2H7, compared to rituximab, suggesting that the amino acid residues of 2H7 at the equivalent positions in CDRH3 have more bulky side chains, resulting in a wider pocket to accommodate CD20 peptide. The fact that cA20 and veltuzumab have virtually the same affinity and off-rate, whereas cA20 has more similar FRs to rituximab than to veltuzumab, emphasizes the more critical role of CDRs than the FRs in interacting with CD20. Thus, the significant difference observed in the off-rate between veltuzumab/cA20 and rituximab/D101N is apparently due to the single amino acid difference in CDRH3, and not to the more extensive differences in the FRs between veltuzumab and rituximab. Accordingly, we believe this is the first single amino-acid change in a CDR that is shown to cause a functional effect, resulting in a more potent antibody.

The in-vitro off-rate and CDC differences described herein are comparable to the findings with another anti-CD20 MAb, ofatumumab, which was reported to bind to a different epitope than rituximab (Teeling et al., *J Immunol.* 2006, 177: 362-371) and claimed to be therapeutically more active than rituximab in vitro (Teeling et al., *Blood* 2004, 104:1793-1800). However, this is not consistent with the relatively high doses of ofatumumab chosen for clinical studies, also requiring long infusion times like rituximab (Coiffier et al., *Blood* 2008, 111:1094-1100; Hagenbeek et al., *Blood* 2008, 111: 548609), or the lowest dose of 0.5 mg/kg (10 µg/mouse) shown to elicit growth inhibition in lymphoma xenografts (Bleeker et al., *Brit. J. Haematol.* 2007, 140:303-312).

Still another recently developed human anti-CD20 MAb, G101, which has properties of a Type-II anti-CD20 MAb (Umana et al., *Ann Oncol.* 2008, 19 (Suppl 7), abstract 98), has been shown to be more potent in vitro and in animal models than rituximab, when mice were given repeated doses of 10-30 mg/kg (Id.) This translates to each dose of repeated applications being between 200 and 600 µg in a 20-g mouse, which are at least 4,000- to 12,000-fold higher than the single doses of 0.05 to 0.35 µg of veltuzumab showing high anti-growth activity in the lymphoma xenografts tested (Examples 11 and 13). Depletion of murine NK cells and neutrophils prevented these effects of veltuzumab (Example 10), emphasizing the role of ADCC in vivo, as shown previously for rituximab (Hernandez-Ilizaliturri et al., *Clin Cancer Res.* 2003; 9:5866-73).

These in-vitro, mouse, monkey, and other human studies indicate (i) that veltuzumab is active at a fraction of the conventional clinical dose of rituximab or of the minimal therapeutic doses of two other second-generation anti-CD20 MAbs in preclinical models, (ii) that the two distinguishing differences in activity vs. rituximab involve CDC and off-rate functions, and (iii) that the lower off-rate appears to be related to a single amino acid mutation at the Kabat-101 residue in the CDRH3.

Example 24

Low-Dose Veltuzumab in Recurrent Non-Hodgkin's Lymphoma (NHL)

Summary

A total of 82 patients (34 male, 48 female; age 33-85) received 4 once-weekly doses of 80-750 mg/m² veltuzumab, with study evaluations continued for 12 weeks and then until disease progression. They had follicular (FL, N=55) or other (N=27) B-cell NHL, were predominantly stage III/IV (79%) at study entry, and had received 1-7 prior treatment regimens (median, 1.5), most (89%) including at least one rituximab-containing regimen.

Veltuzumab was generally well-tolerated, with drug-related adverse events being transient (Grade 1-2), and with shorter infusion times (typically 2 h initially and 1 h subsequently) at lower doses. In follicular lymphoma, 24/55 patients had objective responses (OR, 44%), with 15 (27%) complete responses (CR/CRu) occurring even after 2-5 prior rituximab-regimens, with less favorable prognosis (elevated LDH, tumors>5 cm, FLIPI≧2), and at all dose levels. In other B-cell NHL, 5/6 patients with marginal zone lymphoma had ORs (83%), including 2 CR/CRu's (33%), one at 80 mg/m², while 3/7 patients with diffuse large B-cell lymphoma had partial responses (43%), including one at 80 mg/m². Even at 80 mg/m¹, B-cells were depleted after 1st infusion, and mean antibody serum levels exceeded values (25 µg/mL) considered important for anti-CD20 therapy (with apparent higher levels in responders at this dose), with post-treatment serum clearance similar to or slower than rituximab.

Background

The chimeric anti-CD20 monoclonal antibody (MAb), rituximab (Rituxan®; Genentech, South San Francisco, Calif.; Biogen Idec Pharmaceuticals, San Diego, Calif.), was approved more than a decade ago for the treatment of relapsed or refractory low-grade or follicular CD20 positive, B-cell lymphoma. In the pivotal trial in this population, a 375-mg/m² dose administered once weekly for 4 consecutive weeks resulted in a 48% overall response rate (6% complete responses). (McLaughlin et al., *J Clin Oncol* 16:2825-2833, 1998.) Expanding on this initial success, rituximab has been broadly adopted for use in B-cell malignancies (Traullé & Coiffier, *Future Oncol* 1:297-306, 2005; Marcus & Hagenbeek, *Eur J Haematol Suppl* 67:5-14, 2007; Cheung et al., *Cancer Treat Rev* 33:161-176, 2007), primarily in combination with chemotherapy (e.g., Czuczman et al., *J Clin Oncol* 22:4711-4716, 2004; Coiffier et al., *N Engl J Med* 346:235-242, 2002), as well as in autoimmune disorders (Chambers & Isenberg, *Lupus* 14:210-214, 2005; Silverman, *Front Biosci* 12:2194-2206, 2007; Cohen et al., *Arthritis Rheum* 54:2793-2806, 2006; Hauser et al., *N Engl J Med* 358:676-688, 2008). Second-generation anti-CD20 antibodies have been constructed in order to increase efficacy, decrease toxicity (primarily infusion reactions) or immunogenicity, and allow more rapid administrations (Dörner & Burmester, *Curr Opin Rheumatol* 20:263-268, 2008; Martin et al., *Semin Hematol* 45:126-132, 2008; Genovese et al., *Arthritis & Rheumatism* 54:S66, 2006; Morschhauser et al., *Blood* 110:199a, 2007; Hagenbeek et al., *Blood* 111:5486-5495, 2008; Coiffier et al., *Blood* 111:1094-1100, 2008).

Veltuzumab (hA20) is a CDR (complementarity-determining region)-grafted, humanized, anti-CD20 IgG-kappa MAb that was constructed with light chain CDRs and heavy chain CDR1 and CDR2 identical to rituximab, but a different CDR3-variable-region-heavy-chain construct, and with the remaining framework regions taken from epratuzumab, a humanized anti-CD22 MAb (Goldenberg et al., *Proc Am Soc Clin Oncol* 22:595, 2003; Goldenberg et al., *Proc Am Soc Clin Oncol* 26:142s, 2008; Example 1). These changes resulted in important differences compared to rituximab, such as significantly slower off-rates in all 3 human lymphoma cell lines tested (Example 5) and a significantly increased complement-dependent cytotoxicity in one of these cell lines (Example 8), while no significant differences in direct proliferation inhibition, apoptosis, or antibody-mediated cytotoxicity were observed in vitro (Examples 6 and 9; Goldenberg et al., *Proc Am Soc Clin Oncol* 22:595, 2003; Stein et al., *Clin Cancer Res* 10:2868-2878, 2004; Goldenberg et al., *Proc Am Soc Clin Oncol* 26:142s, 2008). In addition, studies in normal cynomolgus monkeys (Example 12) and in mice bearing human lymphoma xenografts (Example 13) found that very low doses of veltuzumab not only given intravenously, but also subcutaneously, were very effective in depleting B-cells and controlling tumor growth, respectively, even curing a significant number of mice (Examples 13 and 14; Goldenberg et al., *Proc Am Soc Clin Oncol* 26:142s, 2008).

The first clinical test of veltuzumab was in a young patient with systemic lupus erythematosus (SLE) with life threatening cytopenias who had become refractory to standard salvage medications and no longer responded to rituximab (Tahir et al., *Rheumatology* 44:561-562, 2005). Veltuzumab was able to deplete peripheral B-cell levels even in the face of extremely high serum levels of anti-rituximab antibodies (HACA 43,000 ng/mL; normal <5 ng/mL), and the patient responded rapidly.

Since most experience with rituximab is in non-Hodgkin's lymphoma (NHL), the present Example was performed to characterize the basic safety, tolerability, pharmacokinetics, pharmacodynamics, immunogenicity and preliminary efficacy of veltuzumab in this population, particularly follicular or low-grade lymphoma (Morschhauser et al., *Blood* 106: 683a, 2005; Morschhauser et al., *Blood* 108:769a, 2006; Morschhauser et al., *Proc Am Soc Clin Oncol* 25, 449, 2007). Complete trial results, including follow-up with the last patients entered now at least 6 months beyond treatment, and with several of the earliest patients continuing in remission now for more than 3 years, are provided below.

Methods

An open-label, single-arm, multicenter phase I/II study of veltuzumab administered by intravenous infusion to patients with refractory or recurrent NHL was conducted to evaluate the safety and effectiveness of veltuzumab in patients with refractory or recurrent NHL. The study end-points were safety, efficacy (objective and complete response rates, duration of response, time to progression), pharmacokinetics, pharmacodynamics, and immunogenicity.

All patients received once-weekly doses for 4 consecutive weeks. The initial portion of the study enrolled cohorts treated at increasing dose levels from 120 mg/m$^2$ up to 750 mg/m$^2$, i.e., up to twice the dose usually given with rituximab. In the second portion of the study, additional patients received veltuzumab at 375 mg/m$^2$ and below (Morschhauser et al., *Blood* 106:683a, 2005). It became apparent that objective responses (increasing complete responses) occurred at all dose levels without obvious dose response (Morschhauser et al., *Blood* 108:769a, 2006), consistent with observations in animal studies that low doses of this antibody may be effective (Example 13). Since even lower doses of veltuzumab (including 60 mg/m$^2$) had shown promise in several other patients with moderate SLE activity (Example 15), the protocol was amended and the final patients enrolled in the study were treated at the lower dose level of 80 mg/m$^2$ (Morschhauser et al., *Proc Am Soc Clin Oncol* 25, 449, 2007).

Patient population—To be eligible, adults with documented CD20+ B-cell NHL by WHO criteria must have failed at least one prior standard chemotherapy regimen or rituximab treatment for NHL and have measurable disease with at least one lesion $\geq 1.5$ cm by CT, but no mass $>10$ cm. Patients must be at least 12 months beyond any rituximab, without progression during or within 6 months of rituximab treatment, NCI CTC Grade 3 or 4 toxicity to rituximab, or known HACA positivity. Eligibility also required hemoglobin$\geq 10$ g/dL, ANC$\geq 1.5 \times 10^9$/L, platelets$\geq 100 \times 10^9$/L (all without transfusional support), creatinine and bilirubin$\leq 1.5 \times$institutional upper limit of normal (IULN), AST and ALT$\leq 2.5 \times$ IULN, 0-1 ECOG or KPS$\geq 70$ performance status, life expectancy $\geq 6$ months, 12 weeks beyond any autologous stem cell transplant, and 4 weeks any beyond chemotherapy, other experimental treatments, or any radiation therapy to the index lesion(s). Patients with primary CNS lymphoma, HIV lymphoma, transformed lymphoma, symptomatic CNS metastases or carcinomatous meningitis, pleural effusion with positive cytology for lymphoma, prior radioimmunotherapy, or prior therapy with other human or humanized monoclonal antibodies (unless HACA tested negative) were ineligible. Other exclusion criteria were known HIV, hepatitis B or C positivity, known autoimmune disease or presence of autoimmune phenomena, infection or antibiotic use within 5 days, corticosteroids within 2 weeks, other cancer within 5 years (except non-melanoma skin cancer or cervical carcinoma in situ), and other conditions likely to interfere with study interpretation or procedures. Women of childbearing potential must have a negative pregnancy test, and patients of childbearing potential must practice birth control for at least 12 weeks after treatment.

Treatment—Veltuzumab was given on a weekly basis for 4 consecutive weeks. All patients were premedicated each week with an anti-histamine and an anti-pyretic, but no steroids were given routinely. During dose escalation, cohorts of 3-6 patients received veltuzumab at increasing dose levels of 120, 200, 375, and 750 mg/m$^2$, while subsequent patients received veltuzumab at 80, 120, 200 or 375 mg/m$^2$. For patients remaining stable in the absence of infusion reactions, guidelines for veltuzumab infusions allowed the infusion rate to be advanced every 15-30 minutes in increments of 50 mg/h for the 1$^{st}$ infusion and 100-200 mg/h for subsequent infusions. Otherwise, recommended actions included slowing the infusion rate for mild toxicity; interrupting the infusion for moderate toxicity for at least 15 minutes or until symptoms resolve and then resuming at the slowed infusion rate, if the patient was stable; and permanently discontinuing the infusion for more serious toxicity.

Data collection—CT scans (neck, chest, abdomen, pelvis, other sites of known disease) and physical examinations were obtained at baseline and 4 weeks after last infusion. Patients without disease progression continued CT scans and physical examination at 12 weeks and then every 3 months until the occurrence of disease progression. Bone marrow biopsy was required at baseline and in those patients with bone marrow infiltration only if needed to confirm a complete response. During infusions, patients were monitored for adverse reactions, with vital signs obtained every 15 min until completion, and then 30 and 60 min later. They continued to be monitored for adverse events at evaluations 4 and 12 weeks after the last infusion and then every 3 months until resolution of any treatment-related abnormalities or other changes warranting additional follow-up. Blood samples for routine safety laboratories (serum chemistry, hematology) and physical examinations were obtained prior to each infusion, 4 and 12 weeks after last infusion, and then every 3 months at follow-up evaluations until progression of disease.

Blood samples for B-cell counts (CD19+) were obtained prior to each infusion, at 1, 4, 8 and 12 weeks after last infusion, and during follow-up every 3 months until decreased levels returned towards baseline. Urinalysis, blood samples for T-cell levels (CD3+) and serum immunoglobulins were determined at baseline, prior to last infusion, 4 and 12 weeks after last infusion, and then during follow-up every 3 months until resolution of any treatment-related abnormalities. Blood samples for veltuzumab serum levels were obtained prior to and 30 minutes after each infusion, at 24, 48, 72 and 96 hours after the first and last infusions, and then at 1, 2, 3, 4, 8 and 12 weeks after last infusion. Blood samples for immunogenicity (HAHA; human anti-veltuzumab antibodies) were obtained at baseline, 4 and 12 weeks after last infusion, and then during follow-up if positive at 12 weeks.

Study Evaluations—Treatment responses were determined using international workshop criteria (Cheson et al., *J Clin Oncol.* 1999, 17:1244-1253), with each patient's best response classified as either complete response (CR), complete response unconfirmed (CRu), partial response (PR), stable disease, or progressive disease. Adverse events (AEs) were classified according to MedDRA system organ class and preferred term. Toxicity grading of AEs and laboratories utilized National Cancer Institute (NCI) Common Toxicity Criteria (CTC), version 3.0. Dose-limiting toxicity (DLT) was defined as any treatment-related Grade 3 or 4 toxicity or the following Grade 2 events: autoimmune reaction, asymptomatic bronchospasm, or generalized urticaria. All laboratory values were determined locally, except for veltuzumab serum levels and HAHA determinations, which were performed by the sponsor using an ELISA test. Pharmacokinetics following last infusion was evaluated with a single compartment model using WinNonLin 2.1 (Pharsight Corporation, Mountain View, Calif.).

Statistical Analysis—Descriptive statistics were used to summarize demographics, safety and laboratory data, and treatment response rates, including exact 95% confidence intervals where indicated. Progression-free survival (PFS), defined as the duration from the first day of study drug administration to the day of disease progression (based on physical or radiological (CT) evidence), death, or last contact, whichever occurred earliest, was summarized using descriptive statistics as well as statistics based on the Kaplan-Meier product-limit method. Patients were considered as censored if they never experienced disease progression or death. Duration of response, defined as the duration from the first day of onset of an objective response (OR), ie, CR, CRu, or PR, to the day of disease progression, death, or last contact, whichever occurred earliest, was summarized using similar methods.

men (range, 1-7), and most patients (89%) had received at least one prior rituximab-containing regimen. Based on WHO classification (Harris & Ferry, 2001), 55 patients had follicular lymphoma (FCL), while 27 patients had non-follicular lymphomas: diffuse large B-cell lymphoma (DLBCL, N=7), mantle cell lymphoma (MCL, N=7), small lymphocytic lymphoma (SLL, N=5), marginal zone lymphoma (MZL, N=6) [including nodal MZL (N=2) and extranodal MZL of mucosa-associated lymphoid tissue (MALT, N=4)], and lymphoplasmacytoid lymphoma (N=2). Published criteria were used to assign FLIPI and IPI scores for risk of poor outcome for patients with follicular and non-follicular lymphomas, respectively (Solal-Celigny et al., Blood 104:1258-1265, 2004). Demographics and patient characteristics are summarized in Table 5.

TABLE 5

Demographics and Baseline Information.

|  | All Patients (N = 82) | FCL[1] (N = 55) | Other[2] (N = 27) |
| --- | --- | --- | --- |
| Sex (M/F) | 34/48 | 21/34 | 13/14 |
| Age, median yrs (range) | 64 (33-85) | 61 (33-80) | 66 (43-85) |
| ECOG: 0, 1, 2 | 68, 18, 2 | 45, 10, 0 | 17, 8, 2 |
| Disease stage at study entry |  |  |  |
| I | 9 | 5 | 4 |
| II | 7 | 6 | 2 |
| III | 26 | 20 | 6 |
| IV | 39 | 24 | 15 |
| Yrs from diagnosis median (range) | 5.1 (1.2-31.5) | 5.1 (1.6-31.5) | 5.1 (1.2-15.3) |
| Prior treatment regimens |  |  |  |
| Number, median (range) | 1.5 (1-7) | 2 (1-7) | 1 (1-5) |
| Rituximab containing: 0, 1, ≧2 | 9, 49, 24 | 7, 31, 17 | 2, 18, 7 |
| Last treatment |  |  |  |
| Yrs from, median (range) | 1.8 (0.1-11) | 1.9 (0.1-8) | 1.6 (0.1-11) |
| Response (yes/no) | 76/6 | 53/2 | 23/4 |
| Duration of (mo), median (range) | 18.0 (2-143) | 18.0 (2-79) | 19.0 (2-143) |
| Elevated LDH | 17 | 13 | 4 |
| Bulky Disease >5 cm | 30 | 24 | 6 |
| FLIPI |  |  |  |
| Low (0-1) |  | 20 |  |
| Intermediate (2-3) |  | 31 |  |
| High (4-5) |  | 4 |  |
| IPI |  |  |  |
| Low (0-1) |  |  | 9 |
| Low/intermediate (2) |  |  | 12 |
| High/intermediate (3) |  |  | 5 |
| High (4-5) |  |  | 1 |
| Veltuzumab Dose Level |  |  |  |
| 80 mg/m$^2$ | 14 | 9 | 5 |
| 120 mg/m$^2$ | 21 | 17 | 4 |
| 200 mg/m$^2$ | 18 | 13 | 5 |
| 375 mg/m$^2$ | 26 | 14 | 12 |
| 750 mg/m$^2$ | 3 | 2 | 1 |

[1]Includes follicular grades 1 (N = 31), 2(N = 18), and 3(N = 4). Grades were not assigned for 2 patients.
[2]Includes diffuse large B-cell lymphoma (N = 7), mantle cell lymphoma (N = 7), marginal zone lymphoma (N = 6), small lymphocytic lymphoma (N = 5), and lymphoplasmacytoid lymphoma (N = 2).

Results

Patient Characteristics—A total of 82 patients (34 men, 48 women, median age 64 years) were enrolled. They were a median of 5 years from initial diagnosis and 1.8 years from last treatment. Most patients were in good performance status (83% ECOG 0) at study entry, but with widespread disease (79% Stage III/IV), and with 17 patients (21%) having elevated LDH, and 30 (40%) having at least one tumor mass >5 cm. All patients received at least one prior treatment regi- Drug Administration—Of the 82 patients, 78 received 4 infusions, while 3 patients with early progression of disease withdrew after completing 2-3 veltuzumab infusions, and one SLL patient with hives and chills at prior rituximab withdrew after similar Grade 1-2 reactions at the first veltuzumab infusion. Doses were otherwise administered as prescribed, based on the patient's body surface area and dose level, except for 3 patients given 1 or 2 of the 4 infusions at reduced doses due to allergic reactions, and one patient who was inadvertently administered one infusion at the next higher dose level. Infusion times are summarized in Table 6 for all doses given.

TABLE 6

Median Infusion Times (hours).*

| Dose (mg/m2) | N | Infusion 1 | Infusion 2 | Infusion 3 | Infusion 4 |
|---|---|---|---|---|---|
| 80 | 14 | 1.8 (1.1-3.6) | 1.4 (0.6-2.3) | 1.2 (0.8-1.6) | 1.2 (0.8-1.7) |
| 120 | 21 | 2.1 (1.1-4.6) | 1.4 (0.7-3.5) | 1.4 (0.7-3.5) | 1.3 (0.6-3.7) |
| 200 | 18 | 2.4 (1.3-8.1) | 1.3 (0.8-7.9) | 1.5 (0.8-8.8) | 1.3 (0.8-8.3) |
| 375 | 26 | 3.1 (2.1-7.6) | 2.1 (1.6-4.8) | 2.1 (1.7-3.8) | 2.1 (1.3-6.9) |
| 750 | 3 | 4.7 (3.8-6.2) | 2.6 (2.2-3.2) | 2.4 (2.0-2.8) | 2.5 (2.5-2.7) |

*Median (range) times in hours from start of infusion to termination of infusion.

Treatment Response—The single patient who withdrew at first infusion was unable to be assessed for efficacy. Of the 81 patients evaluated, 23 had disease progression at or prior to the first scheduled evaluation 4 weeks after treatment and underwent no further response evaluations. Otherwise, the best response in each patient prior to disease progression included 10 with CR, 7 with CRu, 16 with PR, and 25 with stable disease.

Calculating objective responses (OR=CR+CRu+PR), the overall OR and CR/CRu rates were 40.7% (33/81) and 21.0% (17/81), respectively. In follicular lymphoma, the OR and CR/CRu rates were 44% (24/55) and 27% (15/55), respectively, with both ORs and CR/CRu's occurring even after 2-5 prior rituximab-regimens, among follicular patients with less favorable prognosis (FLIPI≧2, elevated LDH, bulky disease>5 cm), and at all dose levels including 80 mg/m$^2$. Among the other non-follicular lymphomas, the overall OR and CR/CRu rates were 35% (9/26) and 27% (7/26), respectively. This included 5/6 MZL patients with ORs (83%), including 2 CR/CRu's (33%), one at 80 mg/m$^2$, and partial responses in 3/7 DLBCL patients (43%), and 1/7 MCL patients (14%). Table 7 summarizes these results.

TABLE 7

Objective Treatment Responses.*

| | OR | CR/CRu |
|---|---|---|
| All Evaluable Patients (N = 81) | 40.7% (33/81) | 21.0% (17/81) |
| Follicular Lymphoma (N = 55) | 43.6% (24/55) | 27.3% (15/55) |
| Dose (mg/m$^2$): 80 | 22.2% (2/9) | 11.1% (1/9) |
| 120 | 41.2% (7/17) | 29.4% (5/17) |
| 200 | 46.2% (6/13) | 30.8% (4/13) |
| 375 | 50.0% (7/14) | 21.4% (3/14) |
| 750 | 100% (2/2) | 100% (2/2) |
| FLIPI: 0-1 | 55.0% (11/20) | 40.0% (8/20) |
| ≧2 | 37.1% (13/35) | 20.0% (7/35) |
| Prior Rituximab: 0 | 57.1% (4/7) | 42.9% (3/7) |
| 1 | 45.2% (14/31) | 22.6% (7/31) |
| 2-5 | 35.3% (6/17) | 29.4% (5/17) |
| Elevated LDH: Yes | 23.1% (3/13) | 15.4% (2/13) |
| No | 50.0% (21/42) | 31.0% (13/42) |
| Bulky Disease(>5 cm): Yes | 25.0% (6/24) | 8.3% (2/24) |
| No | 58.1% (18/31) | 41.9% (13/31) |
| Non-Follicular (N = 26) | 34.6% (9/26) | 26.9% (7/26) |
| Marginal zone lymphoma[1] | 83.3% (5/6) | 33.3% (2/6) |
| Diffuse large B-cell lymphoma[2] | 42.9% (3/7) | 0.0% (0/7) |
| Mantle cell lymphoma[3] | 14.3% (1/7) | 0.0% (0/7) |
| Small lymphocytic lymphoma[4] | 0.0% (0/4) | 0.0% (0/4) |
| Lymphoplasmacytoid lymphoma[5] | 0.0% (0/2) | 0.0% (0/2) |

*Best response prior to disease progression based on Cheson criteria (OR = CR + CRu + PR, CR = complete response, CRu = unconfirmed CR, PR = partial response, SD = stable disease, POD = progression of disease)

TABLE 7-continued

Objective Treatment Responses.*

| | OR | CR/CRu |
|---|---|---|

[1]MZL: 1 CR (80 mg/m$^2$), 1 CRu (375 mg/m$^2$), 3 PR (80 mg/m$^2$, 2 × 200 mg/m$^2$), 1 SD (120 mg/m$^2$)
[2]DLBCL: 3 PR (80 mg/m$^2$, 2 × 375 mg/m$^2$), 4 POD (80 mg/m$^2$, 2 × 120 mg/m$^2$, 200 mg/m$^2$)
[3]MCL: 1 PR (375 mg/m$^2$), 3 SD (200 mg/m$^2$, 375 mg/m$^2$, 750 mg/m$^2$), 3 POD (120 mg/m$^2$, 2 × 375 mg/m$^2$)
[4]SLL: 2 SD (375 mg/m$^2$), 2 POD (80 mg/m$^2$, 375 mg/m$^2$);
[5]LPL: 2 SD (200 mg/m$^2$, 375 mg/m$^2$)

For all 55 follicular patients, based on Kaplan-Meier estimates, the median TTP was 6.7 months (95% CI: 3.7-9.3 mo) and the median time from first infusion to the onset of an OR (TTR) was 3.3 months (95% CI: 1.7-3.7 mo). The 24 patients with an OR had a median DR of 10.2 months (95% CI: 6.0-22.6 mo) and median TTP of 15.2 mo (95% CI: 9.5-28.2 mo). Kaplan-Meier DR and TTP curves for the 24 responders are presented in FIG. 15. For the 15 follicular patients who achieved CR/CRu, the Kaplan-Meier estimated median DR and TTP were 19.7 months (95% CI: 8.7-32.5 mos.) and 24.2 months (95% CI: 13.8-34.4 mos.), respectively, including 5 patients still continuing long-lived responses 15.9 to 37.6 months from the date of 1$^{st}$ infusion. Although the sample sizes are small, there was no decrease in the durability of complete responses at lower doses, and the single follicular patient with a complete response at 80 mg/m$^2$ is still in remission 15.9 months after the 1$^{st}$ infusion. Among the non-follicular histologies, the 2 complete responses that occurred (one at 80 mg/m 2), as well as one long-lived stable response (all in marginal zone lymphoma), were still continuing 15-24 months after treatment.

Adverse Events—Seventy-eight patients had one or more adverse events during the study. Of 48 patients with events considered at least possibly treatment-related, only one patient had a Grade 3 event, hypogobulinemia which developed during long-term remission >1 year after treatment. Otherwise, all events considered at least possibly treatment-related were mild-moderate (Grades 1-2), most of which were infusion reactions that occurred predominantly at first infusion, with ≦11 patients having such events at each of the subsequent infusions. Table 8 summaries the most frequent events.

Ten patients had serious adverse events, none of which were considered even possibly treatment-related, including pre-existing atrial fibrillation and events occurring during the treatment period (trauma, cellulitis, sepsis), within the 12-week post-treatment evaluation period (decreased performance status, back pain, incidental finding of A-V malformation) or during long-term follow-up (bladder tumor, pulmonary embolism, urinary fungal infection).

TABLE 8

Adverse Events Occurring in ≧5% of Patients.

| | Patients with Events (Grade ≧3) | Patients with Events Considered at Least Possibly Treatment Related (Grade ≧3) |
|---|---|---|
| Fatigue | 23% (0%) | 13% (0%) |
| Pruritis | 13% (0%) | 7% (0%) |
| Fever | 13% (0%) | 9% (0%) |
| Headache | 11% (0%) | 4% (0%) |
| Asthenia | 11% (0%) | 9% (0%) |
| Dyspnea | 10% (0%) | 4% (0%) |
| Cough | 10% (0%) | 0% (0%) |

TABLE 8-continued

Adverse Events Occurring in ≧5% of Patients.

| | Patients with Events (Grade ≧3) | Patients with Events Considered at Least Possibly Treatment Related (Grade ≧3) |
|---|---|---|
| Abdominal pain | 9% (0%) | 4% (0%) |
| Chills | 9% (0%) | 7% (0%) |
| Arhralgia | 9% (0%) | 2% (0%) |
| Diarrhea | 7% (0%) | 5% (0%) |
| Nausea | 7% (0%) | 5% (0%) |
| Nasal Congestion | 7% (0%) | 4% (0%) |
| Peripheral Edema | 6% (0%) | 2% (0%) |
| Back Pain | 6% (1%) | 1% (0%) |
| Myalgia | 6% (0%) | 2% (0%) |
| Dizziness | 6% (0%) | 4% (0%) |
| Pharyngeal pain | 6% (0%) | 4% (0%) |
| Hypertension | 5% (0%) | 2% (0%) |
| Urticaria | 5% (0%) | 1% (0%) |
| Constipation | 5% (0%) | 1% (0%) |
| Anemia | 5% (2%) | 0% (0%) |

Eighteen patients (22%) had one or more infections. None of the 4 Grade 3-4 infections were considered treatment-related, including 3 infections (sepsis, cellulitis, fungal urine infection) requiring IV antibiotics and one infection (not otherwise specified) treated with multiple oral antibiotics. Otherwise, all infections were Grade 1-2 events treated with oral medications, predominantly involving the respiratory tract, urinary tract or sinuses.

Safety Laboratories—Blood samples for hematology and serum chemistries were obtained prior to each infusion, 4 and 12 weeks after the last infusion, and then every 3 months as needed at follow-up evaluations. No abnormal pattern of changes in standard safety laboratories occurred and few patients had increases in toxicity grades after treatment (Table 9).

TABLE 9

Changes of Safety Laboratories: Patients with Increases in CTC v 3.0 Toxicity Grades From Baseline (N = 82).

| | Maximum Post-Treatment Grade | | | |
|---|---|---|---|---|
| | 1 | 2 | 3 | 4 |
| Hematology | | | | |
| Hemoglobin | 10 | 5 | 1 | 0 |
| WBC | 11 | 5 | 1 | 0 |
| ANC | 2 | 4 | 2 | 0 |
| Platelets | 4 | 2 | 0 | 0 |
| Serum Chemistry | | | | |
| Creatinine | 1 | 1 | 1 | 0 |
| Total bilirubin | 5 | 0 | 0 | 0 |
| Alkaline phosphatase | 6 | 0 | 0 | 0 |
| SGPT (ALT) | 4 | 0 | 0 | 0 |
| SGOT (AST) | 4 | 1 | 0 | 0 |

* Grade 3 events: 3 patients had abnormal laboratories (grade 2 creatinine, grade 2 ANC, grade 1 hemoglobin) at study entry which became Grade 3 at week 12, while the other patient maintained normal WBC and ANC levels until week 12.

Pharmacokinetics—A total of 72 patients who completed all 4 infusions received all veltuzumab doses at the intended dose, had serum samples collected after both first and last infusions, and had negative ELISA assay results prior to receiving veltuzumab (one patient was excluded due to an apparent interfering serum factor of unknown cause) were included in the analysis of pharmacokinetics. Table 10 summarizes the mean serum levels prior to and 30 min following each infusion. At all doses, the mean peak levels at the first infusion exceeded the 25-µg/mL value considered important for maintaining efficacy with rituximab (Berinstein et al., *Ann Oncol* 9: 995-1001, 1998; Gordon et al., *J Clin Oncol* 23:1096-1102, 2005; Cartron et al., *Crit Rev in Oncol Hematol* 62:43-52, 2007). The antibody accumulated with infusion number at all doses, and even at 80 mg/m², the mean trough serum levels exceeded the 25-µg/mL value by the last infusion. Post-treatment serum samples were scheduled to be collected 30 min after last infusion, 1, 2, 3 and 4 days later, and at 1, 2, 3, 4, 8 and 12 weeks.

TABLE 10

Veltuzumab Serum Levels (Mean ± SD): Pre- and Post-Infusion Results (µg/mL).

| | 80 mg/m² (N = 12) | 120 mg/m² (N = 19) | 200 mg/m² (N = 14) | 375 mg/m² (N = 24) | 750 mg/m² (N = 3) |
|---|---|---|---|---|---|
| Infusion 1 | | | | | |
| Pre | 1.3 ± 1.5 | 0.3 ± 0.5 | 0.3 ± 0.6 | 0.1 ± 0.3 | 0.7 ± 0.5 |
| Post | 39 ± 9 | 59 ± 13 | 94 ± 22 | 194 ± 35 | 474 ± 33 |
| Infusion 2 | | | | | |
| Pre | 11 ± 5 | 18 ± 11 | 28 ± 18 | 75 ± 45 | 222 ± 158 |
| Post | 48 ± 15 | 86 ± 31 | 125 ± 44 | 276 ± 90 | 632. ± 99 |
| Infusion 3 | | | | | |
| Pre | 20 ± 7 | 30 ± 19 | 57 ± 29 | 118 ± 51 | 385 ± 77 |
| Post | 55 ± 15 | 92 ± 44.4 | 140 ± 49 | 335 ± 91 | 801 ± 29 |
| Infusion 4 | | | | | |
| Pre | 27 ± 11 | 43 ± 26 | 72 ± 41 | 173 ± 69 | 495 ± 64 |
| Post | 68 ± 25 | 100 ± 37 | 170 ± 67 | 404 ± 105 | 996 ± 66 |

A single-compartment (mono-exponential) model was fit to all available post-treatment serum-level data in each of the 72 patients. Table 11 summarizes the resulting fit-determined pharmacokinetic parameters showing that the mean Cmax and AUC increased with dose level, while the clearance (CL) values showed no consistent pattern of dose dependence. Most importantly, the mean $T_{1/2}$ values appeared comparable at all doses, and even at 80 mg/m², the antibody remained in circulation with a mean half-life of 20 days. Although a formal comparison was not performed, there were no major differences in mean peak and trough or post-treatment pharmacokinetics for the 50 follicular patients compared to the 22 other non-follicular patients (data not shown).

TABLE 11

Veltuzumab Serum Levels (Mean ± SD): Pharmacokinetics After 4th Infusion.

|  | 80 mg/m² (N = 12) | 120 mg/m² (N = 19) | 200 mg/m² (N = 14) | 375 mg/m² (N = 24) | 750 mg/m² (N = 3) |
|---|---|---|---|---|---|
| Cmax (µg/mL) | 56 ± 19 | 91 ± 34 | 155 ± 60 | 358 ± 90 | 884 ± 90 |
| $T_{1/2}$ (d) | 19.7 ± 9.4 | 14.7 ± 7.7 | 18.4 ± 9.8 | 13.3 ± 4.1 | 16.1 ± 1.4 |
| $AUC_{0 \to \infty}$ (d × µg/mL) | 1487 ± 646 | 1952 ± 1204 | 4188 ± 2286 | 7191 ± 3262 | 20647 ± 3313 |
| CL (mL/d/m²) | 67 ± 33 | 108 ± 103 | 230 ± 604 | 72 ± 52 | 37 ± 7 |

Similar to what has been reported with rituximab (Berinstein et al., *Ann Oncol* 9: 995-1001, 1998; Gordon et al., *J Clin Oncol* 23:1096-1102, 2005; Cartron et al., *Crit. Rev in Oncol Hematol* 62:43-52, 2007), both mean and median peak and trough serum levels at each infusion were generally higher among patients with objective responses than in nonresponders, and in spite of small number of patients, even for those patients treated at the lowest dose of 80 mg/m². Median pre- and post-infusion results are summarized in Table 12 for all follicular patients with available data.

TABLE 12

Veltuzumab Serum Levels During Treatment for Follicular Lymphoma Responders and Nonresponders.

|  |  | Preinfusion | | Postinfusion | |
|---|---|---|---|---|---|
| Infusion | Responder | N | Median (µg/mL) | N | Median (µg/mL) |
| 1 | Yes | 20 | 0.0 | 16 | 90.7 |
|  | No | 21 | 0.0 | 15 | 59.0 |
| 2 | Yes | 20 | 36.5 | 16 | 152.9 |
|  | No | 20 | 16.1 | 14 | 83.5 |
| 3 | Yes | 20 | 69.2 | 16 | 201.0 |
|  | No | 21 | 33.0 | 16 | 75.2 |
| 4 | Yes | 20 | 93.0 | 16 | 201.0 |
|  | No | 21 | 43.0 | 16 | 85.4 |

B-cell and Other Immunological Changes—Peripheral blood B-cell levels (CD19+) were to be determined at baseline, prior to each infusion, at 4 weeks following the last infusion, and then at 3-month intervals until recovery to baseline. At study entry, 68 patients had low or low-normal peripheral blood B-cell levels (1-256 cells/µl, median 60), 9 patients (including all 5 SLL patients) had elevated levels (572-14,712 cells/µl, median 1,782), and 5 patients did not have baseline levels determined.

Figure 15:
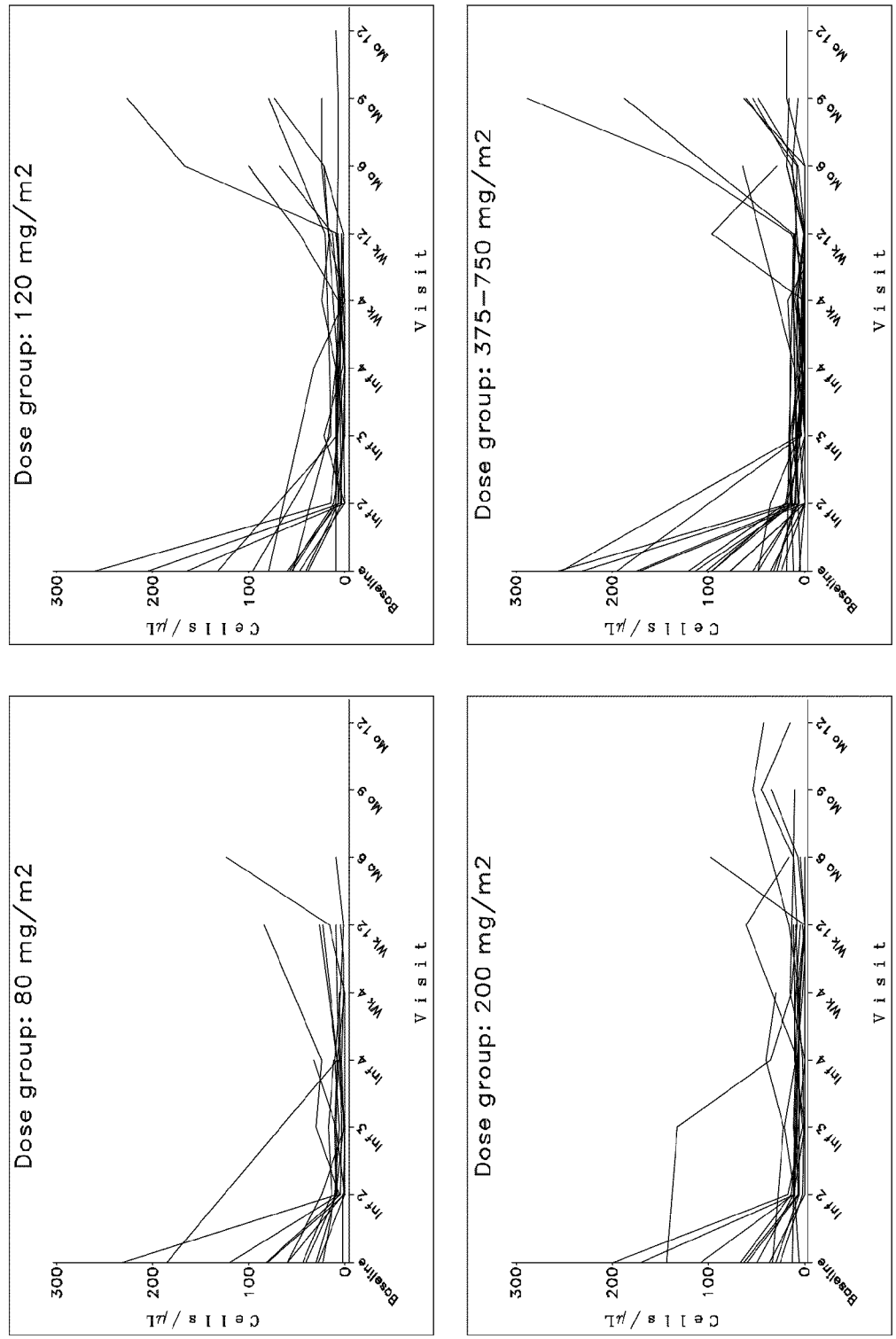
FIG. 15. B-cell levels for NHL patients treated with veltuzumab in different dose groups measured at baseline, prior to infusions 2, 3 and 4, at 4 and 12 weeks later, then at 3-month intervals for up to 12 months after last infusion.

FIG. 15 graphs the course of B-cell levels for all patients who had non-elevated B-cell levels at baseline and at least one sample obtained during treatment. At laboratories where B-cell levels were reported as percentage of total lymphocytes, decreases below the lower limit of quantitation (typically 1%) could not be determined and for analysis were conservatively set at the limit prior to converting results to absolute cell counts. As such, the actual extent of B-cell depletion is likely more complete, but nonetheless, the results appear comparable for all the dose levels, including the lowest dose level of 80 mg/m².

The B-cells generally remained depleted until onset of recovery 6 months after last infusion, with decreased values then returning towards baseline by 9-12 months, and there is no evidence that B-cell depletion is less durable at lower dose levels, although long-term data are still limited for patients treated at the most recent dose level of 80 mg/m².

Figure 14:
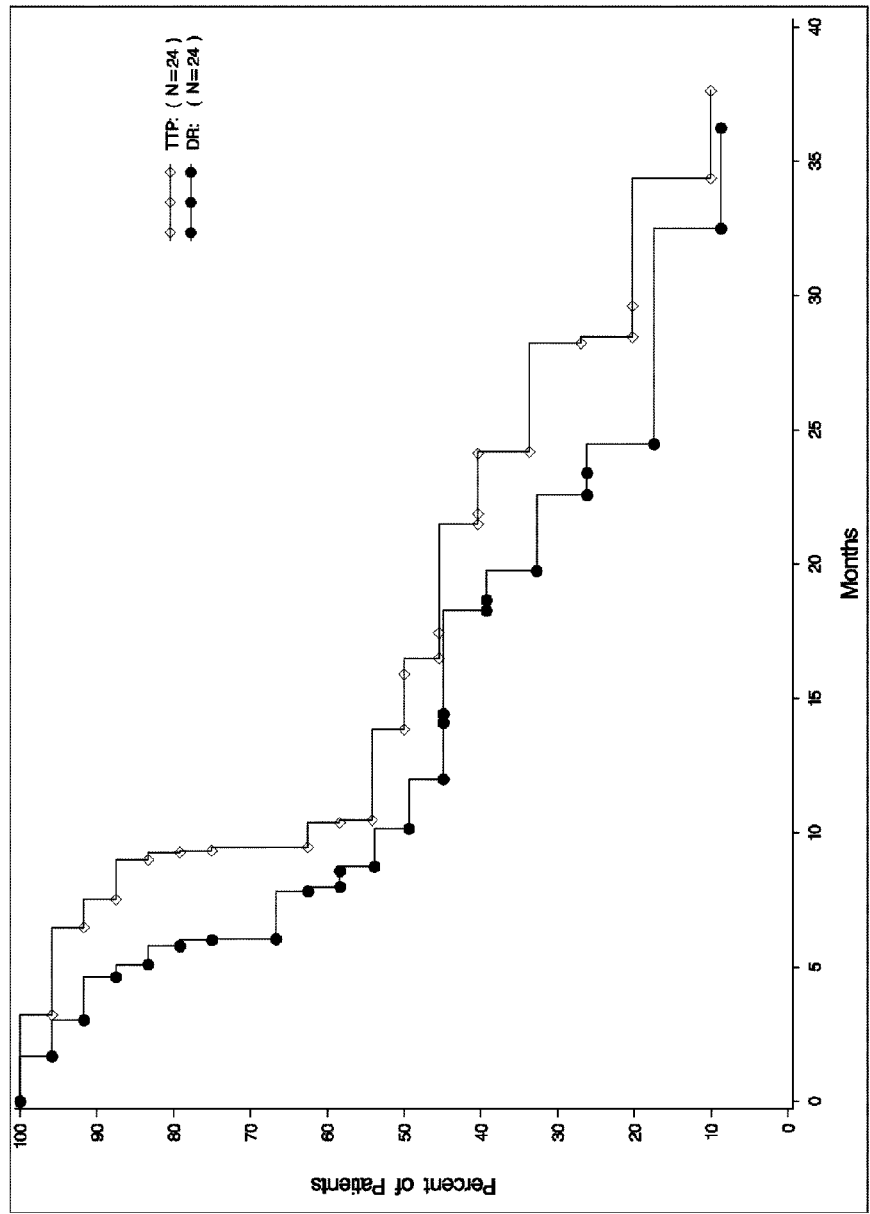
FIG. 14. Kaplan-Meier estimates of duration of response (DR) and time to progression (TTP) for 24 follicular lymphoma responders in human studies of veluzamab effects in non-Hodgkin's lymphoma.

The few patients with elevated B-cell levels at study entry were not included in FIG. 14 for clarity. In spite of greatly increased baseline values, particularly for the SLL patients, their B-cell levels were also substantially decreased with treatment (median 96% decrease), including a 94% decrease in one patient treated at 80 mg/m². However, these were primarily short-lived responses, most beginning to return towards elevated baseline values by 12 weeks after the last infusion.

Quantitative serum immunoglobulin and T-cell levels were to be obtained from blood samples evaluated at baseline, prior to last infusion, 4 and 12 weeks later, and then every 3 months for patients remaining in follow-up. There was no consistent pattern of clinically significant decreases during the 12-week study period or in smaller subsets of patients followed up to one year after last infusion, with median changes from baseline being small at most time points (typically <5% for IgA and IgG, <15% for T cells, <20% for IgM).

Immunogenicity (HAHA)—Seventy patients had at least one post-treatment serum sample at 4 weeks (N=58), 12 weeks (N=53), 6 months (N=8), or one year (N=2) after last infusion analyzed for HAHA by ELISA assay. One SLL patient with prior rituximab exposure was negative at study entry, but developed elevated titers (3,380 ng/mL) 4 weeks after treatment without any apparent clinical consequence. All other samples were negative (<50 ng/mL).

Discussion

Despite evidence of cell killing mediated by antibody dependent cellular cytotoxicity (ADCC), complement dependent cytotoxicity (CDC), and direct signaling with apoptosis effects, the clinically relevant mechanisms of action of anti-CD20 immunotherapy in B-cell malignancies or various autoimmune disorders remains uncertain (Glennie et al., *Mol Immunol* 44:3823-3837, 2007). As such, clinical trials of second generation anti-CD20 antibodies remain necessary and most of these have focused on antibody doses close to or higher than that typically given with rituximab (Morschhauser et al., *Blood* 110:199a, 2007; Hagenbeek et al., *Blood* 111:5486-5495, 2008; Coiffier et al., *Blood* 111:1094-1100, 2008). However, several lines of inquiry, including animal studies (Example 15), as well as independent studies of shaving effects in CLL (Kennedy et al., *J Immunol* 172:3280-3288, 2004; Williams et al., *J Immunol* 177:7435-7443, 2006), have suggested that lower doses than the typical 375 mg/m$^2$ dose used with rituximab should be explored. The present results demonstrate that at least with veltuzumab, much lower doses than 375 mg/m$^2$ are efficacious, both with regard to clinical responses and ability to deplete peripheral blood B-cells.

Most patients in this study had follicular lymphoma for which veltuzumab had an overall 44% objective response, between the 48% rate reported with rituximab in the initial pivotal trial of rituximab-naïve patients (McLaughlin et al, *J Clin Oncol* 16:2825-2833, 1998) or 40% in patients who previously responded to rituximab (since many patients here had prior exposure to one or more rituximab-containing regimens) (Davis et al., *J Clin Oncol* 18:3135-3143, 2000). Similarly, the rate of complete responses, either 27% CR/CRu or 16% for CRs alone, exceeded the complete response rates of 6% and 11% reported in those groups, although different criteria were used in the earlier studies.

It is important that veltuzumab responses, including complete responses, occurred in patients who had received multiple prior rituximab-regimens as well in patients generally considered at risk for less-favorable outcome (higher FLIPI scores, elevated LDH, tumor masses >5 cm). The highest response rates occurred in the small number of rituximab-naïve patients, achieving 57% ORs and 43% CR/CRu's.

The 10.2 months median DR found for all FL responders in this study is comparable with the 11.2 months DR reported in relapsed/refractory, indolent NHL patients after a first application of rituximab (McLaughlin et al, *J Clin Oncol* 16:2825-2833, 1998). Although a longer 15.0 months median DR was reported in patients retreated with rituximab, they all had achieved an objective response to prior rituximab lasting at least 6 months (Davis et al., *J Clin Oncol* 18:3135-3143, 2000). In contrast, patients in this study could not have progressed within 6 months of rituximab, but an objective response was not required. As such, they may likely be more refractory and require more time for veltuzumab to be effective, consistent with the median time to onset of response of 3.3 months in this study compared to 1.6 months in both of the other rituximab studies (McLaughlin et al., 1998; Davis et al., 2000), and also consistent with the relatively long median TTP for responders of 15.2 months seen in this study.

As discussed above, there also appeared to be a greater number of complete responses with veltuzumab compared to these other studies. This is particularly important because patients with CR/CRu's in this study generally had durable responses, with the median DR and PFS currently being 19.7 and 24.2 months, respectively, both of which may increase further since 5 patients are still continuing with long-lived responses (15.9-37.6 months). Thus, despite the lower dose levels studied here, efficacy results with veltuzumab appeared favorable compared to rituximab when given once-weekly for 4 weeks.

Among the non-follicular histologies, veltuzumab achieved an overall objective response rate of 35% with 27% CR/CRu's. Veltuzumab did particularly well in marginal zone lymphoma, with ORs in 5/6 patients (83%) having either extranodal MALT or nodal type disease, including 3 long-term responses (15-24 months), one at a dose level of only 80 mg/m$^2$. Thus, consistent with favorable responses previously reported with rituximab (Tsimberidou et al., *Cancer* 107:125-135, 2006; Conconi et al., *Blood* 102:2741-2745, 2003), veltuzumab shows promising activity for use in marginal zone lymphoma.

In DLBCL, no complete responses occurred, but 3/7 patients achieved a partial response, including one patient treated with 80 mg/m$^2$. The resulting OR rate of 43% obtained here with 4 weekly doses of veltuzumab is comparable to the 37% rate reported in DLBCL with 8 weekly doses of rituximab (Coiffier et al., *Blood* 92:1927-1932, 1998). These findings of promising activity suggest that veltuzumab may be useful in combination with chemotherapy in this population, similar to what has been found with rituximab (Czuczman et al., *J Clin Oncol* 22:4711-4716, 2004; Coiffier et al., *N Engl J Med* 346:235-242, 2002; Habermann et al., *J Clin Oncol* 24:3121-3127, 2006), which is approved for use in DLBCL in combination with CHOP.

Only one of seven patients with mantle cell lymphoma had an objective response, a short-lived partial response in a patient treated with veltuzumab at 120 mg/m$^2$. This is consistent with modest response rates, and predominantly partial responses, reported with single-agent rituximab in this disease (Igarashi et al., *Ann Oncol* 13:928-943, 2002; Foran et al., *J Clin Oncol* 18:317-324, 2000). Patients with relapsed small lymphocytic lymphoma are known to be relatively refractive to single-agent rituximab (McLaughlin et al., 1998; Foran et al., *J Clin Oncol* 18:317-324, 2000), and none of the few patients in this study had an objective response.

However, veltuzumab did have other evidence of activity in SLL, since all the patients had elevated B-cell levels at study entry (3 above 10,000/mm$^3$) which decreased after the first veltuzumab infusion and remained decreased for at least 4 weeks after the last infusion, and this included one patient treated at 80 mg/m$^2$ with initial levels >10,000/mm$^3$ subsequently decreased by 94%. Two studies of rituximab in patients with Waldenström's macroglobulenemia and immunocytoma reported only modest response rates with no complete responses (Foran et al., *J Clin Oncol* 18:317-324, 2000; Gertz et al., *Leuk Lymphoma* 45:2047-2055, 2004), and thus it is not surprising that neither of the 2 patients in this study with lymphoplasmacytic lymphoma had an objective response.

Concerning veltuzumab pharmacokinetics, at 375 mg/m$^2$ the mean peak and trough serum antibody levels achieved with veltuzumab were comparable to values reported for rituximab (Berinstein et al., *Ann Oncol* 9: 995-1001, 1998). Even at 80 mg/m$^2$, B-cell depletion occurred after the first infusion, antibody serum levels after the first infusion exceeded the 25-µg/mL value associated with maintained efficacy (Berinstein et al., 1998; Gordon et al., 2005; Cartron et al. 2007), and continued to increase with each successive infusion, and veltuzumab remained in circulation after last infusion with a half-life comparable to or at least as long as reported in rituximab studies (Berinstein et al., 1998; Cartron et al. 2007).

We found the same relationship of higher serum levels in responders reported with rituximab (Berinstein et al., 1998; Gordon et al., 2005; Cartron et al., 2007), and although the numbers were small, this trend was still seen even for patients only treated at the lowest dose of 80 mg/m$^2$. These pharmacokinetic and pharmacodynamic findings suggest the lower veltuzumab doses were adequate to overcome the antigenic sink, thus supporting the demonstration of clinical activity that occurred at all dose levels in this study, including 80 mg/m$^2$.

An added benefit of using lower doses is the decreased infusion time. With veltuzumab, the median first infusion times were 4.7 hours at 750 mg/m$^2$, 3.1 hours at 375 mg/m$^2$, and 1.8-2.4 hours at lower doses, while median times for subsequent infusions were 2.1-2.6 hours at 375 or 750 mg/m$^2$, and 1.2-1.5 hours at lower doses. At these shorter infusion times, there were no serious infusion reactions or increases in the frequency of more common infusion reactions. This is important, because the protocol limited the rate of infusions in this first study, so that even more rapid administrations are likely possible with this agent. Veltuzumab also had no significant clinical impact on standard safety laboratories, T-cell levels, or serum immunoglobulins. Only one case of HAHA response occurred, of uncertain clinical significance; otherwise, there was no evidence of veltuzumab immunogenicity.

The first clinical study of rituximab evaluated single doses of 10-500 mg/m², with several partial responses achieved at doses of 100 mg/m² and above (Maloney et al., *Blood* 84: 2457-2466, 1994). In the next rituximab study, only doses of 125 mg/m² and higher were given once weekly for 4 weeks, and the now standard 375-mg/m² dose was selected at that point for further development, apparently on the basis of logistical rather than scientific considerations, since the actual response rates (all partial responses) were identical at each dose level tested (Maloney et al., *J Clin Oncol* 15:3266-3274, 1997). A better understanding of pharmacokinetics and factors influencing patient response is clearly needed to optimize dosing (Cartron et al., *Crit. Rev in Oncol Hematol* 62:43-52, 2007), but after the initial approval of rituximab, 375-mg/m² and even higher doses were accepted for clinical use with anti-CD20 antibodies without critical evaluation, or consideration of lower levels. However, the recent evidence of "shaving" in chronic lymphocytic leukemia has led others to suggest that low doses may be effective in that disease (Kennedy et al., *J Immunol* 172:3280-3288, 2004; Williams et al., *J Immunol* 177:7435-7443, 2006). Low doses also would be expected to be effective against lower CD20 tumor burdens, such as lymphoma patients with small volume disease or undergoing maintenance therapy, or in B-cell mediated autoimmune diseases, where there may be much less of a CD20 sink than in malignant diseases, and where overly aggressive B-cell suppression may not be needed nor desirable.

In summary, this Example demonstrated that veltuzumab is not only well-tolerated, but also that low doses are active, with B-cell depletion and complete responses occurring at all doses evaluated, including 80 mg/m². Lower doses are also important because of the opportunity to deliver veltuzumab by subcutaneous injection using a more concentrated antibody formulation, as has been shown in animal models (Example 15).

Example 25 hA20 Variants

Materials and Methods

PCR were performed according to the standard PCR protocol. DNA sequencing was performed by SeqWright (Houston, Tex.). The restriction enzymes were purchased from New England Biolabs. The primers were made through Fisher Scientific.

A. Variant V102Y

V102Y is the variant of hA20 with one amino acid change of Val to Tyr at the 102 position (Kabat's numbering) in the CDR3 of VH. SEQ ID NOS 6 & 21, respectively.

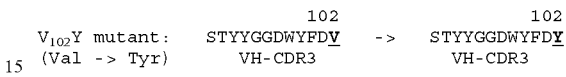

Thus, CDRH3 in V102Y is STYYGGDWYFDY (SEQ ID NO:21).

Vector Construction and Cloning Scheme

Four primers were used:

```
5' V102Y primer (40 mers)
                                      (SEQ ID NO: 22)
CGGTGACTGGTACTTCGATTACTGGGGCCAAGGCACCACG 3' V102Y primer (40 mers)
                                      (SEQ ID NO: 23)
CGTGGTGCCTTGGCCCCAGTAATCGAAGTACCAGTCACCG 5' Xho I primer (20 mers)
                                      (SEQ ID NO: 24)
CCTCGAGCACACAGGACCTC 3' Hind III primer (20 mers)
                                      (SEQ ID NO: 25)
AAAGCTTGCGGCCGCGATCC
```

The cloning scheme was as follows:
DNA template: hA20-IgG-pdHL2
  5' Xho I primer & 3' V102Y primer
  PCR product #1: 510 bp
DNA template: hA20-IgG-pdHL2
  5' V102Y primer & 3' Hind III primer
  PCR product #2: 210 bp
PCR product #1 & #2 were purified from gel, mixed in equal molar amounts as template and PCR with 5' Xho I & 3' Hind III as primers to generate PCR product #3 (680 bp), which was cloned into pGEMT and confirmed with XhoI and HindIII digestion, followed by sequencing. Ligating PCR product #3 with the Xho I/Hind III restricted fragment of hA20-IgG-pdHL2 completed the expression vector for V102Y, designated as V102Y-hA20-IgG-pdHL2).

| Nomenclature | Alternate Name | H-CDR3 101 | 102 | Fc 239 | 332 | Note | |
|---|---|---|---|---|---|---|---|
| v-mab | Veltuzumab; hA20 | D | V | S | I | Slower off-rate | |
| V102Y | | • | Y | • | • | CDR variant of v-mab with similar or equivalent in vitro and in vivo properties | Ex. 25A |
| YDE | | • | Y | D | E | Fc variant of V102Y with enhanced ADCC | Ex. 25B |
| v-mab-DE | | • | • | D | E | Fc variant of v-mab with enhanced ADCC | Ex. 25C |
| D101N | | • | • | • | • | CDR variant of v-mab with faster off-rate | |

The amino acid residue identical to that of v-mab at the corresponding position is indicated with •

Transfection and Protein Purification

V102Y-hA20-pdHL2 (30 μg) was linearized by digestion with Sal I, followed by phenol, chloroform extraction, and precipitate with 100% ethanol and ammonium acetate. The DNA pellet was resuspended into electroporation buffer (20 mM HEPES, pH 7.0; 137 mM NaCl, 5 mM KCl, 0.7 mM $Na_2HPO_4$, and 6 mM Dextrose), then mixed with $2.8 \times 10^6$ SpESF cells and electroporated with electroporator GenePulser Xcell BioRad @ capacitance 25 μF, 450 V, resistance infinite ohms, 4 mm cuvette. The medium was added and plated on 96-wells plates.

After 48 hours, equal volume of the selection medium containing 0.2 μM MTX was added. About 10 days, the clones were screen by ELISA using mouse anti-hA20 antibody coated on the plates and anti-human Fc-HRP conjugate. The color was developed with OPD and $H_2O_2$.

The clone with the highest productivity (42 mg/L) was selected and designated as 3D10. V102Y was made in roller bottles, purified with protein A, and its purity shown by SDS-PAGE and size-exclusion HPLC. Other characterizations included off-rate determination and ADCC assay.

B. Variant YDE

YDE is a mutant of V102Y with two 2 amino acid mutations on the CH2 domain of Fc: S 239 D (TCA→GAT) & I 332 E (ATC->GAA)

Like V102Y, CDRH3 in YDE is STYYGGDWYFDY (SEQ ID NO:21).

Vector Construction and Cloning Scheme

Six primers were designed for the two amino acid mutations:

```
5' PstI-Fc (20 mers)
5' CTCTGCAGAGCCCAAATCTT       (SEQ ID NO: 26)

3' S239D (23 mers)
5' AGAGGAAGACATCCGGTCCCCCC    (SEQ ID NO: 27)

5' S239D (23 mers)
5' GGGGGGACCGGATGTCTTCCTCT    (SEQ ID NO: 28)

3' I332E (23 mers)
5' ATGGTTTTCTCTTCGGGGGCTGG    (SEQ ID NO: 29)

5' I332E (23 mers)
5' CCAGCCCCCGAAGAGAAAACCAT    (SEQ ID NO: 30)

3' PstI-Fc (20 mers)
5' ACCTGCAGGCGGCCGTCGCA       (SEQ ID NO: 31)
```

The cloning scheme was as follows:
DNA template: 1826-SV3 (an in-house staging vector)
PCR#1: 5' PstI-Fc & 3' S239D primers->207 bp
PCR#2: 5' S239D & 3' I332E primers->303 bp
PCR#3: 5' I332E & 3' PstI-Fc primers->477 bp Each PCR product was gel-purified, mixed in equal molar concentration to obtain PCR#4 (941 bp) using 5' PstI-Fc and 3' PstI-Fc as primers. PCR#4 was cloned into pGEMT and confirmed by sequencing. The fragment was then digested from pGEMT with PstI and cloned into an intermediate vector, 1826-SV3, which was also digested with PstI. Ligating PCR#4 cut from the staging vector with EagI with the EagI-restricted V102Y-hA20-IgG-pdHL2 completed the construction of the final YDE-hA20-pdHL2.

Transfection and Protein Purification

The same procedures as described above for V102Y were used to obtain the production clone for YDE, which was purified from cell culture by protein A, and its purity shown by SDS-PAGE and SE-HPLC. YDE was shown to have enhanced ADCC compared to either v-mab or V102Y.

C. Variant v-mab-DE v-mab-DE is a Fc variant of v-mab, with the same amino acid mutations on the CH2 domain of Fc as YDE. The same primers and cloning scheme as described for YDE in Example 2 were used in the construction of the expression vector v-mab-DE-hA20-pdHL2, which has not been transfected.

ADCC Assays of hA20 Variants

ADCC assay was performed as follows. Briefly, Daudi cells were plated at $10^4$ cells/well in 50 μL of assay media (RPMI 1640 no phenol red, 1% Glutamax, 1% PenStrep). One set of wells received only the media for background control and another set of wells received cells only and served as the control for maximum cell lysis.

For each assay, the PBMC collected from one donor was used. Blood was drawn into heparinized tubes (approximately 50 mL of blood/donor) at which time UNI-SEP maxi tubes (NOVAmed, LTD.) were used for density gradient separation of the lymphocytes. Approximately 3 mL of PBMC at $1.6 \times 10^7$ cells/mL was obtained with each donor.

Each assay used an effector to target ratio of 40 to 1, 5 μg/mL of antibody. After 4-h incubation in a humidified incubator at 37° C., 5% $CO_2$, the plates were removed from the incubator, allowed to reach room temperature, and analyzed with CytoTox-One Homogenous Membrane Integrity Assay Kit according to manufacturer's protocol. The percent of lysis for each sample in 6 replicates was determined using the following formula:

$$\% \text{ Lysis} = \frac{[\text{Experimental} - (\text{Effector} + \text{Target Control})]}{(\text{Maximum Lysis} - \text{Target Control})} \times 100$$

The table below summarizes the ADCC results (% lysis) obtained with Daudi as the target cell from three donors. For each donor, the difference between YDE and either v-mab or V102Y was statistically significant (p<0.0001 for donor 009; p<0.0002 for donor 006; p<0.02 for donor 001). The difference between v-mab and V102Y was not statistically significant. The isotype control (h734 IgG) showed minimal ADCC.

|         | Donor 009    | Donor 006     | Donor 001    |
|---------|--------------|---------------|--------------|
| v-mab   | 36.7 ± 3.7   | 21.1 ± 4.2    | 52.5 ± 4.3   |
| V102Y   | 33.4 ± 7.7   | 24.2 ± 2.7    | 47.5 ± 0.5   |
| YDE     | 54.5 ± 2.7   | 31.5 ± 3.6    | 58.3 ± 3.3   |
| h734 IgG| 4.2 ± 2.6    | 0.06 ± 3.5    | 4.2 ± 2.8    |

All of the COMPOSITIONS and METHODS disclosed and claimed herein can be made and used without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the METHODS described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

This application is based on and claims priority to U.S. Provisional Patent Application Ser. No. 61/082,399, filed Jul. 21, 2008. The disclosure of the priority application in its entirety, including the drawings, claims, and the specification thereof, is incorporated herein by reference. In addition, the content of all articles, patents and patent applications referenced herein are incorporated in their entirety.

What is claimed is:

1. A method of improving a chimeric or humanized anti-CD20 antibody or antigen-binding fragment thereof comprising making at least one amino acid substitution in the third complementarity determining region (CDR) sequence of the heavy chain of a chimeric or humanized or human anti-CD20 antibody or antigen binding fragment thereof to make a substituted antibody or antigen binding fragment thereof, wherein the substitution results in at least one improved characteristic selected from the group consisting of a slower off-rate, slower antigen dissociation rate, higher CDC activity, higher ADCC activity, higher apoptotic activity, greater ability to induce cell death in vitro in the absence of cross-linking and greater ability to kill or inhibit the growth of CD20-positive cells in vivo when administered to a subject with CD20-positive cells, wherein the CDR sequences of the unsubstituted anti-CD20 antibody or antigen-binding fragment thereof comprise the light chain CDR sequences CDRL1 (RASSSVSYIH; SEQ ID NO:1), CDRL2 (ATSN-LAS; SEQ ID NO:2) and CDRL3 (QQWTSNPPT; SEQ ID NO:3) and heavy chain CDR sequences CDRH1 (SYNMH; SEQ ID NO:4), CDRH2(AIYPGNGDTSYNQKFKG; SEQ ID NO:5) and CDRH3(STYYGGDWYFNV; SEQ ID NO:32) and wherein the substitution comprises replacing the asparagine residue at Kabat position 101 of the heavy chain CDR3 (CDRH3) of the antibody with an aspartate residue.

2. The method of claim 1 wherein the CD20-positive cells are B-cells.

3. The method of claim 1, wherein the substituted antibody comprises an arginine residue at Kabat position 94 and the aspartate residue at Kabat position 101 forms an ionic bond with the arginine residue at Kabat position 94.

4. The method of claim 1, wherein the substituted antibody or fragment thereof inhibits binding to CD20 of rituximab.

5. The method of claim 1, wherein the substituted antibody is veltuzumab.

6. The method of claim 1, wherein substitution of aspartate for asparagine at Kabat position 101 results in at least a two-fold slower dissociation rate of the anti-CD20 antibody from CD20.

7. A method of improving a chimeric or humanized anti-CD20 antibody or antigen-binding fragment thereof comprising making at least one amino acid substitution in the third complementarity determining region (CDR) sequence of the heavy chain of a chimeric or humanized anti-CD20 antibody or antigen binding fragment thereof to make a substituted antibody or antigen binding fragment thereof, wherein the substitution results in at least one improved characteristic selected from the group consisting of a slower off-rate, slower antigen dissociation rate, higher CDC activity, higher ADCC activity, higher apoptotic activity, greater ability to induce cell death in vitro in the absence of cross-linking and greater ability to kill or inhibit the growth of CD20-positive cells in vivo when administered to a subject with CD20-positive cells, wherein the substituted anti-CD20 antibody or fragment thereof comprises the light chain CDR sequences CDRL1 (RASSSVSYIH; SEQ ID NO:1), CDRL2 (ATSN-LAS; SEQ ID NO:2) and CDRL3 (QQWTSNPPT; SEQ ID NO:3) and heavy chain CDR sequences CDRH1 (SYNMH; SEQ ID NO:4), CDRH2 (AIYPGNGDTSYNQKFKG; SEQ ID NO:5) and CDRH3 (STYYGGDWYFDV; SEQ ID NO:6).

8. The method of claim 1, wherein the humanized anti-CD20 antibody comprises the framework region sequences of the humanized anti-CD22 antibody, epratuzumab, or the framework region sequences of the humanized anti-CD20 antibody, veltuzumab.

9. The method of claim 1, wherein substitution of aspartate for the asparagine residue at Kabat position 101 results in an increase in complement-dependent cytotoxicity of Daudi cells exposed to the antibody.

10. The method of claim 1, wherein substitution of aspartate for the asparagine residue at Kabat position 101 results in a 30 to 40% reduction in $EC_{50}$ in complement-dependent cytotoxicity of Daudi cells exposed to the antibody.

11. The method of claim 7, wherein the CD20-positive cells are B-cells.

12. The method of claim 7, wherein the substituted antibody comprises an arginine residue at Kabat position 94 and the aspartate residue at Kabat position 101 forms an ionic bond with the arginine residue at Kabat position 94.

13. The method of claim 7, wherein the substituted antibody or fragment thereof inhibits binding to CD20 of rituximab.

14. The method of claim 7, wherein the substituted antibody is veltuzumab.

15. The method of claim 7, wherein substitution of aspartate for asparagine at Kabat position 101 results in at least a two-fold slower dissociation rate of the anti-CD20 antibody from CD20.

16. The method of claim 7, wherein the CDR sequences of the unsubstituted antibody are identical to the CDR sequences of a murine anti-CD20 antibody.

17. The method of claim 7, wherein the humanized anti-CD20 antibody comprises the framework region sequences of the humanized anti-CD22 antibody, epratuzumab, or the framework region sequences of the humanized anti-CD20 antibody, veltuzumab.

18. The method of claim 7, wherein substitution of aspartate for the asparagine residue at Kabat position 101 results in an increase in complement-dependent cytotoxicity of Daudi cells exposed to the antibody.

19. The method of claim 7, wherein substitution of aspartate for the asparagine residue at Kabat position 101 results in a 30 to 40% reduction in $EC_{50}$ in complement-dependent cytotoxicity of Daudi cells exposed to the antibody.

* * * * *